(12) United States Patent
Lin et al.

(10) Patent No.: US 7,163,939 B2
(45) Date of Patent: Jan. 16, 2007

(54) MACROCYCLIC KINASE INHIBITORS

(75) Inventors: Nan-Horng Lin, Vernon Hills, IL (US); Gaoquan Li, Park City, IL (US); Magdalena K. Przytulinska, Chicago, IL (US); Thomas J. Sowin, Wadsworth, IL (US); Gerard M. Sullivan, Lake Villa, IL (US); Zhi-Fu Tao, Gurnee, IL (US); Yunsong Tong, Libertyville, IL (US); Le Wang, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 209 days.

(21) Appl. No.: 10/980,740

(22) Filed: Nov. 3, 2004

(65) Prior Publication Data

US 2005/0215556 A1 Sep. 29, 2005

Related U.S. Application Data

(60) Provisional application No. 60/517,627, filed on Nov. 5, 2003.

(51) Int. Cl.
*C07D 513/08* (2006.01)
*A61K 31/529* (2006.01)

(52) U.S. Cl. .............. 514/231.5; 514/250; 540/456
(58) Field of Classification Search ............. 540/456; 514/250, 231.5
See application file for complete search history.

(56) References Cited

U.S. PATENT DOCUMENTS

2003/0069284 A1   4/2003   Keegan et al. ............ 514/345

FOREIGN PATENT DOCUMENTS

EP          0 792 875        9/1997
WO       2004/026881        4/2004

OTHER PUBLICATIONS

Tyle, "Iontophoretic devices for drug delivery," Pharmaceutical Research 3(6):318-326 (1986).

*Primary Examiner*—Bruck Kifle
(74) *Attorney, Agent, or Firm*—Johanna M Corbin

(57) ABSTRACT

Compounds having the formula

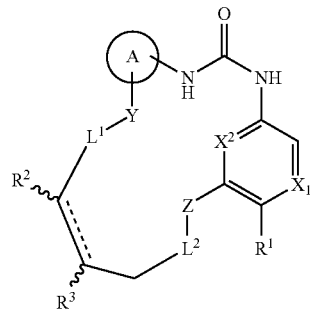

are useful for inhibiting protein kinases. Also disclosed are methods of making the compounds, compositions containing the compounds, and methods of treatment using the compounds.

6 Claims, No Drawings

MACROCYCLIC KINASE INHIBITORS

This application claims priority from U.S. Provisional Patent Application No. 60/517,627, filed Nov. 5, 2003, incorporated herein by reference.

TECHNICAL FIELD

The present invention relates to substituted ureas which are useful for inhibiting protein kinases, methods of making the compounds, compositions containing the compounds, and methods of treatment using the compounds.

BACKGROUND OF THE INVENTION

Protein kinases have been clearly shown to be important in the progression of many disease states that are induced by the inappropriate proliferation of cells. These kinases are often found to be up-regulated in many hyperproliferative states such as cancer. These kinases may be important in cell signaling, where their inappropriate activation induces cells to proliferate (e.g., EGFR, ERBB2, VEGFR, FGFR, PDGFR, c-Met, IGF-1R, RET, TIE2). Alternatively, they may be involved in signal transduction within cells (e.g., c-Src, PKC, Akt, PKA, c-Abl, PDK-1). Often these signal transduction genes are recognized proto-oncogenes. Many of these kinases control cell cycle progression near the G1-S transition (e.g., Cdk2, Cdk4), at the G2-M transition (e.g., Wee1, Myt1, Chk1, Cdc2) or at the spindle checkpoint (P1k, Aurora1 or 2, Bub1 or 3). Furthermore, kinases are intimately linked to the DNA damage response (e.g., ATM, ATR, Chk1, Chk2). Deregulation of these cellular functions: cell signaling, signal transduction, cell cycle control, and DNA repair, are all hallmarks of hyperproliferative diseases, particularly cancer. It is therefore likely that pharmacological modulation of one or more kinases would be useful in slowing or stopping disease progression in these diseases.

SUMMARY OF THE INVENTION

In its principle embodiment the present invention provides a compound of formula (I)

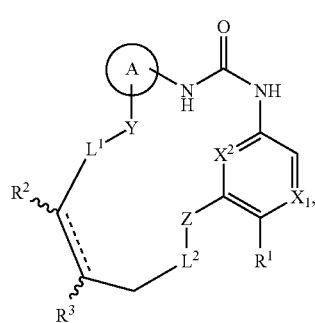

(I)

or a therapeutically acceptable salt thereof, wherein

----- is a single or double bond;

A is selected from the group consisting of aryl and heteroaryl, wherein the aryl and the heteroaryl are optionally substituted with one, two, or three substituents independently selected from the group consisting of alkoxy, alkoxyalkoxy, alkoxyalkoxyalkoxy, alkyl, cyano, halo, haloalkylsulfonyloxy, haloalkoxy, heteroarylalkoxy, heterocycle, heterocyclealkoxy, heterocycleoxyalkoxy, heterocycleoxyalkyl, heterocycleoxyalkynyl, heteroarylcarbonylalkoxy, haloalkyl, hydroxyalkenyl, hydroxyalkoxy, hydroxyalkyl, hydroxyalkynyl, hydroxy, nitro, $NR^aR^b$, $(NR^aR^b)$alkoxy, $(NR^aR^b)$alkyl, and $(NR^aR^b)$alkynyl;

$R^1$ is selected from the group consisting of hydrogen, alkoxycarbonyl, alkyl, carboxy, cyano, halo, and nitro;

$R^2$ and $R^3$ are independently selected from the group consisting of hydrogen, alkoxy, alkoxycarbonyl, alkyl, alkylsulfonyl, arylsulfonyl, halo, hydroxy, and $NR^aR^b$;

or $R^2$ and $R^3$, together with the atoms to which they are attached, form an epoxide;

$X^1$ and $X^2$ are independently selected from the group consisting of CH and N;

Y and Z are independently selected from the group consisting of $CH_2$, O, and $NR^z$, wherein $R^z$ is selected from the group consisting of hydrogen and alkyl;

$L^1$ and $L^2$ are independently selected from the group consisting of a bond and alkylene;

$R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; and A, $X^1$, $X^2$, Y, Z, $R^1$, $R^2$, $R^3$, and

----- are as defined in formula (I).

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$ alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$ alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$, together with the atoms to which they are attached, form an epoxide; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; and A, $X^1$, $X^2$, Y, Z, $R^1$, $R^2$, $R^3$, and

----- are as defined in formula (I).

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and
$R^a$ and $R^b$ are both hydrogen.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is $CH_2$; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkyl, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, ($NR^aR^b$)alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, alkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(N^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, ($NR^aR^b$)alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(N^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, an d $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$, together with the atoms to which they are attached, form an epoxide; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from t group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; and A, $X^1$, $X^2$, Y, Z, $R^1$, $R^2$, $R^3$, and

----- are as defined in formula (I).

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; and R$^a$ and R$^b$ are both hydrogen.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylalkyl wherein the heteroaryl portion of heteroarylalkyl is pyridinyl.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocycle, wherein the heterocycle is piperidinyl;

----- is a single bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$; L$^2$ is CH$_2$; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is $CH_2$; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, NR$^a$R$^b$, (NR$^a$R$^b$)alkoxy, (NR$^a$R$^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; and R$^a$ and R$^b$ are both hydrogen.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylalkyl wherein the heteroaryl portion of heteroarylalkyl is pyridinyl.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is CH$_2$CH(OH); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is selected from the group consisting of $CH_2CH(OCH_3)$ and $CH_2CH$ (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocycle, wherein the heterocycle is piperidinyl;

----- is a single bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, and (NR$^a$R$^b$)alkoxy;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocyclealkoxy, wherein the heterocycle portion of heterocyclealkoxy is selected from the group consisting of morpholinyl, piperidinyl, and pyrrolidinyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is selected from the group consisting of CH$_2$CH(OCH$_3$) and CH$_2$CH (OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, NR$^a$R$^b$, (NR$^a$R$^b$)alkoxy, (NR$^a$R$^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (N$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; and R$^a$ and R$^b$ are both hydrogen.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylalkyl wherein the heteroaryl portion of heteroarylalkyl is pyridinyl.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein L$^1$ is selected from the group consisting of CH$_2$CH(OCH$_3$) and CH$_2$CH(OCH$_2$CH$_3$); L$^2$ is a bond; X$^1$ is N; X$^2$ is CH; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is N; $X^2$ is CH; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; and R$^a$ and R$^b$ are both hydrogen.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylalkyl wherein the heteroaryl portion of heteroarylalkyl is pyridinyl.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a single bond; R$^a$ is hydrogen; and R$^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocycle, wherein the heterocycle is piperidinyl;

----- is a single bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$; L$^2$ is a bond; X$^1$ is CH; X$^2$ is N; Y is O; Z is O; R$^1$ is selected from the group consisting of hydrogen and cyano; R$^2$ and R$^3$, together with the atoms to which they are attached, form an epoxide; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroaryalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; and A, $X^1$, $X^2$, Y, Z, $R^1$, $R^2$, $R^3$, and

----- are as defined in formula (I).

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, ($NR^aR^b$) alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and ($NR^aR^b$)alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, ($NR^aR^b$)alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, ($NR^aR^b$)alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2$; $L^2$ is $CH_2$; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH(CH_3)CH_2$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocyclealkoxy, wherein the heterocycle portion of heterocyclealkoxy is selected from the group consisting of morpholinyl, piperidinyl, and pyrrolidinyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (N$^a$R$^b$)alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, NR$^a$R$^b$, (NR$^a$R$^b$)alkoxy, (NR$^a$R$^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; and R$^a$ and R$^b$ are both hydrogen.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylalkyl wherein the heteroaryl portion of heteroarylalkyl is pyridinyl.

In another embodiment the present invention provides a compound of formula (I) wherein L$^1$ is CH$_2$CH(OH); L$^2$ is a bond; X$^1$ is CH; X$^2$ is N; Y is O; Z is O; R$^1$ is selected from the group consisting of hydrogen and cyano; R$^2$ and R$^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L$^1$ is CH$_2$CH(OH); L$^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is $CH_2CH(OH)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH$ $(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH$ $(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH$ $(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, ($NR^aR^b$)alkoxy, ($NR^aR^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and ($NR^cR^d$)alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; and $R^a$ and $R^b$ are both hydrogen.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are independently selected from the group consisting of hydrogen, alkoxy, and hydroxy; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocycle, wherein the heterocycle is piperidinyl;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, and heterocyclealkoxy, wherein the heterocycle portion of heterocyclealkoxy is selected from the group consisting of morpholinyl, piperidinyl, and pyrrolidinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, $(NR^aR^b)$alkoxy, heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, $NR^aR^b$, $(NR^aR^b)$alkoxy, $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (I) wherein $L^1$ is selected from the group consisting of $CH_2CH(OCH_3)$ and $CH_2CH(OCH_2CH_3)$; $L^2$ is a bond; $X^1$ is CH; $X^2$ is N; Y is O; Z is O; $R^1$ is selected from the group consisting of hydrogen and cyano; $R^2$ and $R^3$ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and $NR^aR^b$;

----- is a double bond; and $R^a$ and $R^b$ are both hydrogen.

In another embodiment the present invention provides a compound of formula (I) wherein L¹ is selected from the group consisting of CH₂CH(OCH₃) and CH₂CH(OCH₂CH₃); L² is a bond; X¹ is CH; X² is N; Y is O; Z is O; R¹ is selected from the group consisting of hydrogen and cyano; R² and R³ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylalkyl wherein the heteroaryl portion of heteroarylalkyl is pyridinyl.

In another embodiment the present invention provides a compound of formula (I) wherein L¹ is selected from the group consisting of CH₂CH(OCH₃) and CH₂CH(OCH₂CH₃); L² is a bond; X¹ is CH; X² is N; Y is O; Z is O; R¹ is selected from the group consisting of hydrogen and cyano; R² and R³ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylcarbonyl wherein the heteroaryl portion of heteroarylcarbonyl is pyridinyl.

In another embodiment the present invention provides a compound of formula (I) wherein L¹ is selected from the group consisting of CH₂CH(OCH₃) and CH₂CH(OCH₂CH₃); L² is a bond; X¹ is CH; X² is N; Y is O; Z is O; R¹ is selected from the group consisting of hydrogen and cyano; R² and R³ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (I) wherein L¹ is selected from the group consisting of CH₂CH(OCH₃) and CH₂CH(OCH₂CH₃); L² is a bond; X¹ is CH; X² is N; Y is O; Z is O; R¹ is selected from the group consisting of hydrogen and cyano; R² and R³ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, hydroxyalkynyl, nitro, and NR$^a$R$^b$;

----- is a double bond; R$^a$ is hydrogen; and R$^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (I) wherein L¹ is selected from the group consisting of CH₂CH(OCH₃) and CH₂CH(OCH₂CH₃); L² is a bond; X¹ is CH; X² is N; Y is O; Z is O; R¹ is selected from the group consisting of hydrogen and cyano; R² and R³ are both hydrogen; A is aryl wherein the aryl is phenyl substituted with one or two substituents selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, NR$^a$R$^b$, (NR$^a$R$^b$)alkoxy, and heterocycle, wherein the heterocycle is piperidinyl;

----- is a double bond; R$^a$ and R$^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (II)

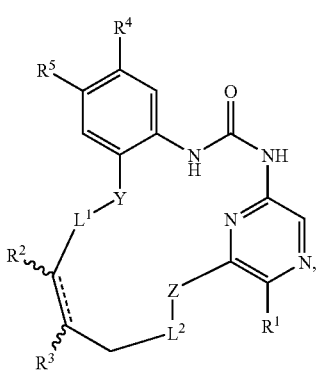

(II)

or a therapeutically acceptable salt thereof, wherein

----- is a single or double bond;

R¹ is selected from the group consisting of hydrogen, alkoxycarbonyl, alkyl, carboxy, cyano, halo, and nitro;

$R^2$ and $R^3$ are independently selected from the group consisting of hydrogen, alkoxy, alkoxycarbonyl, alkyl, alkylsulfonyl, arylsulfonyl, halo, hydroxy, and $NR^aR^b$;

or $R^2$ and $R^3$, together with the atoms to which they are attached, form an epoxide;

$R^4$ is selected from the group consisting of alkoxy, alkyl, cyano, halo, heterocycleoxyalkoxy, heterocycleoxyalkyl, hydroxy, hydroxyalkoxy, hydroxyalkyl, nitro, $NR^aR^b$, and $(NR^aR^b)$alkoxy;

$R^5$ is selected from the group consisting of hydrogen, alkenyl, alkoxy, alkoxyalkoxy, alkoxyalkoxyalkyl, alkoxyalkyl, alkoxycarbonyl, alkoxycarbonylalkyl, alkylsulfanyl, arylsulfanyl, alkylsulfonyl, arylsulfonyl, carboxy, carboxyalkyl, haloalkylsulfonyloxy, heteroarylalkoxy, heteroarylcarbonylalkoxy, heterocycle, heterocyclealkoxy, heterocycleoxyalkyl, heterocycleoxyalkynyl, hydroxy, hydroxyalkoxy, hydroxyalkyl, hydroxyalkynyl, $NR^aR^b$, $(NR^aR^b)$alkoxy, $(NR^aR^b)$alkyl, $(NR^aR^b)$alkynyl, $(NR^aR^b)$carbonyl, $(NR^aR^b)$carbonylalkoxy, and $(NR^aR^b)$carbonylalkyl;

Y and Z are independently selected from the group consisting of $CH_2$, O, and $NR^z$, wherein $R^z$ is selected from the group consisting of hydrogen and alkyl;

$L^1$ and $L^2$ are independently selected from the group consisting of a bond and alkylene;

$R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl, and $(NR^cR^d)$alkylcarbonyl; and $R^c$ and $R^d$ are independently selected from the group consisting of hydrogen, alkyl, and cycloalkyl.

In another embodiment the present provides a compound of formula (II) wherein $R^1$ is selected from the group consisting of hydrogen and cyano; $R^2$ and $R^3$ are independently selected from the group consisting of hydrogen, alkoxy, and hydroxy; $R^4$ is halo; $R^5$ is hydrogen; Y is O; Z is O; $L^1$ is $CH_2$; and $L^2$ and

----- are as defined in formula (II).

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkyl, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a single bond; and $R^a$ and $R^b$ are independently selected from the group consisting of hydrogen and alkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a single bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a single bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a single bond.

In another embodiment the present invention provides a compound of formula (II) wherein $L^1$ is $CH_2$; $L^2$ is a bond;

Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; and $R^a$ and $R^b$ are selected from the group consisting of hydrogen and alkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a single bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$, together with the atoms to which they are attached, form an epoxide; $R^4$ is halo; $R^5$ is selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a double bond; and $R^a$ and $R^b$ are independently selected from the group consisting of hydrogen and alkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a double bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a double bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a double bond.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; and $R^a$ and $R^b$ are selected from the group consisting of hydrogen and alkyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy;

$R^4$ is halo; $R^5$ is heterocycle, wherein the heterocycle is piperidinyl;

----- is a double bond.

In another embodiment the present invention provides a compound of formula (II) wherein $L^1$ is $CH_2$; $L^2$ is $CH_2$; and A, X, Y, Z, $R^1$, $R^2$, $R^3$, and

----- are as defined in formula (I).

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a single bond; and $R^a$ and $R^b$ are independently selected from the group consisting of hydrogen and alkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a single bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a single bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a single bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; and $R^a$ and $R^b$ are selected from the group consisting of hydrogen and alkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a single bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$, together with the atoms to which they are attached, form an epoxide; $R^4$ is halo; $R^5$ is selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a double bond; and $R^a$ and $R^b$ are independently selected from the group consisting of hydrogen and alkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a double bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a double bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of ($NR^aR^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a double bond.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; and $R^a$ and $R^b$ are selected from the group consisting of hydrogen and alkyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2$; $L^2$ is $CH_2$; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a double bond.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and ($NR^aR^b$)alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is selected from the group consisting of alkoxy, alkyl, heterocycleoxyalkoxy, heterocycleoxyalkyl, hydroxy, hydroxyalkyl, nitro, and (NR$^a$R$^b$)alkoxy, wherein the heterocycle portion of heterocycleoxyalkoxy and heterocycleoxyalkyl is tetrahydropyranyl; R$^5$ is hydrogen;

----- is a single bond; and R$^a$ and R$^b$ are independently selected from the group consisting of hydrogen and alkyl.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is heterocyclealkoxy, wherein the heterocycle portion of heterocyclealkoxy is selected from the group consisting of morpholinyl, piperidinyl, and pyrrolidinyl; and

----- is a single bond.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a single bond.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is selected from the group consisting of (NR$^a$R$^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a single bond.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a single bond; and R$^a$ and R$^b$ are selected from the group consisting of hydrogen and alkyl.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a single bond; R$^a$ is hydrogen; and R$^b$ is heteroarylalkyl wherein the heteroaryl portion of heteroarylalkyl is pyridinyl.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a single bond; R$^a$ is hydrogen; and R$^b$ is heteroarylcarbonyl wherein the heteroaryl portion of heteroarylcarbonyl is pyridinyl.

In another embodiment the present invention provides a compound of formula (II) wherein L$^1$ is CH(CH$_3$)CH$_2$; L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a single bond; R$^a$ is hydrogen; and R$^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein L$^1$ is CH(CH$_3$)CH$_2$; L$^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a single bond.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$, together with the atoms to which they are attached, form an epoxide; $R^4$ is halo; $R^5$ is selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a double bond; and $R^a$ and $R^b$ are independently selected from the group consisting of hydrogen and alkyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a double bond.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a double bond.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a double bond.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; and $R^a$ and $R^b$ are selected from the group consisting of hydrogen and alkyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH(CH_3)CH_2$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a double bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkyl, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a single bond; and $R^a$ and $R^b$ are independently selected from the group consisting of hydrogen and alkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a single bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a single bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a single bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; and $R^a$ and $R^b$ are selected from the group consisting of hydrogen and alkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^a$ is $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a single bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$, together with the atoms to which they are attached, form an epoxide; $R^4$ is halo; $R^5$ is selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$alkoxy, wherein the heterocycle portion of heterocycleoxyalkoxy and heterocycleoxyalkyl is tetrahydropyranyl; $R^5$ is hydrogen;

----- is a double bond; and $R^a$ and $R^b$ are independently selected from the group consisting of hydrogen and alkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a double bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a double bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a double bond.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^a$ is $NR^aR^b$;

----- is a double bond; and $R^a$ and $R^b$ are selected from the group consisting of hydrogen and alkyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is $CH_2CH(OH)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a double bond.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a single bond; $R^a$ and $R^b$ are independently selected from the group consisting of hydrogen, alkyl, alkylcarbonyl, alkylsulfonyl, haloalkylcarbonyl, haloalkylsulfonyl, and $(NR^cR^d)$alkylcarbonyl; and $R^c$ and $R^d$ are independently selected from the group consisting of hydrogen, alkyl, and cycloalkyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is selected from the group consisting of alkoxy, alkyl, heterocycleoxyalkoxy, heterocycleoxyalkyl, hydroxy, hydroxyalkyl, nitro, and $(NR^aR^b)$ alkoxy, wherein the heterocycle portion of heterocycleoxyalkoxy and heterocycleoxyalkyl is tetrahydropyranyl; $R^5$ is hydrogen;

----- is a single bond; and $R^a$ and $R^b$ are independently selected from the group consisting of hydrogen and alkyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocyclealkoxy, wherein the heterocycle portion of heterocyclealkoxy is selected from the group consisting of morpholinyl, piperidinyl, and pyrrolidinyl; and

----- is a single bond.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a single bond.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of $(NR^aR^b)$alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a single bond.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; and $R^a$ and $R^b$ are selected from the group consisting of hydrogen and alkyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylalkyl wherein the heteroaryl portion of heteroarylalkyl is pyridinyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylcarbonyl wherein the heteroaryl portion of heteroarylcarbonyl is pyridinyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a single bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a single bond.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$, together with the atoms to which they are attached, form an epoxide; $R^4$ is halo; $R^5$ is selected from the group consisting of alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy; $R^a$ and $R^b$ are independently selected from the group consisting of hydrogen, alkyl, alkylcarbonyl, alkylsulfonyl, haloalkylcarbonyl, haloalkylsulfonyl, $(NR^cR^d)$alkylcarbonyl, and heteroarylalkyl, wherein the heteroaryl portion of heteroarylalkyl is pyridinyl; and $R^c$ and $R^d$ are independently selected from the group consisting of hydrogen, alkyl, and cycloalkyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is selected from the group consisting of hydrogen, alkenyl, alkoxy, alkoxyalkoxy, alkoxyalkoxyalkoxy, alkyl, halo, haloalkylsulfonyloxy, hydroxy, hydroxyalkoxy, hydroxyalkyl, nitro, $NR^aR^b$, and $(NR^aR^b)$alkoxy;

----- is a double bond; $R^a$ and $R^b$ are independently selected from the group consisting of hydrogen, alkyl, alkylcarbonyl, alkylsulfonyl, haloalkylcarbonyl, haloalkylsulfonyl, and (NR$^c$R$^d$)alkylcarbonyl; and R$^c$ and R$^d$ are independently selected from the group consisting of hydrogen, alkyl, and cycloalkyl.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is selected from the group consisting of alkoxy, alkyl, heterocycleoxyalkoxy, heterocycleoxyalkyl, hydroxy, hydroxyalkyl, nitro, and (NR$^a$R$^b$)alkoxy, wherein the heterocycle portion of heterocycleoxyalkoxy and heterocycleoxyalkyl is tetrahydropyranyl; R$^5$ is hydrogen;

----- is a double bond; and R$^a$ and R$^b$ are independently selected from the group consisting of hydrogen and alkyl.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is heterocyclealkoxy, wherein the heterocycle portion of heterocyclealkoxy is selected from the group consisting of morpholinyl, piperidinyl, and pyrrolidinyl; and

----- is a double bond.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is selected from the group consisting of heteroarylalkoxy, and heteroarylcarbonylalkoxy, wherein the heteroaryl portion of heteroarylalkoxy and heteroarylcarbonylalkoxy is selected from the group consisting of imidazolyl and pyridinyl; and

----- is a double bond.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is selected from the group consisting of (NR$^a$R$^b$)alkynyl, heterocycleoxyalkoxy, heterocycleoxyalkyl, and heterocycleoxyalkynyl, wherein the heterocycle portion of heterocycleoxyalkoxy, heterocycleoxyalkyl, and heterocycleoxyalkynyl is tetrahydropyranyl; and

----- is a double bond.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a double bond; and R$^a$ and R$^b$ are selected from the group consisting of hydrogen and alkyl.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a double bond; R$^a$ is hydrogen; and R$^b$ is heteroarylalkyl wherein the heteroaryl portion of heteroarylalkyl is pyridinyl.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a double bond; R$^a$ is hydrogen; and R$^b$ is heteroarylcarbonyl wherein the heteroaryl portion of heteroarylcarbonyl is pyridinyl.

In another embodiment the present invention provides a compound of formula (II) wherein L$^1$ is selected from the group consisting of CH$_2$CH(OCH$_3$) and CH$_2$CH (OCH$_2$CH$_3$); L$^2$ is a bond; Y is O; Z is O; R$^1$ is selected from the group consisting of hydrogen and cyano; R$^2$ and R$^3$ are independently selected from the group consisting of hydrogen, alkoxy, and hydroxy; R$^4$ is halo; R$^5$ is NR$^a$R$^b$;

----- is a double bond; $R^a$ is hydrogen; and $R^b$ is arylsulfonyl wherein the aryl portion of arylsulfonyl is phenyl optionally substituted with one substituent selected from the group consisting of alkoxy, alkyl, haloalkoxy, haloalkyl, halo, and hydroxy.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is $NR^aR^b$;

----- is a double bond; $R^a$ is hydrogen; and $R^b$ is heteroarylsulfonyl wherein the heteroaryl portion of heteroarylsulfonyl is pyridinyl optionally substituted with one substituent selected from the group consisting of alkoxy, alkyl, haloalkoxy, haloalkyl, halo, hydroxy, and heterocycle, wherein the heterocycle is morpholinyl.

In another embodiment the present invention provides a compound of formula (II) wherein $L^1$ is selected from the group consisting of $CH_2CH(OCH_3)$ and $CH_2CH(OCH_2CH_3)$; $L^2$ is a bond; Y is O; Z is O; $R^1$ is selected from the group consisting of hydrogen and cyano; $R^2$ and $R^3$ are independently selected from the group consisting of hydrogen, alkoxy, and hydroxy; $R^4$ is halo; $R^5$ is heterocycle, wherein the heterocycle is piperidinyl;

----- is a double bond.

In another embodiment the present invention provides a pharmaceutical composition comprising a compound of claim 1 or a therapeutically acceptable salt thereof, in combination with a therapeutically acceptable carrier.

In another embodiment the present invention provides a method for inhibiting protein kinases in a patient in recognized need of such treatment comprising administering to the patient a therapeutically acceptable amount of a compound of claim 1, or a therapeutically acceptable salt thereof.

In another embodiment the present invention provides a method for treating cancer in a patient in recognized need of such treatment comprising administering to the patient a therapeutically acceptable amount of a compound of claim 1, or a therapeutically acceptable salt thereof.

DETAILED DESCRIPTION OF THE INVENTION

All publications, issued patents, and patent applications cited herein are hereby incorporated by reference.

As used in the present specification the following terms have the meanings indicated:

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkoxy," as used herein, refers to an alkoxy group substituted with at least one alkoxy group.

The term "alkoxyalkoxyalkoxy," as used herein, refers to an alkoxyalkoxy group substituted with one alkoxy group.

The term "alkoxyalkyl," as used herein, refers to an alkyl group substituted with at least one alkoxy group.

The term "alkoxycarbonyl," as used herein, refers to an alkoxy group attached to the parent molecular moiety through a carbonyl group.

The term "alkoxycarbonylalkyl," as used herein, refers to an alkyl group substituted with at least one alkoxycarbonyl group.

The term "alkyl," as used herein, refers to a group derived from a straight or branched chain saturated hydrocarbon containing from one to ten carbon atoms. Preferred alkyl groups contain from one to four carbon atoms.

The term "alkylcarbonyl," as used herein, refers to an alkyl group attached to the parent molecular moiety through a carbonyl group.

The term "alkylene" means a divalent group derived from a straight or branched chain hydrocarbon of from 1 to 6 carbon atoms. The alkylene is optionally substituted with 1 or 2 substituents selected from the group consisting of alkoxy and hydroxy. Representative examples of alkylene include, but are not limited to, $-CH_2-$, $-CH(CH_3)-$, $-C(CH_3)_2-$, $-CH_2CH_2-$, $-CH_2CH(CH_3)-$, $-CH_2CH(OH)-$, $-CH_2CH(OCH_3)-$, $-CH_2CH(OCH_2CH_3)-$, $-CH_2CH_2CH_2-$, $-CH_2CH_2CH_2CH_2-$, and $-CH_2CH(CH_3)CH_2-$.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkoxyalkoxy, alkoxyalkoxyalkoxy, alkyl, cyano, halo, haloalkylsulfonyloxy, haloalkoxy, heteroarylalkoxy, heterocycle, heterocyclealkoxy, heterocycleoxyalkoxy, heterocycleoxyalkyl, heterocycleoxyalkynyl, heteroarylcarbonylalkoxy, haloalkyl, hydroxyalkenyl, hydroxyalkoxy, hydroxyalkyl, hydroxyalkynyl, hydroxy, nitro, $NR^aR^b$, $(NR^aR^b)$alkoxy, $(NR^aR^b)$alkyl, and $(NR^aR^b)$alkynyl.

The term "arylalkyl," as used herein, refers to an alkyl substituted with at least one aryl group.

The term "arylsulfanyl," as used herein, refers to an aryl group attached to the parent molecular moiety through a sulfur atom.

The term "arylsulfonyl," as used herein, refers to an aryl group attached to the parent molecular moiety through a sulfonyl group.

The term "carbonyl," as used herein, refers to $-C(O)-$.

The term "carboxy," as used herein, refers to —CO$_2$H.

The term "carboxyalkyl," as used herein, refers to an alkyl group substituted with at least one carboxy group.

The term "cyano," as used herein, refers to —CN.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl. The cycloalkyl groups of the present invention can optionally be substituted with 1, 2, 3, or 4 substituents independently selected from the group consisting of alkoxy, alkoxyalkoxy, alkyl, cyano, halo, haloalkylsulfonyloxy, haloalkoxy, haloalkyl, hydroxyalkenyl, hydroxyalkoxy, hydroxyalkyl, hydroxyalkynyl, hydroxy, NR$^a$R$^b$, (NR$^a$R$^b$)alkoxy, (NR$^a$R$^b$)alkyl, and (NR$^a$R$^b$)alkynyl.

The term "epoxide," as used herein, refers to a

group.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylcarbonyl," as used herein, refers to a haloalkyl group attached to the parent molecular moiety through a carbonyl group.

The term "haloalkylsulfonyl," as used herein, refers to a haloalkyl group attached to the parent molecular moiety through a sulfonyl group.

The term "haloalkylsulfonyloxy," as used herein, refers to a haloalkylsulfonyl group attached to the parent molecular moiety through an oxygen atom.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular moiety through a substitutable carbon or nitrogen atom in the ring. The term "heteroaryl" also includes bicyclic systems where a heteroaryl ring is fused to a phenyl group, a monocyclic cycloalkenyl group, as defined herein, a monocyclic cycloalkyl group, as defined herein, a monocyclic heterocycle group, as defined herein, or an additional monocyclic heteroaryl group; and tricyclic systems where a bicyclic system is fused to a phenyl group, a monocyclic cycloalkenyl group, as defined herein, a monocyclic cycloalkyl group, as defined herein, a heterocyclyl group, as defined herein, or an additional monocyclic heteroaryl group. Representative examples of heteroaryl groups include, but are not limited to, benzoxadiazolyl, benzoxazolyl, benzofuranyl, benzothienyl, cinnolinyl, dibenzofuranyl, furanyl, imidazolyl, indazolyl, indolyl, isoxazolyl, isoquinolinyl, isothiazolyl, naphthyridinyl, oxadiazolyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, triazinyl, and the like. The heteroaryl groups of the present invention can be optionally substituted with one, two, three, four, or five substituents independently selected from the group consisting of alkoxy, alkoxyalkoxy, alkoxyalkoxyalkoxy, alkyl, cyano, halo, haloalkylsulfonyloxy, haloalkoxy, haloalkyl, heteroarylalkoxy, heterocycle, heterocyclealkoxy, heterocycleoxyalkoxy, heterocycleoxyalkyl, heterocycleoxyalkynyl, heteroarylcarbonylalkoxy, haloalkyl, hydroxyalkenyl, hydroxyalkoxy, hydroxyalkyl, hydroxyalkynyl, hydroxy, nitro, NR$^a$R$^b$, (NR$^a$R$^b$)alkoxy, (NR$^a$R$^b$)alkyl, and (NR$^a$R$^b$)alkynyl, wherein the heteroaryl portion of heteroarylalkoxy and heteroarylcarbonylalkoxy can be optionally substituted with one, two, three, four, or five substituents independently selected from the group consisting of alkoxy, alkoxyalkoxy, alkoxyalkoxyalkoxy, alkyl, cyano, halo, haloalkylsulfonyloxy, haloalkoxy, haloalkyl, haloalkyl, hydroxyalkenyl, hydroxyalkoxy, hydroxyalkyl, hydroxyalkynyl, hydroxy, nitro, NR$^a$R$^b$, (NR R$^b$)alkoxy, (NR$^a$R$^b$)alkyl, and (NR$^a$R$^b$)alkynyl.

The term "heteroarylalkoxy," as used herein, refers to an alkoxy group substituted with at least one heteroaryl group.

The term "heteroarylalkyl," as used herein, refers to an alkyl group substituted with at least one heteroaryl group.

The term "heteroarylcarbonyl," as used herein, refers to a heteroaryl group attached to the parent molecular moiety through a carbonyl group.

The term "heteroarylcarbonylalkoxy," as used herein, refers to an alkoxy group substituted with heteroarylcarbonyl group.

The term "heteroarylsulfonyl," as used herein, refers to a heteroaryl group attached to the parent molecular moiety through a sulfonyl group The term "heterocycle" or "heterocyclic" as used herein, refers a monocyclic heterocyclic ring or a bicyclic heterocyclic ring. The monocyclic heterocyclic ring consists of a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a phenyl group or the monocyclic heterocyclic ring fused to a cycloalkyl group or the monocyclic heterocyclic ring fused to a cycloalkenyl group or the monocyclic heterocyclic ring fused to another monocyclic heterocyclic ring. Representative examples of the bicyclic heterocyclic ring include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocycles of this invention can be optionally substituted with one, two, or three substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, $NR^aR^b$ and $(NR^aR^b)$carbonyl.

The term "heterocyclealkoxy" as used herein, refers to a heterocycle group, as defined herein, appended to the parent molecular moiety through an alkoxy group, as defined herein.

The term "heterocycleoxy" as used herein, refers to a heterocycle group, as defined herein, attached to the parent molecular moiety through an oxygen atom.

The term "heterocycleoxyalkoxy" as used herein, refers to an alkoxy group, as defined herein, substituted with one heterocycleoxy group, as defined herein.

The term "heterocycleoxyalkyl" as used herein, refers to an alkyl group, as defined herein, substituted with one heterocycleoxy group, as defined herein.

The term "heterocycleoxyalkynyl" as used herein, refers to an alkynyl group, as defined herein, substituted with one heterocycleoxy group, as defined herein.

The term "hydroxy," as used herein, refers to —OH.

The term "hydroxyalkenyl," as used herien, refers to an alkenyl group substituted with at least one hydroxy group.

The term "hydroxyalkoxy," as used herien, refers to an alkoxy group substituted with at least one hydroxy group.

The term "hydroxyalkyl," as used herien, refers to an alkyl group substituted with at least one hydroxy group.

The term "hydroxyalkynyl," as used herien, refers to an alkynyl group substituted with at least one hydroxy group.

The term "nitro," as used herein, refers to —NO$_2$.

The term "$NR^aR^b$," as used herein, refers to two groups, $R^a$ and $R^b$, which are attached to the parent molecular moiety through a nitrogen atom. $R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl and $(NR^cR^d)$alkylcarbonyl.

The term "$(NR^aR^b)$alkoxy," as used herein, refers to an $NR^aR^b$ group attached to the parent molecular moiety through an alkoxy group.

The term "$(NR^aR^b)$alkyl," as used herein, refers to an alkyl group substituted with at least one $NR^aR^b$ group.

The term "$(NR^aR^b)$alkynyl," as used herein, refers to an alkynyl group substituted with at least one $NR^aR^b$ group.

The term "$(NR^aR^b)$carbonyl," as used herein, refers to an $NR^aR^b$ group attached to the parent molecular moiety through a carbonyl group.

The term "$(NR^aR^b)$carbonylalkoxy," as used herein, refers to an $(NR^aR^b)$carbonyl group attached to the parent molecular moiety through an alkoxy group.

The term "$(NR^aR^b)$carbonylalkyl," as used herein, refers to an alkyl group substituted with at least one $NR^aR^b$ group.

The term "$NR^cR^d$," as used herein, refers to two groups, $R^c$ and $R^d$, which are attached to the parent molecular moiety through a nitrogen atom. $R^c$ and $R^d$ are independently selected from the group consisting of hydrogen, alkyl, and cycloalkyl.

The term "$(NR^cR^d)$alkyl," as used herein, refers to an alkyl group substituted with at least one $NR^cR^d$ group.

The term "$(NR^cR^d)$alkylcarbonyl," as used herein, refers to an $(NR^cR^d)$alkyl group attached to the parent molecular moiety through a carbonyl group.

The term "oxo," as used herein, refers to =O.

The term sulfonyl, as used herein, refers to —SO$_2$—.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Because carbon-carbon double bonds exist in the present compounds, the invention contemplates various geometric isomers and mixtures thereof resulting from the arrangement of substituents around these carbon-carbon double bonds. It should be understood that the invention encompasses both isomeric forms (trans or cis), or mixtures thereof, which possess the ability to inhibit protein kinases. These substituents are designated as being in the E (trans) or Z (cis)

configuration wherein the term "E" represents higher order substituents on opposite sides of the carbon-carbon double bond, and the term "Z" represents higher order substituents on the same side of the carbon-carbon double bond.

When it is possible that, for use in therapy, therapeutically effective amounts of a compound of formula (I), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I) or therapeutically acceptable salts thereof, and one or more pharmaceutically acceptable carriers, diluents, or excipients. The compounds of formula (I) and therapeutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of formula (I), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, wasces, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an altenative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and therapeutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and therapeutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

Determination of Biological Activity

The Chk1 enzymatic assay was carried out using recombinant Chk1 kinase domain protein covering amino acids from residue 1 to 289 and a polyhistidine tag at the C-terminal end. Human cdc25c peptide substrate contained a sequence from amino acid residue 204 to 225. The reaction mixture contained 25 mM of HEPES at pH 7.4, 10 mM $MgCl_2$, 0.08 mM Triton X-100, 0.5 mM DTT, 5 µM ATP, 4 nM 33P ATP, 5 µM cdc25c peptide substrate, and 6.3 nM of the recombinant Chk1 protein. Compound vehicle DMSO was maintained at 2% in the final reaction. After 30 minutes at room temperature, the reaction was stopped by addition of equal volume of 4M NaCl and 0.1M EDTA, pH 8. A 40 µL aliquot of the reaction was added to a well in a Flash Plate (NEN Life Science Products, Boston, Mass.) containing 160 µL of phosphate-buffered saline (PBS) without calcium chloride and magnesium chloride and incubated at room temperature for 10 minutes. The plate was then washed 3 times in PBS with 0.05% of Tween-20 and counted in a Packard TopCount counter (Packard BioScience Company, Meriden, Conn.).

Compounds of the present invention inhibited Chk1 at $IC_{50}$ values between about 1 nM and about 5 µM. Preferred compounds inhibited Chk1 at $IC_{50}$ values between about 1 nM and about 25 nM. Thus, the compounds of the invention are useful in treating disorders which are caused or exacerbated by increased protein kinase levels.

| Chk1 Inhibition (nM) | | | | |
|---|---|---|---|---|
| 3 | 17 | 69 | 6 | 57 |
| 2 | 5 | 60 | 39 | 15 |
| 3 | 5 | 13 | 96 | 8.0 |
| 6 | 109 | 14 | 77 | 74.0 |
| 5 | 26 | 19 | 45 | 74.0 |
| 9 | 2 | 15 | 123 | 163.0 |
| 1 | 7 | 14 | 19 | 163.0 |
| 13 | 248 | 91 | 4 | 41 |
| 3 | 139 | 108 | 15 | 99 |
| 63 | 10 | 34 | 13 | 49 |
| 12 | 5 | 97 | 39 | 37 |
| 9 | 3 | 12 | 75 | 19 |
| 3 | 76 | 24 | 3 | 15 |
| 13 | 80 | 39 | 25 | 13 |
| 63 | 104 | 34 | 13 | 49 |
| 1 | 2 | 12 | 124 | 97.0 |
| 6 | 13 | 274 | 75 | 28 |
| 17 | 10 | | | |

The compounds of the invention, including not limited to those specified in the examples, possess the ability to inhibit protein kinases. As protein kinase inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Synthetic Methods

Abbreviations which have been used in the descriptions of the scheme and the examples that follow are: EtOAc for ethyl acetate; DMF for N,N-dimethylformamide; dppf for 1,1'-bis(diphenylphosphino)ferrocene; dba for dibenzylideneacetone THF for tetrahydrofuran; $PPh_3$ for triphenylphosphine; and DMSO for dimethylsulfoxide.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, $R^1$, $R^2$, $R^3$, X, Y, Z, m, and n are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

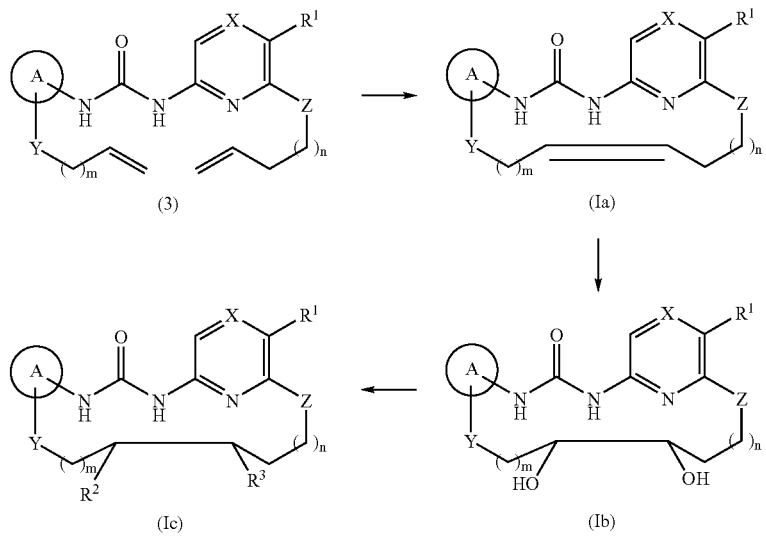

Scheme 1 shows the synthesis of compounds of formula (Ia), (Ib), and (Ic). Compounds of formula (3), which can be prepared by numerous methods known to those of ordinary skill in the art, can be converted to compounds of formula (Ia) by treatment with Grubbs' catalyst (first or second generation). Solvents typically used in this reaction include dichloromethane, chloroform, and methyl tert-butyl ether. The reaction is typically run at a temperature of about 50° C. to about 70° C. for about 12 to about 24 hours.

Compounds of formula (Ia) can be converted to compounds of formula (Ib) by treatment with an oxidizing agent such as $OsO_4$, $KMnO_4$, $H_2O_2$, N-methylmorpholine-N-oxide, and mixtures thereof. Examples of solvents used in these reactions include THF, water, 2-methyl-2-propanol, methyl tert-butyl ether, and mixtures thereof. The reaction is typically conducted at about 0° C. to about 30° C. for about 12 to about 24 hours.

The hydroxyl groups in the compounds of formula (Ib) can be converted to various other functional groups using methods known to those of ordinary skill in the art.

Scheme 2

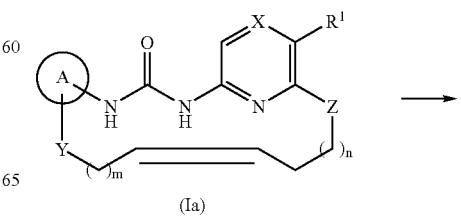

-continued

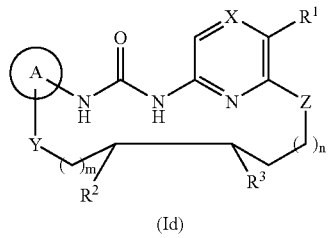

(Id)

As shown in Scheme 2, compounds of formula (Ia) can be converted to compounds of formula (Id) where $R^2$ and $R^3$ are hydrogen by hydrogenation using a metal catalyst in the presence of hydrogen. Representative palladium catalysts include Pd/C, RhCl(PPh$_3$)$_3$, and PtO$_2$. Examples of solvents used in these reactions include methanol, THF, ethanol, methyl tert-butyl ether, and mixtures thereof. The reaction is typically conducted at about 20° C. to about 40° C. for about 5 minutes to about 2 hours.

Compounds of formula (Ia) can be converted to compounds of formula (Id) where $R^2$ and $R^3$ are selected from the group consisting of hydroxy and NR$^a$R$^b$ by methods known to those of ordinary skill in the art. Compounds of formula (Id) where at least one of $R^2$ and $R^3$ is either hydroxy or NR$^a$R$^b$ can be further functionalized using methods known to those of ordinary skill in the art.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/Chem-Sketch version 5.03 (developed by Advanced Chemistry Development, Inc., Toronto, ON, Canada) or were given names consistent with ACD nomenclature.

EXAMPLE 1

18-chloro-11,14-dihydro-1H,10H-8,4-epiazeno-9,15,1,3,6-benzodioxatriazacycloheptadecin-2-one

EXAMPLE 1A 2-(allyloxy)-5-chloroaniline

A mixture of 2-amino-4-chlorophenol (10 g, 69.65 mmol) and K$_2$CO$_3$ (14.53 g, 105 mmol) in acetone (160 mL) was treated with allyl bromide (9.03 mL, 104 mmol), stirred at room temperature overnight, and filtered. The filter cake was washed with acetone and the combined filtrates were concentrated. The residue was purified by flash column chromatography eluting with hexanes/ethyl acetate (10:1) to provide 8.31 g (65%) of the desired product. MS (DCI/NH$_3$) m/z 184.02 (M+H)$^+$; $^1$H NMR (500 MHz, DMSO-d$_6$) δ 4.51 (m, 2H), 5.02 (s, 2H), 5.24 (dd, J=10.53, 1.68 Hz, 1H), 5.42 (m, 1H), 6.04 (m, 1H), 6.47 (dd, J=8.54, 2.44 Hz, 1H), 6.66 (d, J=2.75 Hz, 1H), 6.75 (d, J=8.54 Hz, 1H).

EXAMPLE 1B 1-(allyloxy)-4-chloro-2-isocyanatobenzene

A solution of 20% phosgene (5 mL, 47.3 mmol) in toluene (6 mL) at reflux was treated slowly with a solution of Example 1A (1 g, 5.44 mmol) in toluene (10 mL). The mixture was heated to reflux at 110° C. for 20 hours, cooled to room temperature, and concentrated to provide the desired product. $^1$H NMR (500 MHz, CD$_2$Cl$_2$) δ 4.62 (d, J=5.30 Hz, 2H), 5.33 (dd, J=10.76, 1.40 Hz, 1H), 5.46 (dd, J=17.31, 1.40 Hz, 1H), 6.07 (m, 1H), 6.84 (d, J=8.73 Hz, 1H), 6.99 (d, J=2.50 Hz, 1H), 7.10 (dd, J=8.74, 2.50 Hz, 1H).

EXAMPLE 1C 6-(3-butenyloxy)-2-pyrazinamine

A suspension of NaH (60%, 618 mg, 15.45 mmol) in dioxane (30 mL) at 0° C. was treated with 3-buten-1-ol (1.33 mL, 15.45 mmol), stirred for 2 hours, treated with 2-amino-6-chloropyrazine (1 g, 7.72 mmol), stirred at 100° C. for 2.5 days, cooled to room temperature, and diluted with ethyl acetate. The mixture was washed with water, dried (MgSO$_4$), filtered, and concentrated. The concentrate was purified by flash column chromatography eluting with hexanes/ethyl acetate (2:1) to provide the desired product (390 mg, 31%). MS (DCI/NH$_3$) m/z 166.12 (M+H)$^+$; $^1$H NMR (500 MHz, benzene-d$_6$) δ 2.66 (m, 2H), 4.42 (t, J=6.87 Hz, 2H), 5.24 (dd, J=10.22, 1.98 Hz, 1H), 5.30 (m, 1H), 6.04 (m, 1H), 7.64 (s, 1H), 7.65 (s, 1H).

EXAMPLE 1D

N-[2-(allyloxy)-5-chlorophenyl]-N'-[6-(3-butenyloxy)-2-pyrazinyl]urea

A mixture of Example 1B (201 mg, 0.96 mmol) and Example 1C (158 mg, 0.96 mmol) in toluene (15 mL) was stirred at 110° C. for 15 hours and concentrated. The concentrate was purified by flash column chromatography eluting with hexanes/ethyl acetate (1:1) to provide the desired product (185 mg, 52%). MS (DCI/NH$_3$) m/z 375.12 (M+H)$^+$; $^1$H NMR (500 MHz, DMSO-d$_6$) δ 2.52 (m, 2H), 4.33 (t, J=6.55 Hz, 2H), 4.70 (d, J=5.30 Hz, 2H), 5.09 (dd, J=10.29, 1.25 Hz, 1H), 5.16 (dd, J=17.31, 1.40 Hz, 1H), 5.31 (d, J=10.61 Hz, 1H), 5.43 (dd, J=17.16, 1.25 Hz, 1H), 5.88 (m, 1H), 6.08 (m, 1H), 7.02 (d, J=8.75 Hz, 1H), 7.06 (dd, J=8.75 Hz, 2.5 Hz, 1H), 7.89 (s, 1H), 8.22 (d, J=2.50 Hz, 1H), 8.69 (s, 1H), 9.07 (s, 1H), 10.08 (s, 1H).

EXAMPLE 1E 18-chloro-11,14-dihydro-1H,10H-8,4-epiazeno-9,15,1,3,6-benzodioxatriazacycloheptadecin-2-one A mixture of Example 1D (60 mg, 0.16 mmol) in CH$_2$Cl$_2$ (66 mL) was treated with the second generation Grubbs' catalyst (20 mg, 0.024 mmol), stirred at 50° C. overnight, and concentrated. The residue was purified by flash column chromatography eluting with hexanes/ethyl acetate (1:1) to provide the desired product (22 mg, 40%). MS (DCI/NH$_3$) m/z 347.11 (M+H)$^+$; $^1$H NMR (500 MHz, CD$_2$Cl$_2$) δ 2.70 (d, J=7.25 Hz, 2H), 4.63 (m, 4H), 6.05 (m, 2H), 6.90 (d, J=8.73 Hz, 1H), 7.02 (dd, J=8.73, 2.57 Hz, 1H), 7.15 (s, 1H), 7.72 (s, 1H), 7.84 (s, 1H), 8.25 (d, J=2.57 Hz, 1H), 10.55 (s, 1H).

EXAMPLE 2

18-chloro-11,12,13,14-tetrahydro-1H,10H-8,4-epiazeno-9,15,1,3,6-benzodioxatriazacycloheptadecin-2-one A suspension of Pt/C (10%, 2 mg) in 3:1 methanol/THF (3 mL) was treated with Example 1E (17 mg, 0.049 mmol). The reaction mixture was bubbled with hydrogen for 10 minutes and filtered through diatomaceous earth (Celite®). The filtrate was concentrated and the residue was purified by recrystallization from ethyl acetate to provide the desired product (13.7 mg, 80%). MS (DCI/NH$_3$) m/z 349.11 (M+H)$^+$; $^1$H NMR (500 MHz, DMSO-d$_6$) δ 1.64 (m, 2H), 1.84 (m, 2H), 1.89 (m, 2H), 4.14 (t, J=5.16 Hz, 2H), 4.48 (t, J=7.80 Hz, 2H), 7.08 (d, J=2.50 Hz, 1H), 7.09 (s, 1H), 7.89 (s, 1H), 7.95 (s, 1H), 8.23 (d, J=2.50 Hz, 1H), 10.26 (s, 1H), 10.32 (s, 1H).

EXAMPLE 3

18-chloro-12,13-dihydroxy-11,12,13,14-tetrahydro-1H,10H-8,4-epiazeno-9,15,1,3,6-benzodioxatriazacycloheptadecin-2-one A solution of Example 1E (20 mg, 0.081 mmol) and N-methylmorpholine-N-oxide (14 mg, 0.12 mmol) in THF (1.6 mL) and H$_2$O (0.2 mL) at 0° C. was treated with 2.5 wt % of OsO$_4$ in 2-methyl-2-propanol (0.065 mL), stirred overnight at room temperature, and filtered. The filter cake was washed with water and dried to provide the desired product (22 mg, 73%). MS (DCI/NH$_3$) m/z 381.1 (M+H)$^+$; $^1$H NMR (500 MHz, DMSO-d$_6$) δ 1.84 (m, 1H), 2.29 (m, 1H), 3.82 (m, 2H), 4.12 (m, 2H), 4.46 (m, 2H), 4.57 (m, 2H), 7.11 (dd, J=8.73 Hz, 2.50 Hz, 1H), 7.15 (d, J=9.05 Hz, 1H), 7.85 (s, 1H), 7.93 (s, 1H), 8.17 (d, J=2.81 Hz, 1H), 10.03 (s, 1H), 10.25 (s, 1H).

EXAMPLE 4

17-chloro-10,13-dihydro-1H-8,4-epiazeno-9,14,1,3,6-benzodioxatriazacyclohexadecin-2-one

EXAMPLE 4A 6-(allyloxy)-2-pyrazinamine

A mixture of allyl alcohol (0.21 mL, 3.08 mmol) in dioxane (4 mL) was treated with NaH (60%, 3.08 mmol), stirred for 30 minutes, treated with 2-amino-6-chloropyrazine (200 mg, 1.54 mmol), heated to 140° C. in a Smith Synthesizer for 2200 seconds, and filtered. The filtrate was concentrated and purified by flash column chromatography eluting with hexanes/ethyl acetate (2:1) to provide the desired product (133 mg, 57%). MS (DCI/NH$_3$) m/z 152.0 (M+H)$^+$; $^1$H NMR (500 MHz, CD$_2$Cl$_2$) δ 4.75 (m, 2H), 5.24 (m, 1H), 5.37 (m, 1H), 6.05 (m, 1H), 7.50 (s, 1H), 7.53 (s, 1H).

EXAMPLE 4B

N-[2-(allyloxy)-5-chlorophenyl]-N'-[6-(allyloxy)-2-pyrazinyl]urea

The desired product was prepared (650 mg, 66% yield) by substituting Example 4A for Example 1C in Example 1D. MS (DCI/NH$_3$) m/z 361.1 (M+H)$^+$; $^1$H NMR (400 MHz, DMSO-d$_6$) δ 4.69 (d, J=5.52 Hz, 2H), 4.82 (d, J=5.52 Hz, 2H), 5.28 (m, 2H), 5.38 (dd, J=8.29, 1.53 Hz, 1H), 5.43 (dd, J=8.13, 1.69 Hz, 1H), 6.07 (m, 2H), 7.01 (m, 1H), 7.05 (m, 1H), 7.93 (s, 1H), 8.21 (d, J=2.45 Hz, 1H), 8.69 (s, 1H), 9.07 (s, 1H), 10.08 (s, 1H).

EXAMPLE 4C 17-chloro-10,13-dihydro-1H-8,4-epiazeno-9,14,1,3,6-benzodioxatriazacyclohexadecin-2-one The desired product was prepared (144 mg, 56% yield) by substituting Example 4B for Example 1D in Example 1E. MS (DCI/NH$_3$) m/z 333.0 (M+H)$^+$; $^1$H NMR (500 MHz, DMSO-d$_6$) δ 4.70 (d, J=3.12 Hz, 2H), 5.44 (d, J=4.68 Hz, 2H), 5.82 (m, 2H), 7.08 (dd, J=8.73, 2.81 Hz, 1H), 7.17 (d, J=8.73 Hz, 1H), 7.85 (s, 1H), 7.91 (s, 1H), 8.33 (d, J=2.50 Hz, 1H), 10.31 (s, 1H), 11.04 (s, 1H).

EXAMPLE 5

17-chloro-10,11,12,13-tetrahydro-1H-8,4-epiazeno-9,14,1,3,6-benzodioxatriazacyclohexadecin-2-one The desired product was prepared (10 mg, 50% yield) by substituting Example 4C for Example 1E in Example 2. MS (DCI/NH$_3$) m/z 335.0 (M+H)$^+$; $^1$H NMR (500 MHz, DMSO-d$_6$) δ 1.85 (m, 2H), 2.01 (m, 2H), 4.16 (t, J=7.2 Hz, 2H), 4.64 (t, J=5.6 Hz, 2H), 7.04 (dd, J=8.58, 2.65 Hz, 1H), 7.14 (d, J=8.73 Hz, 1H), 7.84 (s, 1H), 7.92 (s, 1H), 8.34 (d, J=2.50 Hz, 1H), 10.28 (s, 1H), 10.99 (s, 1H).

EXAMPLE 6

17-chloro-11,12-dihydroxy-10,11,12,13-tetrahydro-1H-8,4-epiazeno-9,14,1,3,6-benzodioxatriazacyclohexadecin-2-one The desired product was prepared (21.7 mg, 70% yield) by substituting Example 4C for Example 1E in Example 3. MS (DCI/NH$_3$) m/z 367.0 (M+H)$^+$; $^1$H NMR (400 MHz, DMSO-d$_6$) δ 4.06 (m, 3H), 4.18 (m, 2H), 5.14 (d, J=25.8 Hz, 1H), 5.19 (t, J=6.5 Hz, 1H), 5.28 (d, J=6.5 Hz, 1H), 7.06 (dd, J=8.75, 2.61 Hz, 1H), 7.20 (d, J=8.90 Hz, 1H), 7.87 (s, 1H), 7.92 (s, 1H), 8.36 (d, J=2.76 Hz, 1H), 10.28 (s, 1H), 10.88 (s, 1H).

EXAMPLE 7

18-chloro-2-oxo-2,3,11,14-tetrahydro-1H,10H-8,4-epiazeno-9,15,1,3,6-benzodioxatriazacycloheptadecine-7-carbonitrile

EXAMPLE 7A 2-chloro-3-(dichloromethyl)pyrazine

A mixture of 2-chloro-3-methylpyrazine (10 g, 77.8 mmol), acetic acid (90 mL), and chlorine (23.6 g) were combined and heated at 100° C. for 3 hours, and concentrated. The residue was suspended in dichloromethane, washed with water and 5% NaHCO$_3$, dried (MgSO$_4$), filtered, and concentrated. The crude product was purified by flash column chromatography eluting with hexanes/ethyl acetate (3:1) to provide the desired product (3.8 g, 25%). MS (DCI/NH$_3$) m/z 197.0 (M+H)$^+$; $^1$H NMR (400 MHz, benzene-d$_6$) δ 7.70 (s, 1H), 8.67 (d, J=2.15 Hz, 1H), 8.83 (d, J=2.45 Hz, 1H).

EXAMPLE 7B 5-amino-3-chloro-2-pyrazinecarbaldehyde oxime

A solution of NH$_2$OH.HCl (7.04 g, 101.3 mmol) in H$_2$O (20 mL) and ethanol (20 mL) was buffered to pH 7.5 with 10M NaOH, treated with Example 7A (2 g, 10.13 mmol), heated to reflux at 95° C. for 6 hours, partially concentrated, and cooled to 0° C. overnight. The precipitate was collected by filtration and dried to provide the desired product (500 mg, 29%). MS (DCI/NH$_3$) M/z 173.0 (M+H)$^+$; $^1$H NMR (500 MHz, acetone-d$_6$) δ 7.26 (s, 2H), 7.88 (s, 1H), 8.15 (s, 1H), 11.40 (s, 1H).

EXAMPLE 7C 5-amino-3-chloro-2-pyrazinecarbaldehyde O-acetyloxime

A solution of Example 7B (450 mg, 2.60 mmol) in 1N NaOH (10 mL) was treated dropwise with acetic anhydride (1 mL) while maintaining the temperature of the reaction mixture at 20° C. The reaction mixture was stirred for 10 minutes and the precipitate was collected by filtration, washed with water, and dried to provide the desired product (460 mg, 82%). MS (DCI/NH$_3$) m/z 215.12.0 (M+H)$^+$; $^1$H NMR (400 MHz, DMSO-d$_6$) δ 2.19 (s, 3H), 7.69 (s, 2H), 7.96 (s, 1H), 8.57 (s, 1H).

EXAMPLE 7D 5-amino-3-chloro-2-pyrazinecarbonitrile

A suspension of Example 7C (460 mg, 2.14 mmol) in o-xylene (22 mL) was stirred at 160° C. for 20 hours, treated with charcoal (10 mg), and filtered. The filtrate was cooled to room temperature and the resulting precipitate was collected by filtration to provide the desired product (250 mg, 75%). MS (ESI) m/z 152.93 (M–H)—; $^1$H NMR (500 MHz, DMSO-d$_6$) δ 7.88 (s, 1H), 8.09 (s, 2H).

EXAMPLE 7E 5-amino-3-(3-butenyloxy)-2-pyrazinecarbonitrile

A suspension of NaH (60%, 52 mg, 1.3 mmol) in dioxane (3 mL) in a microwave vial was treated with 3-buten-1-ol (0.112 mL, 1.3 mmol), stirred at room temperature for 30 minutes, and treated with Example 7D (100 mg, 0.65 mmol). The resulting mixture was heated to 100° C. for 3000 seconds in a Smith Synthesizer, cooled, and concentrated. The residue was purified by flash column chromatography eluting with hexanes/ethyl acetate (1:1) to provide the desired product (74 mg, 60%). MS (DCI/NH$_3$) m/z 208.12 (M+NH$_4$)$^+$; $^1$H NMR (500 MHz, acetone-d$_6$) δ 2.49 (m, 2H), 4.35 (t, J=6.71 Hz, 2H), 5.09 (dd, J=10.22, 1.98 Hz, 1H), 5.15 (dd, J=17.09, 1.83 Hz, 1H), 5.85 (m, 1H), 7.51 (s, 1H), 7.66 (s, 2H).

EXAMPLE 7F phenyl 6-(3-butenyloxy)-5-cyano-2-pyrazinylcarbamate

A suspension of Example 7E (200 mg, 1.05 mmol) in pyridine (0.17 mL, 2.1 mmol) and CH$_2$Cl$_2$ (10 mL) at 0° C. was treated dropwise with phenyl chloroformate (0.145 mL, 2.1 mmol), stirred at room temperature for 3 hours, and directly applied to a flash column. The column was eluted with dichloromethane to provide the desired product (130 mg, 40%). MS (DCI/NH$_3$) m/z 328.13 (M+NH$_4$)$^+$; $^1$H NMR (500 MHz, DMSO-d$_6$) δ 2.56 (q, J=6.71 Hz, 2H), 4.49 (t, J=6.71 Hz, 2H), 5.11 (dd, J=10.22, 1.68 Hz, 1H), 5.19 (dd, J=17.24, 1.68 Hz, 1H), 5.88 (m, 1H), 7.27 (d, J=7.63 Hz, 2H), 7.31 (t, J=7.32 Hz, 1H), 7.47 (t, J=7.93 Hz, 2H), 8.73 (s, 1H), 11.62 (s, 1H).

EXAMPLE 7G

N-[2-(allyloxy)-5-chlorophenyl]-N'-[6-(3-butenyloxy)-5-cyano-2-pyrazinyl]urea

A mixture of Example 1A (108.8 mg, 0.59 mmol) and Example 7F (116 mg, 0.37 mmol) in toluene (10 mL) was heated to 90° C. for 24 hours and concentrated. The residue was purified by flash column chromatograghy eluting with hexanes/ethyl acetate (3:1) to provide the desired product (86 mg, 58%). MS (DCI/NH$_3$) m/z 400.09 (M+H)$^+$; $^1$H NMR (400 MHz, DMSO-d$_6$) δ 2.53 (q, J=6.65 Hz, 2H), 4.45 (t, J=6.60 Hz, 2H), 4.70 (m, 2H), 5.10 (dd, J=10.28, 1.99 Hz, 1H), 5.17 (m, 1H), 5.30 (m, 1H), 5.42 (m, 1H), 5.85 (m, 1H), 6.07 (m, 1H), 7.06 (d, J=2.15 Hz, 1H), 7.06 (s, 1H), 8.19 (d, J=2.15 Hz, 1H), 8.86 (s, 1H), 9.05 (s, 1H), 10.69 (s, 1H).

EXAMPLE 7H 18-chloro-2-oxo-2,3,11,14-tetrahydro-1H,10H-8,4-epiazeno-9,15,1,3,6-benzodioxatriazacycloheptadecine-7-carbonitrile The desired product was prepared (40 mg, 66% yield) by substituting Example 7G for Example 1D in Example 1E. MS (DCI/NH$_3$) m/z 389.09 (M+NH$_4$)$^+$; $^1$H NMR (500 MHz, DMSO-d$_6$) δ 2.71 (q, J=7.49 Hz, 2H), 4.68 (t, J=7.05 Hz, 2H), 4.70 (d, J=6.86 Hz, 2H), 6.02 (m, 1H), 6.09 (m, 1H), 7.12 (dd, J=8.89, 2.65 Hz, 1H), 7.22 (d, J=9.04 Hz, 1H), 7.98 (s, 1H), 8.12 (d, J=2.49 Hz, 1H), 10.35 (s, 1H), 10.97 (s, 1H).

EXAMPLE 8

18-chloro-2-oxo-2,3,11,12,13,14-hexahydro-1H,10H-8,4-epiazeno-9,15,1,3,6-benzodioxatriazacycloheptadecine-7-carbonitrile The desired product was prepared (7 mg, 70% yield) by substituting Example 7H for Example 1E in Example 2. MS (DCI/NH$_3$) m/z 391.3 (M+NH$_4$)$^+$; $^1$H NMR (500 MHz, DMSO-d$_6$) δ 1.61 (dd, J=12.16, 6.24 Hz, 2H), 1.82 (m, 2H), 1.95 (m, 2H), 4.19 (t, J=5.15 Hz, 2H), 4.62 (t, J=8.45 Hz, 2H), 7.13 (m, 2H), 7.99 (s, 1H), 8.20 (d, J=2.18 Hz, 1H), 9.95 (s, 1H), 10.94 (s, 1H).

EXAMPLE 9

18-chloro-12,13-dihydroxy-2-oxo-2,3,11,12,13,14-hexahydro-1H,10H-8,4-epiazeno-9,15,1,3,6-benzodioxatriazacycloheptadecine-7-carbonitrile The desired product was prepared (8.5 mg, 88% yield) by substituting Example 7H for Example 1E in Example 3. MS (ESI) m/z 404.01 (M–H)$^-$; $^1$H NMR (500 MHz, DMSO-d$_6$) δ 1.93 (m, 1H), 2.33 (m, 1H), 3.82 (m, 2H), 4.12 (m, 2H), 4.61 (m, 1H), 4.69 (m, 1H), 4.90 (d, J=4.99 Hz, 1H), 5.08 (d, J=4.99 Hz, 1H), 7.14 (dd, J=8.89, 2.34 Hz, 1H), 7.18 (d, J=9.05 Hz, 1H), 8.00 (s, 1H), 8.16 (d, J=2.49 Hz, 1H), 9.79 (s, 1H), 10.93 (s, 1H).

EXAMPLE 10

18-chloro-17-hydroxy-2-oxo-2,3,11,12,13,14-hexahydro-1H,10H-8,4-epiazeno-9,15,1,3,6-benzo-dioxatriazacycloheptadecine-7-carbonitrile

EXAMPLE 10A 2,5-dichloro-4-nitrophenol

To a solution of 2,5-dichlorophenol (10 g, 61.3 mmol) in $CCl_4$ (400 mL) at 0° C. was dropwise added 4.7 mL (73.6 mmol) of 70% $HNO_3$ in 30 mL of $CCl_4$ during 30 min. The reaction mixture was slowly warmed to room temperature and stirred for 1 hour. The yellow precipitate was collected by filtration and dried to give the desired product (8.4 g) at 62% yield. MS (DCI/$NH_3$) m/z 224.91 (M+$NH_4$)$^+$; $^1$H NMR (500 MHz, DMSO-$D_6$) δ ppm 7.17 (s, 1 H) 8.25 (s, 1 H) 12.12 (s, 1 H).

EXAMPLE 10B

{2-[(2,5-dichloro-4-nitrophenoxy)methoxy]ethyl}(trimethyl)silane

To a solution of Example 10A (2 g, 9.62 mmol) in $CH_2Cl_2$ (50 mL) was added SEMCl (2.04 mL, 11.54 mmol) and DIEA (diisopropylamine) (2.01 mL, 20.96 mmol). The reaction was stirred at room temperature for 1 hour and concentrated. The residue was suspended in ethyl acetate and washed with water. The organic layer was dried over $MgSO_4$ and evaporated to give the desired product. MS (DCI/$NH_3$) m/z 355.06 (M+$NH_4$)$^+$; $^1$H NMR (500 MHz, DMSO-$D_6$) δ ppm 0.00 (s, 6 H) 0.04 (s, 3 H) 0.92–0.96 (m, 2 H) 3.78–3.83 (m, 2 H) 5.56 (s, 2 H) 7.61 (s, 1 H) 8.36 (s, 1 H).

EXAMPLE 10C (2-{[5-(allyloxy)-2-chloro-4-nitrophenoxy]methoxy}ethyl)(trimethyl)silane To a suspension of NaH (95%, 717 mg, 28.38 mmol) in THF (40 mL) was added allylic alcohol (1.93 mL, 28.38 mmol). The resulting mixture was stirred at room temperature for 1 hour and then dropwise added to a solution of Example 10B (8 g, 23.65 mmol) in THF (60 mL). The reaction was stirred for 2 hours and concentrated. The residue was purified by flash chromatography eluting with 9% ethyl acetate in hexane. The desired product (4.7 g) was obtained at 55% yield. MS (DCI/$NH_3$) m/z 377.11 (M+$NH_4$)$^+$; $^1$H NMR (500 MHz, DMSO-$D_6$) δ ppm 0.00 (s, 9 H) 0.92–0.95 (m, 2 H) 3.77–3.83 (m, 2 H) 4.79 (d, J=5.30 Hz, 2 H) 5.34 (m, 1 H) 5.49 (m, 1 H) 5.52 (s, 2 H) 6.07 (m, 1 H) 7.13 (s, 1 H) 8.13 (s, 1 H).

EXAMPLE 10D 2-(allyloxy)-5-chloro-4-{[2-(trimethylsilyl)ethoxy]methoxy}aniline To a solution of Example 10C (1.33 g, 3.69 mol) and $SnCl_2$ (4.16 g, 18.47 mmol) in ethanol (120 mL) was added triethylamine (10 mL, 110.7 mmol). Large quantities of yellow precipitates were formed. The suspension was heated at 70° C. for 3 hours, cooled and filtered. The precipitates were washed with $CH_2Cl_2$, and the combined filtrate was concentrated. The residue was purified by flash chromatography eluting with 9% ethyl acetate in hexane. The desired product (0.5 g) was obtained in 47% yield. MS (DCI/$NH_3$) m/z 330.07 (M+H)$^+$; $^1$H NMR (500 MHz, DMSO-$D_6$) δ ppm 0.00 (s, 9 H) 0.88–0.92 (m, 2 H) 3.74–3.77 (m, 2 H) 4.53 (s, 1 H) 4.54 (s, 1 H) 4.64 (s, 2 H) 5.12 (s, 2 H) 5.26 (d, J=10.61 Hz, 1 H) 5.43 (dd, J=17.16, 1.25 Hz, 1 H) 6.05 (m, 1 H) 6.68 (s, 1 H) 6.77 (s, 1 H).

EXAMPLE 10E

N-(2-(allyloxy)-5-chloro-4-{[2-(trimethylsilyl)ethoxy]methoxy}phenyl)-N'-[6-(but-3-enyloxy)-5-cyanopyrazin-2-yl]urea A mixture of Example 7F (1.925 g, 6.21 mmol) and Example 10D (2.049 g, 6.21 mmol) in DMF (25 ml) was stirred at 70° C. for 6 hours. DMF was removed by evaporation, and the residue was suspended in a mixture of hexane and ethyl acetate. The precipitates were collected by filtration and dried on vacuum pump. The desired product (3 g, 88%) was obtained as white solid. MS (DCI/$NH_3$) m/z 546.18 (M+H)$^+$; $^1$H NMR (500 MHz, DMSO-$D_6$) δ ppm 0.00 (s, 9 H) 0.90–0.93 (m, 2 H) 2.56 (q, J=6.76 Hz, 2 H) 3.75–3.79 (m, 2 H) 4.47 (t, J=6.55 Hz, 2 H) 4.71 (d, J=5.30 Hz, 2 H) 5.13 (d, J=10.29 Hz, 1 H) 5.19 (dd, J=17.31, 1.72 Hz, 1 H) 5.31 (s, 2 H) 5.33 (dd, J=10.45, 1.40 Hz, 1 H) 5.46 (dd, J=17.31, 1.40 Hz, 1 H) 5.89 (m, 1 H) 6.09 (m, 1 H) 7.02 (s, 1 H) 8.13 (s, 1 H) 8.85 (s, 1 H) 8.94 (s, 1 H) 10.59 (s, 1 H).

EXAMPLE 10F 18-chloro-2-oxo-17-{[2-(trimethylsilyl)ethoxy]methoxy}-2,3,11,14-tetrahydro-1H,10H-8,4-epiazeno-9,15,1,3,6-benzodioxatriazacycloheptadecine-7-carbonitrile A mixture of Example 10E (2.87 g, 5.26 mmol) and Grubbs Catalyst (2$^{nd}$ generation, 439 mg, 0.526 mmol) in $CH_2Cl_2$ (3.5 L) was stirred at room temperature overnight, and then DMSO (7.46 mL, 105 mmol) was added. The reaction mixture was further stirred for 24 hours, and concentrated. The residue was purified by flash chromatography eluting with 9% of ethyl acetate in dichloromethane to provide the desired product (2.5 g, 92%). MS (DCI/$NH_3$) m/z 535.14 (M+$NH_4$)$^+$; $^1$H NMR (400 MHz, DMSO-$D_6$) δ ppm 0.00 (s, 9 H) 0.90–0.94 (m, 2 H) 2.73 (q, J=7.36 Hz, 2 H) 3.76–3.80 (m, 2 H) 4.66–4.73 (m, 4 H) 5.36 (s, 2 H) 5.99–6.14 (m, 2 H) 7.13 (s, 1 H) 7.99 (s, 1 H) 8.07 (s, 1 H) 10.24 (s, 1 H) 10.93 (s, 1 H).

EXAMPLE 10G 18-chloro-2-oxo-17-{[2-(trimethylsilyl)ethoxy]methoxy}-2,3,11,12,13,14-hexahydro-1H,10H-8,4-epiazeno-9,15,1,3,6-benzodioxatriazacycloheptadecine-7-carbonitrile A mixture of Example 10F (2 g, 3.86 mmol) and 10% Pd/C (160 mg, 0.151 mmol) in THF was stirred under hydrogen atmosphere for 3 hours, and the insoluble material was filtered off. The filtrate was concentrated, and the residue was purified by flash chromatography eluting with 9% of ethyl acetate in dichloromethane. The desired product (1.83 g, 91%) was obtained as white solid. MS (DCI/$NH_3$) m/z 537.20 (M+$NH_4$)$^+$; $^1$H NMR (500 MHz, DMSO-$D_6$) δ ppm 0.00 (s, 9 H) 0.90–0.94 (m, 2 H) 1.59–1.65 (m, 2 H) 1.83–1.87 (m, 2 H) 1.94–2.01 (m, 2 H) 3.77–3.80 (m, 2 H) 4.19–4.21 (m, 2 H) 4.60–4.63 (m, 2 H) 5.35 (s, 2 H) 7.05 (s, 1 H) 8.00 (s, 1 H) 8.17 (s, 1 H) 9.84 (s, 1 H) 10.90 (s, 1 H).

EXAMPLE 10H 18-chloro-17-hydroxy-2-oxo-2,3,11,12,13,14-hexahydro-1H,10H-8,4-epiazeno-9,15,1,3,6-benzodioxatriazacycloheptadecine-7-carbonitrile To a solution of Example 10G (1.8 g, 3.46 mmol) in a mixture of dichloromethane (100 mL) and ethanol (300 mL) was added 9 mL of 4 N HCl in 1,4-dioxane dropwise. The reaction mixture was stirred overnight, and the white precipitate was collected by filtration and dried. The desired product (1.3 g, 96%) was obtained as white solid. MS (DCI/NH$_3$) m/z 407.08 (M+NH$_4$)$^+$; $^1$H NMR (500 MHz, DMSO-D$_6$) δ ppm 1.60–1.65 (m, 2 H) 1.81–1.85 (m, 2 H) 1.94–2.00 (m, 2 H) 4.11 (t, J=5.15 Hz, 2 H) 4.59 (t, J=8.11 Hz, 2 H) 6.72 (s, 1 H) 7.99 (s, 1 H) 8.06 (s, 1 H) 9.75 (s, 1 H) 10.78 (s, 1 H).

EXAMPLE 11

18-chloro-17-(3-hydroxypropoxy)-2-oxo-2,3,11,12,13,14-hexahydro-1H,10H-8,4-epiazeno-9,15,1,3,6-benzodioxatriazacycloheptadecine-7-carbonitrile A mixture of Example 10H (20 mg, 0.051 mmol), 3-bromopropanol (11 mg, 0.077 mmol) and Cs$_2$CO$_3$ (33.4 mg, 0.102 mmol) in DMF (2 mL) was heated at 40° C. overnight. Inorganic salts were filtered off, and the filtrate was concentrated. The residue was purified by HPLC eluting with a gradient of 0%–70% of acetonitrile in 0.1% TFA aqueous solution. The desired product (8.2 mg, 36%) was obtained. MS (ESI) m/z 445.98 (M–H)$^-$; $^1$H NMR (500 MHz, DMSO-D$_6$) δ ppm 1.57–1.62 (m, 2 H) 1.80–1.84 (m, 2 H) 1.85–1.90 (m, 2 H) 1.93–1.99 (m, 2 H) 3.58 (q, J=5.90 Hz, 2 H) 4.15 (t, J=6.26 Hz, 2 H) 4.24 (t, J=5.03 Hz, 2 H) 4.56–4.61 (m, 3 H) 6.92 (s, 1 H) 7.99 (s, 1 H) 8.11 (s, 1 H) 9.79 (s, 1 H) 10.88 (s, 1 H).

EXAMPLE 12

18-chloro-17-(2,3-dihydroxypropoxy)-2-oxo-2,3,11,12,13,14-hexahydro-1H,10H-8,4-epiazeno-9,15,1,3,6-benzodioxatriazacycloheptadecine-7-carbonitrile A mixture of Example 10H (52 mg, 0.13 mmol), allyl bromide (0.0138 mL, 0.16 mmol) and K$_2$CO$_3$ (36.8 mg, 0.267 mmol) in DMF (5 mL) was stirred at room temperature overnight. Inorganic salts were filtered off, and the filtrate was concentrated. The residue was dissolved in a mixture of THF (20 mL) and water (2 mL), and the solution was treated with N-methylmorpholine-N-oxide (36 mg, 0.31 mmol), followed by the addition of 2.5% (W %) of OsO$_4$ in 2-methyl-2-propanol (0.19 mL) at 0° C. The reaction mixture was stirred overnight and concentrated. The residue was purified by HPLC eluting with the gradient of 0%-70% of acetonitrile in 0.1% TFA aqueous solution. The desired product (22 mg, 36%) was obtained as white solid. MS (ESI) m/z 462.20 (M–H)$^-$; $^1$H NMR (500 MHz, DMSO-D$_6$) δ ppm 1.57–1.62 (m, 2 H) 1.80–1.85 (m, 2 H) 1.92–1.99 (m, 2 H) 3.44–3.52 (m, 2 H) 3.82 (m, 1 H) 4.00 (m, 1 H) 4.08 (m, 1 H) 4.23 (t, J=5.19 Hz, 2 H) 4.58 (t, J=8.24 Hz, 2 H) 4.69 (t, J=5.65 Hz, 1 H) 4.98 (d, J=4.88 Hz, 1 H) 6.93 (s, 1 H) 7.98 (s, 1 H) 8.12 (s, 1 H) 9.79 (s, 1 H) 10.87 (s, 1 H).

EXAMPLE 13

18-chloro-17-(2-hydroxyethoxy)-2-oxo-2,3,11,12,13,14-hexahydro-1H,10H-8,4-epiazeno-9,15,1,3,6-benzodioxatriazacycloheptadecine-7-carbonitrile A mixture of Example 10H (30 mg, 0.077 mmol), 2-(2-bromoethoxy)tetrahydropyran (32 mg, 0.154 mmol) and Cs$_2$CO$_3$ (33.4 mg, 0.102 mmol) in DMF (2 mL) was heated at 40° C. overnight. Inorganic salts were filtered off, and the filtrate was concentrated. The residue was treated with HOAc/THF/H$_2$O (4:2:1, 8 mL) at 45° C. overnight. The solvent was removed, and the residue was purified by HPLC eluting with a gradient of 0%–70% of acetonitrile in 0.1% TFA aqueous solution. The desired product (25 mg, 76%) was obtained. MS (ESI) m/z 432.04 (M–H)$^-$; $^1$H NMR (400 MHz, DMSO-D$_6$) δ ppm 1.57–1.63 (m, 2 H) 1.80–1.85 (m, 2 H) 1.92–2.00 (m, 2 H) 3.74 (q, J=5.22 Hz, 2 H) 4.11 (t, J=5.06 Hz, 2 H) 4.23 (t, J=5.06 Hz, 2 H) 4.59 (t, J=8.29 Hz, 2 H) 4.88 (t, J=5.37 Hz, 1 H) 6.94 (s, 1 H) 7.99 (s, 1 H) 8.12 (s, 1 H) 9.80 (s, 1 H) 10.86 (s, 1 H).

Examples 14–26, shown in Table 1, were prepared using a similar procedure as described in Example 11 substituting 3-bromopropanol with the appropriate organic chloride or bromide.

TABLE 1

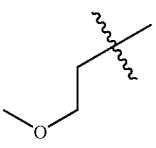

| Example | R | $^1$H NMR | MS | Yield |
|---|---|---|---|---|
| 14 | ![structure] | $^1$H NMR (400 MHz, DMSO-D$_6$) δ ppm 1.57–1.63(m, 2 H) 1.80–1.85(m, 2H) 1.92–1.99(m, 2 H) 3.34(s, 3 H) 3.68–3.70(m, 2H) 4.20–4.25(m, 4H) 4.59 (d, J=7.98 Hz, 2H) 6.93(s, 1H) 7.99(s, 1H) 8.13(s, 1H) 9.80 (s, 1H) 10.86(s, 1H) | ESI 446.1 (M – H)$^-$ | 15.9 mg 69% |

TABLE 1-continued

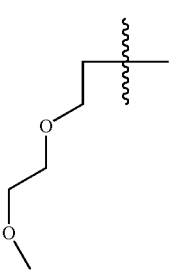

| Example | R | ¹H NMR | MS | Yield |
|---|---|---|---|---|
| 15 | 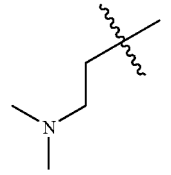 | ¹H NMR(400 MHz, DMSO-D₆) δ ppm 1.57–1.63(m, 2H) 1.80–1.85(m, 2H) 1.92–1.99(m, 2H) 3.25(s, 3H) 3.45–3.48(m, 2H) 3.61–3.63(m, 2H) 3.76 (d, J=4.60 Hz, 2H) 4.21–4.25 (m, 4 H) 4.60(t, J=8.29 Hz, 2H) 6.95(s, 1H) 7.99(s, 1H) 8.13 (s, 1H) 9.80(s, 1H) 10.86(s, 1 H) | ESI 490.07 (M − H)⁻ 492.07 (M + H)⁺ | 20.7 mg 82% |
| 16 | 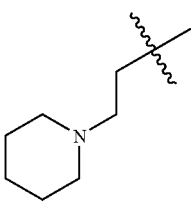 | ¹H NMR(400 MHz, DMSO-D₆) δ ppm 1.57–1.64(m, 2H) 1.80–1.88(m, 2H) 1.93–2.00(m, 2H) 2.93(s, 3H) 3.17(s, 3H) 3.55–3.58(m, 2H) 4.24–4.27 (m, 2H) 4.44(t, J=4.91 Hz, 2H) 4.60(t, J=8.29 Hz, 2H) 7.01(s, 1H) 8.00(s, 1H) 8.18(s, 1H) 9.84(s, 1H) 10.90(s, 1H) | ESI 459.14 (M − H)⁻ 461.07 (M + H)⁺ | 8.3 mg 35% |
| 17 | 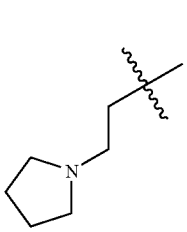 | ¹H NMR(400 MHz, DMSO-D₆) δ ppm 1.34–1.47(m, 2H) 1.56–1.64(m, 2H) 1.65–1.73(m, 2H) 1.81–1.89(m, 4H) 1.93–2.01(m, 2H) 3.04–3.13(m, 2H) 3.36–3.51(m, 2H) 3.60–3.72(m, 2H) 4.24–4.27(m, 2H) 4.44–4.46(m, 2H) 4.60(t, J=7.98 Hz, 2H) 7.00(s, 1H) 8.00(s, 1H) 8.18(s, 1H) 9.37 (s, 1H) 9.84(s, 1H) 10.90(s, 1 H) | ESI 499.11 (M − H)⁻ 501.13 (M + H)⁺ | 5.6 mg 22% |
| 18 | 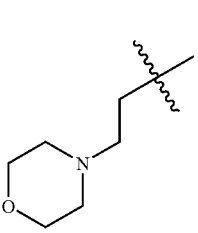 | ¹H NMR(400 MHz, DMSO-D₆) δ ppm 1.56–1.64(m, 2H) 1.80–1.87(m, 2H) 1.87–1.93(m, 2H) 1.95–1.99(m, 2H) 2.00–2.11(m, 2H) 3.18–3.27(m, 2H) 3.63–3.73(m, 4H) 4.23–4.28(m, 2H) 4.39–4.42(m, 2H) 4.57–4.64(m, 2H) 7.00(s, 1H) 8.00(s, 1H) 8.18(s, 1H) 9.84(s, 1H) 10.90(s, 1H) | ESI 485.09 (M − H)⁻ 487.07 (M + H)⁺ | 7.2 mg 29% |
| 19 | | ¹H NMR(400 MHz, DMSO-D₆) δ ppm 1.56–1.65(m, 2H) 1.80–1.88(m, 2H) 1.92–2.01(m, 2H) 3.33–3.42(m, 2H) 3.50–3.76(m, 6H) 3.96–4.09(m, 2H) 4.23–4.28(m, 2H) 4.40–4.49(m, 2H) 4.60(t, J=8.13 Hz, 2H) 7.00(s, 1H) 8.00(s, 1H) 8.17(s, 1H) 9.83(s, 1H) 9.94 (s, 1H) 10.89(s, 1H) | ESI 501.05 (M − H)⁻ | 7.7 mg 30% |

TABLE 1-continued

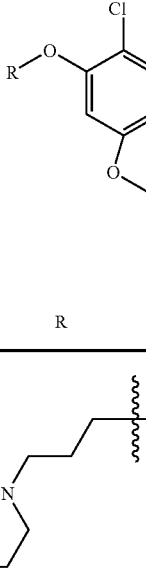

| Example | R | ¹H NMR | MS | Yield |
|---|---|---|---|---|
| 20 | 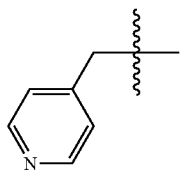 | ¹H NMR(400 MHz, DMSO-D₆) δ ppm 1.56–1.63(m, 2H) 1.80–1.87(m, 2H) 1.91–1.99(m, 2H) 2.11–2.19(m, 2H) 3.43–3.54(m, 4H) 3.57–3.70(m, 4H) 3.96–4.05(m, 2H) 4.16–4.19(m, 2H) 4.23–4.25(m, 2H) 4.58–4.62(m, 2H) 6.94(s, 1H) 8.00(s, 1H) 8.14(s, 1H) 9.82(s, 1H) 10.88(s, 1H) | ESI 515.11 (M − H)⁻ 517.07 (M + H)⁺ | 6.6 mg 25% |
| 21 | 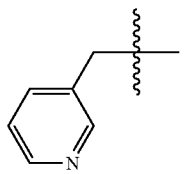 | ¹H NMR(400 MHz, DMSO-D₆) δ ppm 1.55–1.62(m, 2H) 1.78–1.84(m, 2H) 1.91–1.99(m, 2H) 4.20–4.23(m, 2H) 4.57–4.61(m, 2H) 5.41(s, 2H) 7.03 (s, 1H) 7.66(d, J=6.14 Hz, 2H) 7.99(s, 1H) 8.18(s, 1H) 8.72 (d, J=6.44 Hz, 2H) 9.81(s, 1H) 10.88(s, 1H) | ESI 479.02 (M − H)⁻ 481.05 (M + H)⁺ | 20.2 mg 82% |
| 22 | 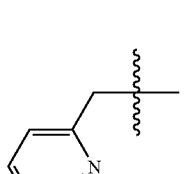 | ¹H NMR(400 MHz, DMSO-D₆) δ ppm 1.56–1.63(m, 2H) 1.79–1.85(m, 2H) 1.91–2.00(m, 2H) 4.24(t, J=5.06 Hz, 2H) 4.59 (t, J=7.67 Hz, 2H) 5.29(s, 2H) 7.08(s, 1H) 7.45(dd, J=7.83, 4.14 Hz, 1H) 7.88(m, 1H) 7.97 (s, 1H) 8.15(s, 1H) 8.56(dd, J=4.76, 1.69 Hz, 1H) 8.69(d, J=2.15 Hz, 1H) 9.81(s, 1H) 10.86(s, 1H) | ESI 481.05 (M − H)⁻ 479.07 (M + H)⁺ | 18 mg 73% |
| 23 | 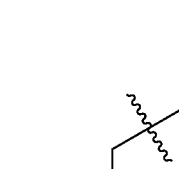 | ¹H NMR(500 MHz, DMSO-D₆) δ ppm 1.59–1.64(m, 2H) 1.83–1.87(m, 2H) 1.96–2.02(m, 2H) 4.26(t, J=5.19 Hz, 2H) 4.63 (t, J=8.24 Hz, 2H) 5.36(s, 2H) 7.12(s, 1H) 7.42(dd, J=7.17, 5.03 Hz, 1H) 7.64(d, J=7.63 Hz, 1H) 7.92–7.95(m, 1H) 8.03(s, 1H) 8.20(s, 1H) 8.64 (d, J=4.58 Hz, 1H) 9.85(s, 1H) 10.94(s, 1H) | ESI 481.03 (M − H)⁻ 479.03 (M + H)⁺ | 21.2 mg 86% |
| 24 | | ¹H NMR(400 MHz, DMSO-D₆) δ ppm 1.52–1.59(m, 2H) 1.71–1.78(m, 2H) 1.90–1.97(m, 2H) 4.13(t, J=5.22 Hz, 2H) 4.58 (t, J=8.29 Hz, 2H) 5.87(s, 2H) 6.91(s, 1H) 7.72–7.76(m, 1H) 7.97–8.00(m, 2H) 8.04–8.09(m, 1H) 8.15(s, 1H) 8.77 (d, J=3.99 Hz, 1H) 9.80(s, 1H) 10.87(s, 1H) | ESI 507.01 (M − H)⁻ | 22.2 mg 85% |

TABLE 1-continued

| Example | R | ¹H NMR | MS | Yield |
|---|---|---|---|---|
| 25 | (imidazolylethyl group) | ¹H NMR(400 MHz, DMSO-D₆) δ ppm 1.53–1.65(m, 2H) 1.79–1.87(m, 2H) 1.90–2.00(m, 2H) 4.23(t, J=4.60 Hz, 2H) 4.47 (t, J=5.06 Hz, 2H) 4.57–4.64 (m, 4H) 6.94(s, 1H) 7.61(s, 1H) 7.73(s, 1H) 7.99(s, 1H) 8.12(s, 1H) 8.96(s, 1H) 9.81 (s, 1H) 10.88(s, 1H) | ESI 482.03 (M − H)⁻ 484.00 (M + H)⁺ | 7.7 mg 31% |
| 26 | (isobutyl group) | ¹H NMR(500 MHz, DMSO-D₆) δ ppm 1.28(d, J=6.10 Hz, 6 H) 1.56–1.62(m, 2H) 1.79–1.84 (m, 2H) 1.92–1.99(m, 2H) 4.22(t, J=5.19 Hz, 2H) 4.59(t, J=8.24 Hz, 2H) 4.66–4.71(m, 1H) 6.92(s, 1H) 7.99(s, 1H) 8.12(s, 1H) 9.80(s, 1H) 10.89 (s, 1H) | ESI 429.97 (M − H)⁻ 432.00 (M + H)⁺ | 19.9 90% |

EXAMPLE 27

17-amino-18-chloro-2-oxo-2,3,11,12,13,14-hexahydro-1H,10H-8,4-epiazeno-9,15,1,3,6-benzodioxatriazacycloheptadecine-7-carbonitrile

EXAMPLE 27A 2-(allyloxy)-5-chloro-4-nitroaniline

To a mixture of 2-amino-4-chloro-5-nitrophenol (10 g, 0.053 mol) and allyl bromide (5.05 mL, 0.058 mol) in DMF (100 mL) was added K₂CO₃. The reaction mixture was stirred at room temperature for 3 hours, and then the inorganic salts were filtered off. The filtrate was concentrated, and the residue was dissolved in ethyl acetate and washed with aqueous NH₄Cl. The organic layer was dried over MgSO₄ and concentrated to provide the desired product (10.9 g, 90%) as yellow solid. MS (DCI/NH₃) m/z 246.04 (M+NH₄)⁺; ¹H NMR (500 MHz, DMSO-D₆) δ ppm 4.68 (d, J=4.99 Hz, 2 H) 5.29 (dd, J=10.60, 1.56 Hz, 1 H) 5.48 (dd, J=17.47, 1.56 Hz, 1 H) 6.05 (m, 1 H) 6.48 (s, 2 H) 6.76 (s, 1 H) 7.59 (s, 1 H).

EXAMPLE 27B

N-[2-(allyloxy)-5-chloro-4-nitrophenyl]-N'-[6-(but-3-enyloxy)-5-cyanopyrazin-2-yl]urea A mixture of Example 27A (10.62 g, 46.45 mmol) and Example 7F (12 g, 38.71 mmol) in DMF (150 mL) was heated at 80° C. for 40 hours. The solvent was removed, and the residue was triturated with ethyl acetate to provide the desired product (16 g, 93%). MS (DCI/NH₃) m/z 462.1 (M+NH₄)⁺; ¹H NMR (500 MHz, DMSO-D₆) δ ppm 2.31 (q, J=6.76 Hz, 2 H) 4.22 (t, J=6.71 Hz, 2 H) 4.61 (d, J=5.30 Hz, 2 H) 4.88 (d, J=10.29 Hz, 1 H) 4.94 (dd, J=17.31, 1.72 Hz, 1 H) 5.13 (dd, J=10.45, 1.40 Hz, 1 H) 5.24 (dd, J=17.47, 1.56 Hz, 1 H) 5.64 (m, 1 H) 5.85 (m, 1 H) 7.56 (s, 1 H) 8.25 (s, 1 H) 8.66 (s, 1 H) 9.11 (d, J=1.56 Hz, 1 H) 10.58 (s, 1 H).

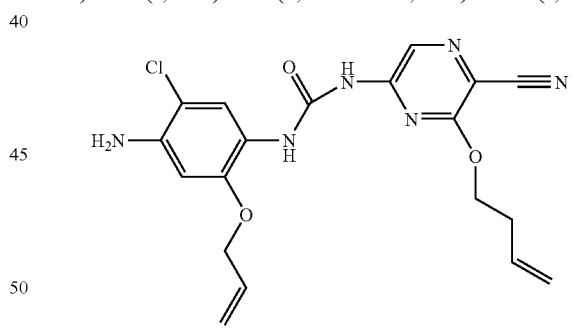

EXAMPLE 27C

N-[2-(allyloxy)-4-amino-5-chlorophenyl]-N'-[6-(but-3-enyloxy)-5-cyanopyrazin-2-yl]urea A mixture of Example 27B (3.5 g, 7.86 mmol), iron powder (4.4 g, 78.65 mmol) and NH₄Cl (210 mg, 3.93 mmol) in ethanol (80 mL) and water (20 mL) was heated at 80° C. for 8 hours. The insoluble material was filtered off, and the filtrate was concentrated. The residue was purified by flash chromatography eluting with 6% ethyl acetate in dichloromethane. The desired product (2.3 g, 70.6%) was obtained as yellow solid. MS (DCI/NH₃) m/z 415.08 (M+H)⁺; ¹H NMR (500 MHz, DMSO-D₆) δ ppm 2.51–2.57

(m, 5 H) 4.45 (t, J=6.56 Hz, 2 H) 4.57 (d, J=5.19 Hz, 2 H) 5.11 (dd, J=10.37, 1.83 Hz, 1 H) 5.15–5.19 (m, 3 H) 5.30 (dd, J=10.68, 1.53 Hz, 1 H) 5.43 (dd, J=17.39, 1.53 Hz, 1 H) 5.87 (m, 1 H) 6.07 (m, 1 H) 6.53 (s, 1 H) 7.82 (s, 1 H) 8.74 (s, 1 H) 8.80 (s, 1 H) 10.48 (s, 1 H).

EXAMPLE 27D 17-amino-18-chloro-2-oxo-2,3,11,14-tetrahydro-1H, 10H-8,4-epiazeno-9,15,1,3,6-benzodioxatriazacyclo-heptadecine-7-carbonitrile A mixture of Example 27C (2.93 g, 7.06 mmol) and Grubbs Catalyst (2$^{nd}$ generation) (0.6 g, 0.71 mmol) in dichloromethane (3.6 L) was stirred at room temperature overnight, and then DMSO (10 mL, 141 mmol) was added. The resulting mixture was further stirred 24 hours and concentrated. The residue was purified by flash chromatography eluting with 9% ethyl acetate in dichloromethane to provide the desired product (2.1 g, 77%) as yellow solid. MS (DCI/NH$_3$) m/z 404.08 (M+NH$_4$)$^+$; $^1$H NMR (500 MHz, DMSO-D$_6$) δ ppm 2.71 (q, J=7.70 Hz, 2 H) 4.58 (d, J=6.86 Hz, 2 H) 4.65 (t, J=7.64 Hz, 2 H) 5.17 (s, 2 H) 5.95–6.07 (m, 2 H) 6.64 (s, 1 H) 7.81 (s, 1 H) 7.96 (s, 1 H) 10.10 (s, 1 H) 10.79 (s, 1 H).

EXAMPLE 27E 17-amino-18-chloro-2-oxo-2,3,11,12,13,14-hexahydro-1H,10H-8,4-epiazeno-9,15,1,3,6-benzodioxatriazacycloheptadecine-7-carbonitrile A mixture of Example 27D (1 g, 2.58 mmol) and 10% Pd/C (50 mg, 0.047 mmol) in THF (250 ml) was stirred under hydrogen atmosphere at room temperature overnight. Insoluble material was filtered off, and the filtrate was concentrated. The residue was purified by flash chromatography eluting with 16% ethyl acetate in dichloromethane to provide the desired product (0.8 g, 80%) as orange solid. MS (DCI/NH$_3$) m/z 406.11 (M+NH$_4$)$^+$; $^1$H NMR (500 MHz, DMSO-D$_6$) δ ppm 1.54–1.59 (m, 2 H) 1.76–1.81 (m, 2 H) 1.90–1.96 (m, 2 H) 4.05 (d, J=5.49 Hz, 2 H) 4.55 (t, J=8.24 Hz, 2 H) 5.19 (s, 2 H) 6.56 (s, 1 H) 7.87 (s, 1 H) 7.95 (s, 1 H) 9.64 (s, 1 H) 10.76 (s, 1 H).

EXAMPLE 28

18-chloro-2-oxo-17-[(pyridin-3-ylmethyl)amino]-2, 3,11,12,13,14-hexahydro-1H,10H-8,4-epiazeno-9, 15,1,3,6-benzodioxatriazacycloheptadecine-7-carbonitrile To a solution of Example 27E (20 mg, 0.0514 mmol) in THF (3 mL) at 0° C. was added a fresh mixture (Mixture A) of 3-pyridine carboxylaldehyde (0.022 mL), 3 M H$_2$SO$_4$ (0.203 mL) and methanol (1 mL), followed by the addition of NaBH$_4$ (4 mg, 0.11 mmol). The reaction mixture was stirred at 0° C. for 30 minutes and monitored by LC-MS. The addition of Mixture A and NaBH$^4$ was repeated until the reaction completed. Saturated NaHCO$^3$ was added to adjust the pH>7. The precipitates were collected, washed with water thoroughly, and purified by reverse phase HPLC eluting with the gradient of 0%–70% of acetonitrile in 0.1% TFA aqueous solution. The desired product was obtained in 90% yield. MS (DCI/NH$^3$) m/z 480.11 (M+H)$^+$; $^1$H NMR (500 MHz, DMSO-D$^6$) δ ppm 1.45–1.50 (m, 2 H) 1.64–1.69 (m, 2 H) 1.86–1.92 (m, 2 H) 4.01 (t, J=5.30 Hz, 2 H) 4.47 (d, J=6.24 Hz, 2 H) 4.50 (t, J=8.11 Hz, 2 H) 6.01 (t, J=6.40 Hz, 1 H) 6.33 (s, 1 H) 7.33 (dd, J=7.49, 4.37 Hz, 1 H) 7.75–7.77 (m, 1 H) 7.84 (s, 1 H) 7.97 (s, 1 H) 8.43 (dd, J=4.68, 1.56 Hz, 1 H) 8.61 (d, J=1.87 Hz, 1 H) 9.60 (s, 1 H) 10.75 (s, 1 H).

EXAMPLE 29

18-chloro-2-oxo-117-[(pyridin-4-ylmethyl)amino]-2, 3,11,12,13,14-hexahydro-1H,10H-8,4-epiazeno-9, 15,1,3,6-benzodioxatriazacycloheptadecine-7-carbonitrile;

The desired product was prepared using a similar procedure described in Example 28 by substituting 3-pyridine carboxylaldehyde with 4-pyridine carboxylaldehyde. MS (ESI) m/z 480.12 (M+H)$^+$, 478.15 (M–H)$^-$; $^1$H NMR (300 MHz, DMSO-D$^6$) δ ppm 1.42–1.53 (m, 2 H) 1.58–1.70 (m, 2 H) 1.84–1.95 (m, 2 H) 3.96 (t, J=4.75 Hz, 2 H) 4.53 (t, J=8.81 Hz, 2 H) 4.60 (d, J=4.07 Hz, 2 H) 6.23 (s, 1 H) 6.28 (s, br, 1 H) 7.60 (s, 1 H) 7.61 (s, 1 H) 7.96 (s, 2 H) 8.62 (s, 1 H) 8.64 (s, 1 H) 9.63 (s, 1 H) 10.79 (s, 1 H).

EXAMPLE 30

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-2-carboxamide To a solution of Example 27E (10 mg, 0.026 mmol) and pyridine (1 mL) in dichloromethane (5 mL) was added pyridine-2-carbonyl chloride hydrochloric salt (20.7 mg, 0.12 mmol). The reaction mixture was stirred at room temperature for 2 days. The precipitates were collected by filtration and washed with methanol to provide the desired product (9.7 mg, 76%). MS (DCI/NH$^3$) m/z 494.15 (M+H)$^+$; $^1$H NMR (400 MHz, DMSO-D$^6$) δ ppm 1.61–1.70 (m, 2 H) 1.84–1.91 (m, 2 H) 1.94–2.01 (m, 2 H) 4.20–4.26 (m, 2 H) 4.63 (t, J=8.29 Hz, 2 H) 7.73 (m, 1 H) 8.01 (s, 1 H) 8.12 (m, 1 H) 8.20 (m, 1 H) 8.26 (s, 1 H) 8.33 (s, 1 H) 8.77 (d, J=4.30 Hz, 1 H) 9.96 (s, 1 H) 10.56 (s, 1 H) 10.96 (s, 1 H).

EXAMPLE 31

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-4-carboxamide The desired product (10 mg, 78%) was prepared by using a similar procedure described in Example 30. MS (ESI) m/z 494.11 (M+H)$^+$, 492.12 (M–H)$^-$; $^1$H NMR (400 MHz, DMSO-D$^6$) δ ppm 1.58–1.67 (m, 2 H) 1.80–1.87 (m, 2 H) 1.93–2.01 (m, 2 H) 4.19 (dd, J=5.68, 4.76 Hz, 2 H) 4.63 (t, J=8.29 Hz, 2 H) 7.37 (s, 1 H) 7.89 (d, J=5.52 Hz, 2 H) 8.01 (s, 1 H) 8.32 (s, 1 H) 8.79–8.81 (m, 2 H) 9.98 (s, 1 H) 10.34 (s, 1 H) 10.97 (s, 1 H).

EXAMPLE 32, 2-chloro-N-(18-chloro-7-cyano-2-oxo-2,3,11,12,13, 14-hexahydro-1H,10H-8,4-epiazeno-9,15,1,3,6-benzodioxatriazacycloheptadecin-17-yl)isonicotinamide To a suspension of Example 27E (34.5 mg, 0.089 mmol) in dichloromethane (4 mL) under N$^2$ was added anhydrous pyridine (1 mL), followed by the addition of 2-chloro-isonicotinyl chloride (31.2 mg, 0.18 mmol) in dichloromethane (1 mL). The reaction mixture was stirred at room temperature overnight, and the solvent and pyridine were removed using vacuum pump. Then saturated NaHCO$^3$ solution (3 mL) was added. The precipitate was ultrasonicated, filtered, washed with methanol (2 mL×3), and dried to give the title compound (13.9 mg, 30%). MS (ESI) m/z 526.00 (M−H)$^-$; $^1$H NMR (500 MHz, DMSO-D$^6$) δ ppm 1.58–1.68 (m, 2 H) 1.80–1.87 (m, 2 H) 1.93–2.02 (m, 2 H) 4.16–4.21 (m, 2 H) 4.60–4.66 (m, 2 H) 7.37 (s, 1 H) 7.89 (d, J=5.30 Hz, 1 H) 7.99 (s, 1 H) 8.02 (s, 1 H) 8.32 (s, 1 H) 8.64 (d, J=4.99 Hz, 1 H) 9.99 (s, 1 H) 10.45 (s, 1 H) 10.97 (s, 1 H).

EXAMPLE 33

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-3-carboxamide The title compound (13 mg, 51%) was synthesized using a similar procedure described in Example 32 by replacing 2-chloro-isonicotinyl chloride with nicotinoyl chloride. MS (ESI) m/z 491.98 (M−H)$^-$; $^1$H NMR (300 MHz, DMSO-D$^6$) δ ppm 1.57–1.69 (m, 2 H) 1.77–1.89 (m, 2 H) 1.91–2.03 (m, 2 H) 4.15–4.23 (m, 2 H) 4.59–4.69 (m, 2 H) 7.39 (s, 1 H) 7.59 (dd, J=8.14, 5.09 Hz, 1 H) 8.02 (s, 1 H) 8.29–8.36 (m, 2 H) 8.78 (dd, J=4.92, 1.86 Hz, 1 H) 9.14 (d, J=1.36 Hz, 1 H) 9.98 (s, 1 H) 10.29 (s, 1 H) 10.99 (s, 1 H).

EXAMPLE 34

N-(18-chloro-7-cyano-2-oxo-2,3,11,12,13,14-hexahydro-1H,10H-8,4-epiazeno-9,15,1,3,6-benzodioxatriazacycloheptadecin-17-yl)acetamide To a mixture of Example 27E (10 mg, 0.026 mmol) and pyridine (1 mL) in dichloromethane (10 mL) was added acetyl chloride (0.011 mL, 0.154 mmol) dropwise. The reaction mixture was stirred for 3 hours, and methanol (1 mL) was added to quench the reaction. The resulting mixture was concentrated, and the residue was triturated with a mixture of dichloromethane and methanol to provide the desired product (9.8 mg, 89%) as off-white solid. MS (DCI/NH$^3$) m/z 430.96 (M+H)$^+$, 429.01 (M−H)$^-$; $^1$H NMR (400 MHz, DMSO-D$^6$) δ ppm 1.58–1.64 (m, 2 H) 1.78–1.84 (m, 2 H) 1.90–1.99 (m, 2 H) 2.08 (s, 3 H) 4.11–4.14 (m, 2 H) 4.60 (t, J=8.29 Hz, 2 H) 7.50 (s, 1 H) 7.99 (s, 1 H) 8.22 (s, 1 H) 9.45 (s, 1 H) 9.91 (s, 1 H) 10.91 (s, 1 H).

EXAMPLE 35

N-(18-chloro-7-cyano-2-oxo-2,3,11,12,13,14-hexahydro-1H,10H-8,4-epiazeno-9,15,1,3,6-benzodioxatriazacycloheptadecin-17-yl)-2-(dimethylamino)acetamide The desired product was prepared using a similar procedure described in Example 34 by substituting acetyl chloride with 2-dimethylacetyl chloride. MS (ESI) m/z 474.10 (M+H)$^+$, 472.02 (M−H)$^-$; $^1$H NMR (400 MHz, DMSO-D$^6$) δ ppm 1.60–1.66 (m, 2 H) 1.80–1.87 (m, 2 H) 1.93–2.00 (m, 2 H) 2.87 (s, 6 H) 4.15–4.17 (m, 4 H) 4.62 (t, J=7.98 Hz, 2 H) 7.47 (s, 1 H) 8.01 (s, 1 H) 8.29 (s, 1 H) 9.81 (s, 1 H) 9.96 (s, 1 H) 10.24 (s, 1 H) 10.97 (s, 1 H).

EXAMPLE 36

N-(18-chloro-7-cyano-2-oxo-2,3,11,12,13,14-hexahydro-1H,10H-8,4-epiazeno-9,15,1,3,6-benzodioxatriazacycloheptadecin-17-yl)-3-(cyclopentylamino)propanamide

EXAMPLE 36A 3-chloro-N-(18-chloro-7-cyano-2-oxo-2,3,11,12,13,14-hexahydro-1H,10H-8,4-epiazeno-9,15,1,3,6-benzodioxatriazacycloheptadecin-17-yl)propanamide To a mixture of Example 27E (50 mg, 0.13 mmol) and pyridine (5 mL) in dichloromethane (25 mL) was dropwise added 3-chloropropionyl chloride (0.037 mL, 0.39 mmol) at 0° C. The reaction mixture was stirred at 0° C. until Example 27 was consumed completely. Careful removal of solvent at low temperature (<10° C.) provided the crude product, which was directly used for next step.

EXAMPLE 36B

N-(18-chloro-7-cyano-2-oxo-2,3,11,12,13,14-hexahydro-1H,10H-8,4-epiazeno-9,15,1,3,6-benzodioxatriazacycloheptadecin-17-yl)-3-(cyclopentylamino)propanamide A mixture of Example 36A (0.13 mmol) and cyclopentylamine (3 mL) was heated at 80° C. for 1 hour and concentrated. The residue was purified by reverse phase HPLC eluting with the gradient of 0%–70% of acetonitrile in 0.1% TFA aqueous solution to provide the desired product (TFA salt, 66.8 mg, 80% for two steps). MS (ESI) m/z 528.07 (M+H)$^+$, 526.16 (M−H)$^-$; $^1$H NMR (400 MHz, DMSO-D$^6$) δ ppm 1.50–1.66 (m, 8 H) 1.66–1.74 (m, 2 H) 1.79–1.87 (m, 2 H) 1.92–2.03 (m, 4 H) 2.82–2.85 (m, 2 H) 3.21 (m, 1 H) 3.52 (m, 1 H) 4.13 (t, J=4.30 Hz, 2 H) 4.61 (t, J=7.98 Hz, 2 H) 7.53 (s, 1 H) 8.01 (s, 1 H) 8.26 (s, 1 H) 8.40 (s, br, 1 H) 9.76 (s, 1 H) 9.93 (s, 1 H) 10.94 (s, 1 H).

EXAMPLE 37

N-(18-chloro-7-cyano-2-oxo-2,3,11,12,13,14-hexahydro-1H,10H-8,4-epiazeno-9,15,1,3,6-benzodioxatriazacycloheptadecin-17-yl)-3-[cyclohexyl(methyl)amino]propanamide The desired product (66.2 mg, 76% for two steps) was prepared using a similar procedure described in Example 36 by substituting cyclopentylamine with N-methylaminocyclohexane. MS (ESI) m/z 556.14 (M+H)$^+$, 554.16 (M−H)$^-$; $^1$H NMR (400 MHz, DMSO-D$^6$) δ ppm 1.14 (m, 1 H) 1.22–1.35 (m, 2 H) 1.38–1.51 (m, 2 H) 1.57–1.66 (m, 3 H) 1.78–1.88 (m, 4 H) 1.92–2.01 (m, 4 H) 2.74 (d, J=4.91 Hz, 3 H) 2.92 (t, J=6.44 Hz, 2 H) 3.19–3.32 (m, 2 H) 3.50 (m, 1 H) 4.09–4.16 (m, 2 H) 4.58–4.65 (m, 2 H) 7.51 (s, 1 H) 8.01 (s, 1 H) 8.26 (s, 1 H) 9.12 (s, 1 H) 9.76 (s, 1 H) 9.93 (s, 1 H) 10.94 (s, 1 H).

EXAMPLE 38

N-(18-chloro-7-cyano-2-oxo-2,3,11,12,13,14-hexahydro-1H,10H-8,4-epiazeno-9,15,1,3,6-benzodioxatriazacycloheptadecin-17-yl)methanesulfonamide To a solution of Example 27E (20 mg, 0.051 mmol) and pyridine (3 mL) in dichloromethane (10 mL) was added methanesulfonyl chloride (0.016 mL, 0.24 mmol) at 0° C. The reaction mixture was stirred 6 hours, and saturated NaHCO$_3$ was added to adjust pH value to 9. The precipitate was collected by filtration and washed with water thoroughly, purified by reverse phase HPLC to provide the desired product (20.2 mg, 85%). MS (DCI/NH$^3$) m/z 484.06 (M+H)$^+$; $^1$H NMR (400 MHz, DMSO-D6) δ ppm 1.66–1.73 (m, 2 H) 1.87–1.93 (m, 2 H) 1.98–2.06 (m, 2 H) 3.10 (s, 3 H) 4.24 (t, J=5.22 Hz, 2 H) 4.68 (t, J=7.98 Hz, 2 H) 7.19 (s, 1 H) 8.07 (s, 1 H) 8.35 (s, 1 H) 9.48 (s, 1 H) 10.01 (s, 1 H) 11.02 (s, 1 H).

EXAMPLE 39

N-(18-chloro-7-cyano-2-oxo-2,3,11,12,13,14-hexahydro-1H,10H-8,4-epiazeno-9,15,1,3,6-benzodioxatriazacycloheptadecin-17-yl)-6-morpholin-4-ylpyridine-3-sulfonamide The desired product (23.7 mg, 75%) was prepared using a similar procedure described in Example 38 by substituting methanesulfonyl chloride with 6-morpholin-4-yl-pyridine-3-sulfonyl chloride. MS (ESI) m/z 615.03 (M+H)$^+$, 613.06 (M−H)$^-$; $^1$H NMR (500 MHz, DMSO-D$^6$) δ ppm 1.60–1.65 (m, 2 H) 1.77–1.83 (m, 2 H) 1.91–1.98 (m, 2 H) 3.59 (t, J=5.30 Hz, 4 H) 3.67 (t, J=5.30 Hz, 4 H) 4.07 (t, J=4.99 Hz, 2 H) 4.60 (t, J=8.11 Hz, 2 H) 6.90 (d, J=9.05 Hz, 1 H) 6.97 (s, 1 H) 7.71 (dd, J=9.05, 2.50 Hz, 1 H) 7.99 (s, 1 H) 8.17 (s, 1 H) 8.29 (d, J=2.50 Hz, 1 H) 9.73 (s, 1 H) 9.90 (s, 1 H) 10.93 (s, 1 H).

EXAMPLE 40

N-(18-chloro-7-cyano-2-oxo-2,3,11,12,13,14-hexahydro-1H,10H-8,4-epiazeno-9,15,1,3,6-benzodioxatriazacycloheptadecin-17-yl)-2,2,2-trifluoroethanesulfonamide The desired product (22 mg, 80%) was prepared using a similar procedure described in Example 38 by substituting methanesulfonyl chloride with 2,2,2-trifluoroethylsulfonyl chloride. MS (ESI) m/z 532.99 (M−H)$^-$; $^1$H NMR (500 MHz, DMSO-D$^6$) δ ppm 1.61–1.67 (m, 2 H) 1.81–1.86 (m, 2 H) 1.93–1.99 (m, 2 H) 4.20 (t, J=4.99 Hz, 2 H) 4.53 (q, J=9.67 Hz, 2 H) 4.62 (t, J=8.11 Hz, 2 H) 7.14 (s, 1 H) 8.01 (s, 1 H) 8.31 (s, 1 H) 9.97 (s, 1 H) 10.14 (s, 1 H) 10.97 (s, 1 H).

EXAMPLE 41

N-(18-chloro-7-cyano-2-oxo-2,3,11,12,13,14-hexahydro-1H,10H-8,4-epiazeno-9,15,1,3,6-benzodioxatriazacycloheptadecin-17-yl)-4-fluorobenzenesulfonamide The desired product (18.3 mg, 65%) was prepared using a similar procedure described in Example 38 by substituting methanesulfonyl chloride with 4-fluorobenzenesulfonyl chloride. MS (ESI) m/z 545.00 (M−H)$^-$; $^1$H NMR (500 MHz, DMSO-D$^6$) δ ppm 1.59–1.65 (m, 2 H) 1.77–1.82 (m, 2 H) 1.91–1.97 (m, 2 H) 4.06 (t, J=4.99 Hz, 2 H) 4.60 (t, J=7.80 Hz, 2 H) 6.94 (s, 1 H) 7.39–7.43 (m, 2 H) 7.74–7.78 (m, 2 H) 7.99 (s, 1 H) 8.17 (s, 1 H) 9.91 (s, 1 H) 10.00 (s, 1 H) 10.94 (s, 1 H).

EXAMPLE 42

N-(18-chloro-7-cyano-2-oxo-2,3,11,12,13,14-hexahydro-1H,10H-8,4-epiazeno-9,15,1,3,6-benzodioxatriazacycloheptadecin-17-yl)-4-(trifluoromethoxy)benzenesulfonamide The desired product (17.6 mg, 56%) was prepared using a similar procedure described in Example 38 by substituting methanesulfonyl chloride with 4-trifluoromethoxybenzenesulfonyl chloride. MS (ESI) m/z 610.98 (M−H)$^-$; $^1$H NMR (500 MHz, DMSO-D$^6$) δ ppm 1.59–1.64 (m, 2 H) 1.75–1.80 (m, 2 H) 1.91–1.97 (m, 2 H) 4.02 (t, J=4.99 Hz, 2 H) 4.60 (t, J=8.11 Hz, 2 H) 6.87 (s, 1 H) 7.57 (d, J=8.73 Hz, 2 H) 7.83 (d, J=8.73 Hz, 2 H) 7.99 (s, 1 H) 8.18 (s, 1 H) 9.91 (s, 1 H) 10.11 (s, 1 H) 10.94 (s, 1 H).

EXAMPLE 43

18-chloro-17-(3-hydroxyprop-1-ynyl)-2-oxo-2,3,11,12,13,14-hexahydro-1H,10H-8,4-epiazeno-9,15,1,3,6-benzodioxatriazacycloheptadecine-7-carbonitrile

EXAMPLE 43A 18-chloro-7-cyano-2-oxo-2,3,11,12,13,14-hexahydro-1H,10H-8,4-epiazeno-9,15,1,3,6-benzodioxatriazacycloheptadecin-17-yl trifluoromethanesulfonate To a mixture of Example 10H (100 mg, 0.26 mmol) and triethylamine (0.039 mL, 0.28 mmol) in DMF (5 mL) at 0° C. was added trifluoromethanesulfonyl chloride (0.03 mL, 0.28 mmol). The reaction mixture was stirred at 0° C. for 30 minutes, and ice-water was added to quench the reaction. The resulting mixture was concentrated, and the residue was purified by flash chromatography eluting with 9% ethyl acetate in dichloromethane. The desired product (110 mg, 82%) was obtained as white solid. MS (ESI) 520.58 (M−H)$^-$; $^1$H NMR (400 MHz, DMSO-D$^6$) δ ppm 1.61–1.67 (m, 2 H) 1.81–1.87 (m, 2 H) 1.92–1.99 (m, 2 H) 4.24 (t, J=5.22 Hz, 2 H) 4.61 (t, J=7.98 Hz, 2 H) 7.38 (s, 1 H) 8.01 (s, 1 H) 8.46 (s, 1 H) 10.03 (s, 1 H) 11.06 (s, 1 H).

EXAMPLE 43B 18-chloro-2-oxo-17-[3-(tetrahydro-2H-pyran-2-yloxy)prop-1-ynyl]-2,3,11,12,13,14-hexahydro-1H,10H-8,4-epiazeno-9,15,1,3,6-benzodioxatriazacycloheptadecine-7-carbonitrile To a mixture of Example 43A (270 mg, 0.52 mmol), 2-prop-2-ynloxytetrahydropyran (0.436 mL, 3.10 mmol), triethylamine (0.217 mL, 1.56 mmol) and (PPh$^3$)$^4$Pd (180 mg, 0.156 mmol) in DMF was added CuI (20 mg, 0.10 mmol), followed by the addition of N-Bu$^4$NI (288 mg, 0.78 mmol). The reaction mixture was heated at 70° C. overnight, cooled and concentrated. The residue was purified by flash chromatography eluting 9% ethyl acetate in dichloromethane to provide the desired product (160 mg, 60%) as off-white solid. MS (ESI) m/z 510.02 (M−H)$^-$; $^1$H NMR (500 MHz, DMSO-D$^6$) δ ppm 1.44–1.55 (m, 4 H) 1.59–1.65 (m, 2 H) 1.66–1.76 (m, 2 H) 1.78–1.83 (m, 2 H) 1.90–1.96 (m, 2 H) 3.48 (m, 1 H) 3.76 (m, 1 H) 4.21 (t, J=4.99 Hz, 2 H) 4.43–4.54 (m, 2 H) 4.60 (d, J=8.11 Hz, 2 H) 4.85 (t, J=2.96 Hz, 1 H) 7.26 (s, 1 H) 7.98 (s, 1 H) 8.31 (s, 1 H) 9.99 (s, 1 H) 10.98 (s, 1 H).

EXAMPLE 43C 18-chloro-17-(3-hydroxyprop-1-ynyl)-2-oxo-2,3,11,12,13,14-hexahydro-1H,10H-8,4-epiazeno-9,15,1,3,6-benzodioxatriazacycloheptadecine-7-carbonitrile A mixture of Example 43B (6 mg, 0.014 mmol), HOAc (2 mL), THF (1 mL) and water (0.5 mL) was heated at 45° C. for 3 hours and concentrated. The residue was suspended in methanol, and the precipitates were collected by filtration. The desired product was obtained as white solid in quantitative yield. MS (ESI) m/z 425.95 (M–H)$^-$; $^1$H NMR (400 MHz, DMSO-D$^6$) δ ppm 1.54–1.67 (m, 2 H) 1.74–1.83 (m, 2 H) 1.85–1.98 (m, 2 H) 4.19 (s, br, 2 H) 4.35 (d, J=5.83 Hz, 2 H) 4.58 (s, br, 2 H) 5.37 (t, J=5.98 Hz, 1 H) 7.26 (s, 1 H) 7.94 (s, 1 H) 8.31 (s, 1 H) 10.01 (s, 1 H) 10.99 (s, 1 H).

EXAMPLE 44

18-chloro-2-oxo-17-[3-(tetrahydro-2H-pyran-2-yloxy)propyl]-2,3,11,12,13,14-hexahydro-1H,10H-8,4-epiazeno-9,15,1,3,6-benzodioxatriazacycloheptadecine-7-carbonitrile A mixture of Example 43B (45 mg, 0.088 mmol) and Pt/C (5%, 20 mg) in THF (5 mL) was stirred under hydrogen atmosphere (40 psi) for 16 hours. The insoluble materials were filtered off, and the filtrate was concentrated. The residue was purified by flash chromatography eluting with 9% ethyl acetate in dichloromethane to provide the desired product (36 mg, 80%). MS (ESI) m/z 513.93 (M–H)$^-$; $^1$H NMR (400 MHz, DMSO-D$^6$) δ ppm 1.38–1.53 (m, 4 H) 1.56–1.65 (m, 3 H) 1.71 (m, 1 H) 1.77–1.86 (m, 4 H) 1.88–1.98 (m, 2 H) 2.65–2.77 (m, 2 H) 3.31–3.45 (m, 2 H) 3.62–3.78 (m, 2 H) 4.17–4.21 (m, 2 H) 4.54 (m, 1 H) 4.60 (t, J=8.29 Hz, 2 H) 7.08 (s, 1 H) 7.97 (s, 1 H) 8.17 (s, 1 H) 9.88 (s, 1 H) 10.87 (s, 1 H).

EXAMPLE 45

18-chloro-17-(3-hydroxypropyl)-2-oxo-2,3,11,12,13,14-hexahydro-1H,10H-8,4-epiazeno-9,15,1,3,6-benzodioxatriazacycloheptadecine-7-carbonitrile A mixture of Example 44 (10 mg, 0.019 mmol), HOAc (4 mL), THF (2 mL) and water (1 mL) was heated at 45° C. overnight and concentrated. The residue was purified by reverse phase HPLC to provide the desired product (7 mg, 85%). MS (ESI) m/z 430.07 (M–H)$^-$; $^1$H NMR (400 MHz, DMSO-D$^6$) δ ppm 1.59–1.65 (m, 2 H) 1.67–1.75 (m, 2 H) 1.79–1.86 (m, 2 H) 1.91–1.99 (m, 2 H) 2.68 (t, J=7.98 Hz, 2 H) 3.42–3.47 (m, 2 H) 4.19 (t, J=4.91 Hz, 2 H) 4.50 (t, J=5.22 Hz, 1 H) 4.61 (t, J=7.98 Hz, 2 H) 7.07 (s, 1 H) 7.99 (s, 1 H) 8.16 (s, 1 H) 9.89 (s, 1 H) 10.90 (s, 1 H).

EXAMPLE 46

18-chloro-17-(2,3-dihydroxypropyl)-2-oxo-2,3,11,12,13,14-hexahydro-1H,10H-8,4-epiazeno-9,15,1,3,6-benzodioxatriazacycloheptadecine-7-carbonitrile

EXAMPLE 46A 17-allyl-18-chloro-2-oxo-2,3,11,12,13,14-hexahydro-1H,10H-8,4-epiazeno-9,15,1,3,6-benzodioxatriazacycloheptadecine-7-carbonitrile To a mixture of Example 43A (50 mg, 0.096 mmol), PdCl$^2$(PPh$^3$)$^2$ (8.1 mg, 0.0115 mmol), Ph$^3$P (15.1 mg, 0.058 mmol) and LiCl (32.6 mg, 0.77 mmol) in DMF (2 mL) was added tributylallyltin (0.059 mL, 0.192 mmol). The reaction mixture was heated at 110° C. for 1 hour and cooled. Saturated potassium fluoride aqueous solution (1 mL) was added. The resulting mixture was stirred for 30 min and concentrated. The residue was purified by flash chromatography eluting with 9% ethyl acetate in dichloromethane to provide the desired product (26 mg, 65%) as off-white solid. MS (ESI) m/z 411.98 (M–H)$^-$; $^1$H NMR (400 MHz, DMSO-D$^6$) δ ppm 1.56–1.65 (m, 2 H) 1.75–1.84 (m, 2 H) 1.90–1.98 (m, 2 H) 3.42 (d, J=6.14 Hz, 2 H) 4.16 (t, J=4.30 Hz, 2 H) 4.60 (t, J=7.98 Hz, 2 H) 5.05–5.09 (m, 2 H) 5.83–6.01 (m, 1 H) 7.07 (s, 1 H) 7.98 (s, 1 H) 8.19 (s, 1 H) 9.90 (s, 1 H) 10.90 (s, 1 H).

EXAMPLE 46B 18-chloro-17-(2,3-dihydroxypropyl)-2-oxo-2,3,11,12,13,14-hexahydro-1H,10H-8,4-epiazeno-9,15,1,3,6-benzodioxatriazacycloheptadecine-7-carbonitrile A mixture of Example 46A (10 mg, 0.024 mmol), THF (5 mL) and water (0.55 mL), and was treated with N-methylmorpholine-N-oxide (8.4 mg, 0.072 mmol), followed by the addition of 2.5% (W %) of OsO$^4$ in 2-methyl-2-propanol (0.04 mL) at 0° C. The reaction mixture was stirred at room temperature overnight and concentrated. The residue was purified by HPLC eluting with the gradient of 0%–70% of acetonitrile in 0.1% TFA aqueous solution. The desired product (9.3 mg, 85%) was obtained as white solid. MS (ESI) m/z 445.99 (M–H)$^-$; $^1$H NMR (400 MHz, DMSO-D$^6$) δ ppm 1.56–1.66 (m, 2 H) 1.78–1.86 (m, 2 H) 1.90–2.00 (m, 2 H) 2.54–2.62 (m, 2 H) 2.89 (dd, J=13.96, 4.76 Hz, 2 H) 3.70 (m, 1 H) 4.17 (t, J=4.91 Hz, 2 H) 4.61 (t, J=8.29 Hz, 2 H) 7.10 (s, 1 H) 8.00 (s, 1 H) 8.16 (s, 1 H) 9.90 (s, 1 H) 10.90 (s, 1 H).

EXAMPLE 47

18-chloro-17-(3-hydroxy-3-methylbut-1-ynyl)-2-oxo-2,3,11,12,13,14-hexahydro-1H,10H-8,4-epiazeno-9,15,1,3,6-benzodioxatriazacycloheptadecine-7-carbonitrile The desired product (22 mg, 50%) was prepared using a similar procedure described in Example 43B by substituting 2-prop-2-ynloxytetrahydropyran with 2-methyl-but-3-yn-2-ol. MS (ESI) m/z 454.03 (M–H)$^-$; $^1$H NMR (500 MHz, DMSO-D$^6$) δ ppm 1.49 (s, 6 H) 1.60–1.66 (m, 2 H) 1.79–1.84 (m, 2 H) 1.91–1.97 (m, 2 H) 4.21 (t, J=4.88 Hz, 2 H) 4.61 (t, J=7.93 Hz, 2 H) 5.50 (s, 1 H) 7.17 (s, 1 H) 8.00 (s, 1 H) 8.31 (s, 1 H) 9.99 (s, 1 H) 11.01 (s, 1 H).

EXAMPLE 48

18-chloro-17-(3-hydroxybut-1-ynyl)-2-oxo-2,3,11,12,13,14-hexahydro-1H,10H-8,4-epiazeno-9,15,1,3,6-benzodioxatriazacycloheptadecine-7-carbonitrile The desired product (25 mg, 60%) was prepared using a similar procedure described in Example 43B by substituting 2-prop-2-ynloxytetrahydropyran with but-3-yn-2-ol. MS (ESI) m/z 439.97 (M–H)$^-$; $^1$H NMR (500 MHz, DMSO-D$^6$) δ ppm 1.41 (d, J=6.71 Hz, 3 H) 1.60–1.66 (m, 2 H) 1.79–1.84 (m, 2 H) 1.91–1.97 (m, 2 H) 4.21 (t, J=5.19 Hz, 2 H) 4.59–4.66 (m, 3 H) 5.51 (d, J=5.19 Hz, 1 H) 7.21 (s, 1 H) 8.00 (s, 1 H) 8.31 (s, 1 H) 10.00 (s, 1 H) 11.01 (s, 1 H).

EXAMPLE 49

18-chloro-17-[3-(diethylamino)prop-1-ynyl]-2-oxo-2,3,11,12,13,14-hexahydro-1H,10H-8,4-epiazeno-9,15,1,3,6-benzodioxatriazacycloheptadecine-7-carbonitrile The desired product (66% yield) was prepared using a similar procedure described in Example 43B by substituting 2-prop-2-ynloxytetrahydropyran with diethylamino-2-propyne. MS (ESI) m/z 482.50 (M+H)$^+$, 481.1 (M–H)$^-$; $^1$H NMR (400 MHz, DMF-D$^7$) δ ppm 1.40 (t, J=7.21 Hz, 5 H) 1.72–1.79 (m, 2 H) 1.90–1.96 (m, 2 H) 2.00–2.09 (m, 2 H) 3.48 (q, J=7.21 Hz, 4 H) 4.31 (t, J=4.91 Hz, 2 H) 4.53 (s, 2 H) 4.75 (t, J=7.98 Hz, 2 H) 7.44 (s, 1 H) 8.18 (s, 1 H) 8.50 (s, 1 H) 10.16 (s, 1 H) 11.00 (s, 1 H).

EXAMPLE 50

18-chloro-17-[3-(dimethylamino)prop-1-ynyl]-2-oxo-2,3,11,12,13,14-hexahydro-1H,10H-8,4-epiazeno-9,15,1,3,6-benzodioxatriazacycloheptadecine-7-carbonitrile The desired product (45% yield) was prepared using a similar procedure described in Example 43B by substituting 2-prop-2-ynloxytetrahydropyran with dimethylamino-2-propyne. MS (ESI) m/z 454.8 (M+H)$^+$; $^1$H NMR (500 MHz, DMSO-D$^6$) δ ppm 1.61–1.67 (m, 2 H) 1.80–1.85 (m, 2 H) 1.92–1.98 (m, 2 H) 2.89 (s, 6 H) 4.23 (t, J=4.88 Hz, 2 H) 4.36 (s, 2 H) 4.63 (t, J=7.93 Hz, 2 H) 7.37 (s, 1 H) 8.01 (s, 1 H) 8.37 (s, 1 H) 10.05 (s, 1 H) 11.05 (s, 1 H).

EXAMPLE 51

18-chloro-17-(dimethylamino)-2-oxo-2,3,11,12,13,14-hexahydro-1H,10H-8,4-epiazeno-9,15,1,3,6-benzodioxatriazacycloheptadecine-7-carbonitrile To a solution of Example 27E (36 mg, 0.0925 mmol) in THF (6 mL) at 0° C. was added a mixture of formaldehyde (0.0345 mL, 0.463 mmol), 3 M H$^2$SO$^4$ (0.05 mL) and THF (0.5 mL), followed by the addition of NaBH$^4$ (11 mg, 0.28 mmol). The reaction mixture was stirred at 0° C. for 3 hours. Saturated NaHCO$^3$ was added to adjust the pH>7. The precipitates were collected, washed with water thoroughly, and purified by reverse phase HPLC eluting with the gradient of 0%–70% of acetonitrile in 0.1% TFA aqueous solution. The desired product (33 mg, 86%) was obtained as yellow solid. MS (ESI) m/z 415.35 (M–H)$^-$; $^1$HNMR (400 MHz, DMSO-D$^6$) δ ppm 1.34–1.41 (m, 2 H) 1.55–1.61 (m, 2 H) 1.66–1.76 (m, 2 H) 2.49 (s, 6 H) 3.97 (t, J=5.06 Hz, 2 H) 4.37 (t, J=7.98 Hz, 2 H) 6.62 (s, 1 H) 7.74 (s, 1 H) 7.88 (s, 1 H) 9.59 (s, 1 H) 10.62 (s, 1 H).

EXAMPLE 52

18-chloro-17-(diethylamino)-2-oxo-2,3,11,12,13,14-hexahydro-1H,10H-8,4-epiazeno-9,15,1,3,6-benzodioxatriazacycloheptadecine-7-carbonitrile To a solution of Example 27E (20 mg, 0.051 mmol) in THF (5 mL) at 0° C. was added a mixture of acetylaldehyde (0.014 mL, 0.255 mmol), 3 M H$^2$SO$^4$ (0.034 mL) and THF (0.5 mL), followed by the addition of NaBH$^4$ (7.7 mg, 0.20 mmol). The reaction mixture was stirred at 0° C. for 1 hours. Saturated NaHCO$^3$ was added to adjust the pH>7. The mixture was concentrated, and the precipitates were collected, washed with water thoroughly, and dried to provide the desired product (22 mg, 97%) as yellow solid. MS (DCI/NH$^3$) m/z 445.16 (M+H)$^+$; $^1$H NMR (500 MHz, DMSO-D$^6$) δ ppm 0.96 (t, J=7.02 Hz, 6 H) 1.57–1.64 (m, 2 H) 1.79–1.84 (m, 2 H) 1.92–1.99 (m, 2 H) 3.06 (q, J=7.02 Hz, 4 H) 4.20 (t, J=4.88 Hz, 2 H) 4.61 (t, J=7.93 Hz, 2 H) 6.89 (s, 1 H) 7.98 (s, 1 H) 8.15 (s, 1 H) 9.83 (s, 1 H) 10.90 (s, 1 H).

EXAMPLE 53

18-chloro-2-oxo-17-piperidin-1-yl-2,3,11,12,13,14-hexahydro-1H,10H-8,4-epiazeno-9,15,1,3,6-benzodioxatriazacycloheptadecine-7-carbonitrile The desired product (22 mg, 94%) was prepared using a similar procedure described in Example 52 by replacing acetylaldehyde with glutaraldehyde. MS (DCI/NH$^3$) m/z 457.18 (M+H)$^+$; $^1$H NMR (500 MHz, DMSO-D$^6$) δ ppm 1.50–1.56 (m, 2 H) 1.58–1.63 (m, 2 H) 1.63–1.68 (m, 4 H) 1.79–1.84 (m, 2 H) 1.92–1.98 (m, 2 H) 2.92 (t, J=4.68 Hz, 4 H) 4.21 (t, J=4.99 Hz, 2 H) 4.61 (t, J=8.11 Hz, 2 H) 6.82 (s, 1 H) 7.98 (s, 1 H) 8.13 (s, 1 H) 9.82 (s, 1 H) 10.86 (s, 1 H).

EXAMPLE 54

18-chloro-17-(isobutylamino)-2-oxo-2,3,11,12,13,14-hexahydro-1H,10H-8,4-epiazeno-9,15,1,3,6-benzodioxatriazacycloheptadecine-7-carbonitrile The desired product (12.8 mg, 52%) was prepared using a similar procedure described in Example 28 by replacing 3-pyridine carboxylaldehyde with isobutylaldehyde. MS (APCI) m/z 445.42 (M+H)$^+$; $^1$H NMR (500 MHz, DMSO-D$^6$) δ ppm 0.92 (d, J=6.41 Hz, 6 H) 1.54–1.61 (m, 2 H) 1.78–1.83 (m, 2 H) 1.87–1.99 (m, 3 H) 2.99 (t, J=6.56 Hz, 2 H) 4.18 (t, J=5.19 Hz, 2 H) 4.57 (t, J=8.24 Hz, 2 H) 5.08 (t, J=5.95 Hz, 1 H) 6.39 (s, 1 H) 7.93 (s, 1 H) 7.97 (s, 1 H) 9.68 (s, 1 H) 10.78 (s, 1 H).

EXAMPLE 55

17-chloro-11,12-dihydroxy-2-oxo-2,3,10,11,12,13-hexahydro-1H-8,4-epiazeno-9,14,1,3,6-benzodioxatriazacyclohexadecine-7-carbonitrile

EXAMPLE 55A

N-[6-(allyloxy)-5-cyanopyrazin-2-yl]-N'-(5-chloro-2-hydroxyphenyl)urea

The title compound was prepared using a similar procedure described in Example 88A by replacing Example 7F with Example 83B. MS (DCI) m/z 346.19 (M+H)$^+$.

EXAMPLE 55B

N-[2-(allyloxy)-5-chlorophenyl]-N'-[6-(allyloxy)-5-cyanopyrazin-2-yl]urea

To a solution of Example 55A (456 mg, 1.32 mmol) in anhydrous tetrahydrofuran (18 mL) was added polymer supported triphenylphosphine (659.5 mg, 1.98 mmol), di-tert-butyl azodicarboxylate (455.5 mg, 1.98 mmol), and allyl alcohol (76.6 mg, 1.32 mmol). The reaction mixture was shaken at room temperature for 5 hours. The solution was filtered, dried with silica gel powder (10 g), and purified by flash chromatography eluting with 20% ethyl acetate in hexanes (2 L) to give the title compound (140.8 mg, 28%). MS (ESI) m/z 385.95 (M+H)$^+$; $^1$H NMR (500 MHz, DMSO-D$^6$) δ ppm 4.71 (d, J=5.62 Hz, 2 H) 4.95 (d, J=5.30 Hz, 2 H) 5.29–5.36 (m, 2 H) 5.40–5.48 (m, 2 H) 6.00–6.16 (m, 2 H) 7.04–7.10 (m, 2 H) 8.20 (d, J=2.50 Hz, 1 H) 8.88 (s, 1 H) 9.05 (s, 1 H) 10.71 (s, 1 H).

EXAMPLE 55C 17-chloro-2-oxo-2,3,10,13-tetrahydro-1H-8,4-epiazeno-9,14,1,3,6-benzodioxatriazacyclohexadecine-7-carbonitrile Example 55B (140 mg, 0.36 mmol) was dissolved in dichloromethane (200 mL). The 2$^{nd}$ Generation Grubbs Catalyst (46 mg, 0.054 mmol) was added. The solution was purged with N$^2$ for 10 minutes, and heated at 40° C. overnight. The reaction mixture was concentrated, and dried with silica gel powder (5 g). The residue was purified by flash chromatography eluting with 5% ethyl acetate in dichloromethane (1 L) and then with 20% ethyl acetate in dichloromethane (1 L) to give the desired product (70 mg, 54%). MS (ESI) m/z 355.99 (M–H)$^-$; $^1$H NMR (400 MHz, DMSO-D$^6$) δ ppm 4.71 (d, J=3.38 Hz, 2 H) 5.56 (d, J=4.91 Hz, 2 H) 5.85–5.89 (m, 2 H) 7.12 (m, 1 H) 7.18 (m, 1 H) 7.98 (s, 1 H) 8.31 (d, J=2.45 Hz, 1 H) 10.91 (s, 1 H) 1.00 (s, 1 H).

EXAMPLE 55D 17-chloro-11,12-dihydroxy-2-oxo-2,3,10,11,12,13-hexahydro-1H-8,4-epiazeno-9,14,1,3,6-benzodioxatriazacyclohexadecine-7-carbonitrile Example 55C (70 mg, 0.20 mmol) was dissolved in tetrahydrofuran (27 mL) and water (3 mL). 4-Methylmorpholine N-oxide (34.3 mg, 0.29 mmol) and OsO$^4$ (2.5% in tert-butanol) (99.5 mg, 0.01 mmol) were added. The reaction was run at room temperature overnight. Then the solvents were removed. The residue was dissolved in DMSO/methanol (1/1, 8 mL) and purified by HPLC to give the title product (26.7 mg, 35%). MS (ESI) m/z 389.98 (M–H)$^-$; $^1$H NMR (500 MHz, DMSO-D$^6$) δ ppm 4.00–4.09 (m, 2 H) 4.17–4.31 (m, 3 H) 5.19 (dd, J=11.14, 4.12 Hz, 1 H) 5.33 (dd, J=16.63, 5.03 Hz, 2 H) 7.11 (dd, J=8.85, 2.44 Hz, 1 H) 7.25 (d, J=8.85 Hz, 1 H) 8.00 (s, 1 H) 8.33 (d, J=2.44 Hz, 1 H) 10.68 (s, 1 H) 10.98 (s, 1 H).

EXAMPLE 56

18-chloro-17-(methylamino)-2-oxo-2,3,11,12,13,14-hexahydro-1H,10H-8,4-epiazeno-9,15,1,3,6-benzodioxatriazacycloheptadecine-7-carbonitrile The desired product (7.7 mg, 25%) was prepared using a similar procedure described in Example 28 by replacing 3-pyridine carboxylaldehyde with formaldehyde. MS (APCI) m/z 403.24 (M+H)$^+$; $^1$H NMR (400 MHz, DMSO-D$^6$) δ ppm 1.54–1.62 (m, 2 H) 1.78–1.85 (m, 2 H) 1.92–2.00 (m, 2 H) 2.78 (s, 3 H) 4.21 (t, J=5.22 Hz, 2 H) 4.58 (t, J=8.29 Hz, 2 H) 5.33 (s, br, 1 H) 6.35 (s, 1 H) 7.94 (s, 1 H) 7.97 (s, 1 H) 9.69 (s, 1 H) 10.77 (s, 1 H).

EXAMPLE 57

14-chloro-11-oxo-2,3,11,12,18,18a-hexahydro-1aH,10H-5,9-epiazenooxireno[1][9,15,1,3,6]benzodioxatriazacycloheptadecine-6-carbonitrile Example 7 (100 mg, 0.27 mmol) was dissolved in dichloromethane (25 mL). To this solution was added m-CPBA (70% concentration, 658 mg, 2.67 mmol). The reaction mixture was stirred at room temperature for 3 days. Then the solvent was removed. The mixture was dissolved in acetone (50 mL), and dried with silica gel powder (20 g). 5% ethyl acetate in dichloromethane (1 L) and 20% ethyl acetate in dichloromethane (1 L) were used to run flash chromatography to provide the title compound (27.3 mg, 27%). MS (ESI) m/z 385.92 (M–H)$^-$; $^1$H NMR (400 MHz, DMSO-D$^6$) δ ppm 1.79 (m, 1 H) 2.64 (m, 1 H) 3.21 (m, 1 H) 3.34 (m, 1 H) 3.94 (t, J=9.97 Hz, 1 H) 4.45 (m, 1 H) 4.79 (dd, J=10.74, 4.30 Hz, 1 H) 5.20 (m, 1 H) 7.13 (dd, J=8.75, 2.61 Hz, 1 H) 7.23 (d, J=8.90 Hz, 1 H) 7.99 (s, 1 H) 8.22 (d, J=2.45 Hz, 1 H) 10.46 (s, 1 H) 10.99 (s, 1 H).

EXAMPLE 58

18-chloro-11,12-(cis)-dihydroxy-14-methyl-2-oxo-2,3,11,12,13,14-hexahydro-1H,10H-8,4-espiazeno-9,15,1,3,6-benzodioxatriazacycloheptadecine-7-carbonitrile

EXAMPLE 58A

N-[6-(allyloxy)-5-cyanopyrazin-2-yl]-N'-{5-chloro-2-[(1-methylbut-3-enyl)oxy]phenyl}urea Example 58A was synthesized using a similar procedure described in Example 55B by replacing allyl alcohol with pent-4-en-2-ol (260 mg, 40%). MS (ESI) m/z 411.98 (M–H)$^-$; $^1$H NMR (500 MHz, DMSO-D$^6$) δ ppm 1.30 (d, J=5.80 Hz, 3 H) 1.95 (m, 1 H) 2.38 (m, 1 H) 4.61 (m, 1 H) 4.96 (d, J=5.19 Hz, 2 H) 5.05–5.18 (m, 2 H) 5.32–5.49 (m, 2 H) 5.87 (m, 1 H) 6.12 (m, 1 H) 7.05 (dd, J=8.70, 2.59 Hz, 1 H) 7.14 (d, J=8.85 Hz, 1 H) 8.20 (d, J=2.75 Hz, 1 H) 8.82 (s, 1 H) 8.96 (s, 1 H) 10.80 (s, 1 H).

EXAMPLE 58B (cis) 18-chloro-14-methyl-2-oxo-2,3,13,14-tetrahydro-1H,10H-8,4-epiazeno-9,15,1,3,6-benzodioxatriazacycloheptadecine-7-carbonitrile Example 58B was synthesized by using a similar procedure described in Example 55C by replacing Example 55B with Example 58A (113.0 mg, 46%). This is the cis isomer. MS (ESI) m/z 383.94 (M–H)$^-$; $^1$H NMR (500 MHz, DMSO-D$^6$) δ ppm 1.19 (d, J=6.24 Hz, 3 H) 2.35 (m, 1 H) 2.56 (m, 1 H) 4.86 (m, 1 H) 5.16 (d, J=14.66 Hz, 1 H) 5.53 (m, 1 H) 5.63 (m, 1 H) 5.73 (m, 1 H) 7.11 (m, 1 H) 7.16 (m, 1 H) 8.02 (s, 1 H) 8.05 (d, J=2.50 Hz, 1 H) 9.75 (s, 1 H) 10.90 (s, 1 H).

EXAMPLE 58C 18-chloro-11,12-cis-dihydroxy-14-methyl-2-oxo-2,3,11,12,13,14-hexahydro-1H,10H-8,4-epiazeno-9,15,1,3,6-benzodioxatriazacycloheptadecine-7-carbonitrile Example 58 (16.2 mg, 22%) was synthesized using a similar procedure described in Example 55D by replacing Example 55C with Example 58B. MS (ESI) m/z 417.92 (M–H)⁻; ¹H NMR (400 MHz, DMSO-D⁶) δ ppm 1.21 (d, J=6.44 Hz, 3 H) 1.86 (m, 1 H) 1.98 (m, 1 H) 3.93 (m, 1 H) 4.21–4.32 (m, 2 H) 4.80 (d, J=4.30 Hz, 1 H) 4.88 (d, J=7.67 Hz, 1 H) 4.91–5.00 (m, 2 H) 7.12 (m, 1 H) 7.17 (m, 1 H) 7.99 (s, 1 H) 8.01 (d, J=2.45 Hz, 1 H) 9.90 (s, 1 H) 10.91 (s, 1 H).

EXAMPLE 59

18-chloro-11,12-trans-dihydroxy-14-methyl-2-oxo-2,3,11,12,13,14-hexahydro-1H,10H-8,4-epiazeno-9,15,1,3,6-benzodioxatriazacycloheptadecine-7-carbonitrile

EXAMPLE 59A (trans) 18-chloro-14-methyl-2-oxo-2,3,13,14-tetrahydro-1H,10H-8,4-epiazeno-9,15,1,3,6-benzodioxatriazacycloheptadecine-7-carbonitrile Example 59A was synthesized using a similar procedure described in Example 55C (75.1 mg, 31%). This was the trans isomer. MS (ESI) m/z 384.01 (M–H)⁻; ¹H NMR (500 MHz, DMSO-D₆) δ ppm 1.30 (d, J=6.24 Hz, 3 H) 2.20 (m, 1 H) 2.46 (m, 1 H) 4.67 (m, 1 H) 4.82 (m, 1 H) 4.96 (d, J=14.04 Hz, 1 H) 5.58–5.67 (m, 2 H) 7.13–7.19 (m, 2 H) 7.66 (s, 1 H) 7.98 (s, 1 H) 9.12 (s, 1 H) 10.83 (s, 1 H).

EXAMPLE 59B 18-chloro-11,12-trans-dihydroxy-14-methyl-2-oxo-2,3,11,12,13,14-hexahydro-1H,10H-8,4-epiazeno-9,15,1,3,6-benzodioxatriazacycloheptadecine-7-carbonitrile Example 59 was synthesized using a similar procedure described in Example 55D by replacing Example 55C with Example 59A (45.1 mg, 75%). MS (ESI) m/z 417.95 (M–H)⁻; ¹H NMR (400 MHz, DMSO-D⁶) δ ppm 1.17 (d, J=5.83 Hz, 3 H) 1.76 (m, 1 H) 1.99 (m, 1 H) 3.74 (m, 1 H) 3.91–4.02 (m, 2 H) 4.81 (m, 1 H) 4.96 (dd, J=11.51, 1.99 Hz, 1 H) 7.09–7.22 (m, 2 H) 8.00 (s, 1 H) 8.07 (d, J=2.45 Hz, 1 H) 10.05 (s, 1 H) 10.94 (s, 1 H).

EXAMPLE 60

18-chloro-15-methyl-2-oxo-2,3,10,11,12,13,14,15-octahydro-1H-8,4-epiazeno-9,1,3,6,15-benzoxatetraazacycloheptadecine-7-carbonitrile

EXAMPLE 60A

N-allyl-N-(4-chloro-2-nitrophenyl)-N-methylamine 4-chloro-1-fluoro-2-nitro-benzene (2.53 g, 14.41 mmol) was dissolved in anhydrous acetonitrile (80 mL). Allyl methyl amine (1.64 mL, 17.29 mmol) was added dropwise while the solution was stirred. The mixture was heated at 80° C. overnight, concentrated with silica gel powder (18 g), and purified by flash chromatography eluting with 10% ethyl acetate in hexanes (1 L) to give the title compound (3.05 g, 93%). MS (DCI) m/z 227.09 (M+H)⁺; ¹H NMR (300 MHz, CDCl³) δ ppm 2.80 (s, 3 H) 3.76 (d, J=5.43 Hz, 2 H) 5.16–5.29 (m, 2 H) 5.85 (m, 1 H) 7.00 (d, J=9.16 Hz, 1 H) 7.33 (dd, J=8.99, 2.54 Hz, 1 H) 7.74 (d, J=2.71 Hz, 1 H).

EXAMPLE 60B

N-allyl-N-(2-amino-4-chlorophenyl)-N-methylamine

Example 60A (3.05 g, 13.46 mmol), SnCl²·2H²O (15.18 g, 67.28 mmol), triethylamine (56 mL, 403.69 mmol), and ethanol (140 mL) were mixed, and heated at 70° C. for 2 hours. The reaction mixture was then cooled. The solution was filtered. The precipitate was washed with methanol (30 mL×3). The combined solution was dried with silica gel powder (15 g). 20% ethyl acetate in hexanes (1 L) was used to run flash chromatography to give the title compound (1.61 g, 61%). MS (DCI) m/z 196.99 (M+H)⁺; ¹H NMR (300 MHz, CD³OD) δ ppm 2.59 (s, 3 H) 3.42 (d, J=6.44 Hz, 2 H) 5.08–5.29 (m, 2 H) 5.86 (m, 1 H) 6.58 (dd, J=8.48, 2.37 Hz, 1 H) 6.72 (d, J=2.71 Hz, 1 H) 6.91 (d, J=8.48 Hz, 1 H).

EXAMPLE 60C

N-{2-[allyl(methyl)amino]-5-chlorophenyl}-N'-[6-(but-3-enyloxy)-5-cyanopyrazin-2-yl]urea A mixture of Example 60B (0.863 g, 4.39 mmol), Example 7F (1.36 g, 4.39 mmol) and anhydrous DMF (40 mL) was heated at 70° C. overnight. The solvent was removed, and 20% ethyl acetate in hexanes (20 mL) was added. The precipitate was ultrasonicated, filtered, washed with 20% ethyl acetate in hexanes (10 mL×3), and dried to give the title compound (1.2 g, 66%). MS (ESI) m/z 411.07 (M–H)⁻; ¹H NMR (500 MHz, DMSO-D⁶) δ ppm 2.53–2.57 (m, 2 H) 2.58 (s, 3 H) 3.49 (d, J=6.41 Hz, 2 H) 4.48 (t, J=6.71 Hz, 2 H) 5.12 (d, J=10.07 Hz, 2 H) 5.14–5.22 (m, 2 H) 5.77–5.93 (m, 2 H) 7.07 (dd, J=8.39, 2.59 Hz, 1 H) 7.24 (d, J=8.54 Hz, 1 H) 8.19 (d, J=2.44 Hz, 1 H) 8.90 (s, 1 H) 9.27 (s, 1 H) 16.90 (s, 1 H).

EXAMPLE 60D 18-chloro-15-methyl-2-oxo-2,3,10,11,14,15-hexahydro-1H-8,4-epiazeno-9,1,3,6,15-benzoxatetraazacycloheptadecine-7-carbonitrile Example 60D was synthesized using a similar procedure described in Example 55C by replacing Example 55B with Example 60C (0.79 g, 72%). MS (ESI) m/z 383.01 (M–H)⁻; ¹H NMR (500 MHz, CD²Cl²) δ ppm 2.52 (s, 3 H) 2.72 (q, J=7.90 Hz, 2 H) 3.55 (d, J=6.86 Hz, 2 H) 4.60–4.71 (m, 2 H) 5.66 (m, 1 H) 5.78 (m, 1 H) 7.08–7.15 (m, 2 H) 7.86 (s, 1 H) 7.99 (d, J=2.18 Hz, 1 H) 8.26 (s, 1 H) 10.39 (s, 1 H).

EXAMPLE 60E 18-chloro-15-methyl-2-oxo-2,3,10,11,12,13,14,15-octahydro-1H-8,4-epiazeno-9,1,3,6,15-benzoxatetraazacycloheptadecine-7-carbonitrile Example 60D (81.2 mg, 0.21 mmol) was dissolved in tetrahydrofuran (10 mL). To this solution was added 5% Pt/C (5 mg). The reaction mixture was stirred under hydrogen atmosphere (40 psi) at room temperature for 2 hours. The solution was filtered, and dried with silica gel powder (5 g). 10% ethyl acetate in dichloromethane (1 L) was used to run flash chromatography to give the title compound (69.4 mg, 85%). MS (ESI) m/z 384.79 (M–H)⁻; ¹H NMR (400 MHz, DMSO-D⁶) δ ppm 1.20–1.33 (m, 2 H) 1.36–1.48 (m, 2 H) 1.77–1.91 (m, 2 H) 2.43 (s, 3 H) 3.01 (t, J=5.22 Hz, 2 H) 4.49–4.64 (m, 2 H) 7.15 (m, 1 H) 7.23 (m, 1 H) 7.99 (s, 1 H) 8.01 (d, J=2.45 Hz, 1 H) 10.00 (s, 1 H) 10.93 (s, 1 H).

EXAMPLE 61

(cis) 18-chloro-13-hydroxy-2-oxo-2,3,13,14-tetrahydro-1H,10H-8,4-epiazeno-9,15,1,3,6-benzodioxatriazacycloheptadecine-7-carbonitrile

EXAMPLE 61A 2-(tetrahydro-2H-pyran-2-yloxy)but-3-en-1-ol

DL-2-Hydroxy-3-butenoic acid methyl ester (5 g, 43.06 mmol), 3,4-dihydro-2H-pyran (19.6 mL, 215.3 mmol), p-TsOH.H$^2$O (40 mg, 0.22 mmol) and dichloromethane (200 mL) were mixed, and stirred at room temperature for 3 hours. The solution was concentrated. The dried residue was dissolved in THF (250 mL) at 0° C. LiAlH$^4$ (3.27 g, 86.12 mmol) was added portionwise under N$^2$. The reaction mixture was slowly warmed up from 0° C. to room temperature, stirred overnight and cooled to 0° C. H$^2$O (5 mL) was added dropwise via syringe. The solvent was removed under reduced pressure. The residue was extracted with THF (500 mL). The solution was filtered, and dried with silica gel powder (20 g), and purified by flash chromatography eluting with 20% ethyl acetate in hexanes (2 L) to give the title compound (6.80 g, 89%). MS (DCI) m/z 177.44 (M+H)$^+$; $^1$H NMR (400 MHz, CDCl$^3$) δ ppm 1.44–1.62 (m, 4 H) 1.71 (m, 1 H) 1.84 (m, 1 H) 3.40–3.62 (m, 3 H) 3.88 (m, 1 H) 4.16 (m, 1 H) 4.62–4.81 (m, 2 H) 5.11–5.36 (m, 2 H) 5.81 (m, 1 H).

EXAMPLE 61B

N-[6-(allyloxy)-5-cyanopyrazin-2-yl]-N'-(5-chloro-2-{[2-(tetrahydro-2H-pyran-2-yloxy)but-3-enyl]oxy}phenyl)urea Example 61B was prepared using a similar procedure described in Example 55B by replacing allyl alcohol with Example 61A (442.7 mg, 77%). MS (ESI) m/z 498.06 (M–H)$^-$; $^1$H NMR (300 MHz, DMSO-D$^6$) δ ppm 1.35–1.77 (m, 6 H) 3.39 (m, 1 H) 3.76 (m, 1 H) 4.10–4.25 (m, 2 H) 4.50 (m, 1 H) 4.81 (m, 1 H) 4.96 (d, J=5.09 Hz, 2 H) 5.15–5.52 (m, 4 H) 5.78–6.20 (m, 2 H) 7.04–7.22 (m, 2 H) 8.15 (d, J=2.71 Hz, 1 H) 8.90 (s, 1 H) 8.93 (s, 1 H) 10.73 (s, 1 H).

EXAMPLE 61C 18-chloro-2-oxo-13-(tetrahydro-2H-pyran-2-yloxy)-2,3,13,14-tetrahydro-1H,10H-8,4-epiazeno-9,15,1,3,6-benzodioxatriazacycloheptadecine-7-carbonitrile Example 61C was synthesized using a similar procedure described in Example 55C by replacing 55B with 61B (144.9 mg, 35%). This product is a mixture of cis and trans isomers. MS (ESI) m/z 470.17 (M–H)$^-$; $^1$H NMR (400 MHz, DMSO-D$^6$) δ ppm 1.32–1.79 (m, 6 H) 3.45 (m, 1 H) 3.76 (m, 1 H) 4.03 (m, 1 H) 4.17–4.46 (m, 2 H) 4.68 (m, 1 H) 4.79–5.06 (m, 2 H) 5.23–5.94 (m, 2 H) 7.07–7.27 (m, 2 H) 7.99 (s, 1 H) 9.16 (s, 1 H) 9.66 (s, 1 H) 10.89 (s, 1 H).

EXAMPLE 61D (cis) 18-chloro-13-hydroxy-2-oxo-2,3,13,14-tetrahydro-1H,10H-8,4-epiazeno-9,15,1,3,6-benzodioxatriazacycloheptadecine-7-carbonitrile Example 61C (21 mg, 0.04 mmol) was dissolved in THF (2 mL). Water (1 mL) and glacial acetic acid (4 mL) were added. The reaction mixture was stirred at room temperature overnight. The solvents were removed via vacuum pump. The residue was dissolved in DMSO/methanol (1/1, 3 mL), and separated by HPLC to give the trans and cis isomers. The title compound was the cis isomer (1.6 mg, 9%). MS (ESI) m/z 385.80 (M–H)$^-$; $^1$H NMR (500 MHz, DMSO-D$^6$) δ ppm 3.84 (t, J=8.58 Hz, 1 H) 4.24 (dd, J=8.73, 4.06 Hz, 1 H) 4.59 (m, 1 H) 5.38 (m, 1 H) 5.46 (d, J=4.68 Hz, 1 H) 5.61 (m, 1 H) 6.48 (s, 2 H) 7.07–7.22 (m, 2 H) 8.03 (s, 1 H) 8.25 (d, J=2.50 Hz, 1 H) 9.77 (s, 1 H) 10.93 (s, 1 H).

EXAMPLE 62

18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile Example 61C (21 mg, 0.044 mmol) was oxidized using a similar procedure described in Example 55D. After the oxidation reaction, the solution was concentrated, and the residue was treated with a mixture of acetic acid, THF and water by using a similar procedure described in Example 61 to give the title compound (6.3 mg, 34%). MS (ESI) m/z 420.01 (M–H)$^-$; $^1$H NMR (500 MHz, DMSO-D$^6$) δ ppm 3.74 (m, 1 H) 3.88–4.03 (m, 2 H) 4.12 (m, 1 H) 4.21–4.34 (m, 2 H) 4.65 (m, 1 H) 5.06–5.20 (m, 3 H) 7.10–7.27 (m, 2 H) 8.00 (s, 1 H) 8.27 (d, J=2.50 Hz, 1 H) 10.14 (s, 1 H) 10.93 (s, 1 H).

EXAMPLE 63

18-chloro-13-hydroxy-2-oxo-2,3,11,12,13,14-hexahydro-1H,10H-8,4-epiazeno-9,15,1,3,6-benzodioxatriazacycloheptadecine-7-carbonitrile Example 61C (43 mg, 0.091 mmol) was hydrogenated by using a similar procedure described in Example 60. The reaction solution was filtered, and concentrated. The residue was treated with a mixture of acetic acid, THF and water using a similar procedure described in Example 61 to give the title compound (2.7 mg, 8%). MS (ESI) m/z 387.96 (M–H)$^-$; $^1$H NMR (500 MHz, DMSO-D$^6$) δ ppm 1.65 (m, 1 H) 1.76 (m, 1 H) 1.85 (m, 1 H) 2.04 (m, 1 H) 3.87 (m, 1 H) 4.03 (dd, J=10.45, 6.71 Hz, 1 H) 4.21 (dd, J=10.61, 3.12 Hz, 1 H) 4.61 (t, J=7.49 Hz, 1 H) 5.03 (d, J=4.37 Hz, 1 H) 7.13 (m, 1 H) 7.19 (m, 1 H) 8.01 (s, 1 H) 8.17 (d, J=2.50 Hz, 1 H) 10.03 (s, 1 H) 10.94 (s, 1 H).

EXAMPLE 64

(trans, trans) 18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile

EXAMPLE 64A (trans) 18-chloro-13-hydroxy-2-oxo-2,3,13,14-tetrahydro-1H,10H-8,4-epiazeno-9,15,1,3,6-benzodioxatriazacycloheptadecine-7-carbonitrile Example 61C (200 mg, 0.42 mmol) was deprotected using a similar procedure described in Example 61D. HPLC separation gave the cis and trans isomers. The title isomer was trans (25.9 mg, 16%). MS (ESI) m/z 386.08 (M–H)$^-$; $^1$H NMR (500 MHz, DMSO-D$^6$) δ ppm 3.97 (dd, J=9.98, 6.55 Hz, 1 H) 4.22 (dd, J=9.98, 3.74 Hz, 1 H) 4.31 (m, 1 H)

5.25 (d, J=5.30 Hz, 1 H) 5.63 (m, 1 H) 5.81 (m, 1 H) 6.48 (s, 2 H) 7.12–7.19 (m, 2 H) 7.80 (d, J=1.87 Hz, 1 H) 8.02 (s, 1 H) 9.16 (s, 1 H) 10.85 (s, 1 H).

EXAMPLE 64B (trans, trans) 18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile Example 64A (23.2 mg, 0.06 mmol) was oxidized by using a similar procedure described in Example 55D to give the title compound (7.4 mg, 29%). MS (ESI) m/z 419.96 (M−H)$^-$; $^1$H NMR (500 MHz, DMSO-D$^6$) δ ppm 3.72 (m, 1 H) 3.90 (m, 1 H) 4.00 (m, 1 H) 4.11 (m, 1 H) 4.30 (m, 1 H) 4.61–4.68 (m, 2 H) 4.91–5.21 (m, 3 H) 7.08–7.27 (m, 2 H) 7.99 (s, 1 H) 8.27 (d, J=2.50 Hz, 1 H) 10.13 (s, 1 H) 10.92 (s, 1 H).

EXAMPLE 65

(cis, trans) 18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile Example 65 (22.3 mg, 61%) was prepared using a similar procedure described in Example 55D by replacing Example 55C with Example 61D. MS (ESI) m/z 419.97 (M−H)$^-$; $^1$H NMR (300 MHz, DMSO-D$^6$) δ ppm 3.74 (m, 1 H) 3.91–4.00 (m, 2 H) 4.18–4.36 (m, 3 H) 4.90 (dd, J=10.85, 2.37 Hz, 1 H) 5.11 (dd, J=5.26, 2.20 Hz, 2 H) 5.18 (d, J=4.75 Hz, 1 H) 7.13–7.18 (m, 2 H) 7.99–8.03 (m, 2 H) 9.71 (s, 1 H) 10.92 (s, 1 H).

EXAMPLE 66

18-bromo-2-oxo-2,3,11,14-tetrahydro-1H,10H-8,4-epiazeno-9,15,1,3,6-benzodioxatriazacycloheptadecine-7-carbonitrile

EXAMPLE 66A 1-(allyloxy)-4-bromo-2-nitrobenzene

To a mixture of anhydrous THF (200 mL) and 95% NaH (757 mg, 29.96 mmol) at 0° C. under N$^2$ was added allyl alcohol (2.04 mL, 29.96 mmol) dropwise. After 0.5 hour, 4-bromo-1-fluoro-2-nitro-benzene (5.07 g, 23.04 mmol) was added dropwise. The reaction was warmed from 0° C. to room temperature under N$^2$ overnight, and inorganic salt was filtered. The filtrate was concentrated with silica gel powder (20 g), and purified by flash chromatogrphy eluting with 10% ethyl acetate in hexanes (1 L) and 20% ethyl acetate in hexanes (1 L) to give the title compound (5.06 g, 85%). MS (DCI) m/z 257.35 (M+H)$^+$; $^1$H NMR (300 MHz, CDCl$^3$) δ ppm 4.65–4.70 (m, 2 H) 5.35 (m, 1 H) 5.48 (m, 1 H) 6.02 (m, 1 H) 6.97 (d, J=9.16 Hz, 1 H) 7.61 (dd, J=8.99, 2.54 Hz, 1 H) 7.97 (d, J=2.37 Hz, 1 H).

EXAMPLE 66B 2-(allyloxy)-5-bromoaniline

A mixture of Example 66A (5.06 g, 19.69 mmol), iron powder (11.02 g, 196.9 mmol), NH$^4$Cl (0.53 g, 9.85 mmol), ethanol (160 mL), and water (40 mL) were heated at 80° C. for 6 hours. The solution was filtered, concentrated with silica gel powder (18 g), and purified by flash chromatography eluting with 10% ethyl acetate in hexanes (1 L) to give the title compound (4.53 g, 97%). MS (DCI) m/z 227.91 (M+H)$^+$; $^1$H NMR (300 MHz, CDCl$^3$) δ ppm 4.54 (d, J=5.43 Hz, 2 H) 5.29 (dd, J=10.51, 1.36 Hz, 1 H) 5.40 (dd, J=17.46, 1.53 Hz, 1 H) 6.09 (m, 1 H) 6.65 (d, J=8.48 Hz, 1 H) 6.84 (m, 1 H) 6.91 (d, J=2.37 Hz, 1 H).

EXAMPLE 66C

N-[2-(allyloxy)-5-bromophenyl]-N'-[6-(but-3-enyloxy)-5-cyanopyrazin-2-yl]urea

Example 66C (3.97 g, 100%) was prepared using a similar procedure described in Example 60C by replacing Example 60B with Example 66B. MS (ESI) m/z 441.94 (M−H)$^-$; $^1$H NMR (300 MHz, DMSO-D$^6$) δ ppm 2.52–2.59 (m, 2 H) 4.46 (t, J=6.61 Hz, 2 H) 4.71 (d, J=5.42 Hz, 2 H) 5.07–5.23 (m, 2 H) 5.31 (dd, J=10.51, 1.70 Hz, 1 H) 5.43 (dd, J=17.29, 1.70 Hz, 1 H) 5.88 (m, 1 H) 6.08 (m, 1 H) 7.03 (d, J=8.81 Hz, 1 H) 7.19 (dd, J=8.65, 2.54 Hz, 1 H) 8.32 (d, J=2.37 Hz, 1 H) 8.88 (s, 1 H) 9.07 (s, 1 H) 10.71 (s, 1 H).

EXAMPLE 66D 18-bromo-2-oxo-2,3,11,14-tetrahydro-1H,10H-8,4-epiazeno-9,15,1,3,6-benzodioxatriazacycloheptadecine-7-carbonitrile Example 66C (1.22 g, 2.75 mmol) was cyclized using a similar procedure described in Example 55C to give the title compound (0.67 g, 59%). MS (ESI) m/z 413.91 (M−H)$^-$; $^1$H NMR (500 MHz, DMSO-D$^6$) δ ppm 2.70 (q, J=7.49 Hz, 2 H) 4.63–4.71 (m, 4 H) 6.01 (m, 1 H) 6.08 (m, 1 H) 7.16 (m, 1 H) 7.23 (m, 1 H) 7.97 (s, 1 H) 8.23 (d, J=2.50 Hz, 1 H) 10.32 (s, 1 H) 10.94 (s, 1 H).

EXAMPLE 67

18-bromo-12,13-dihydroxy-2-oxo-2,3,11,12,13,14-hexahydro-1H,10H-8,4-epiazeno-9,15,1,3,6-benzodioxatriazacycloheptadecine-7-carbonitrile Example 66D (52 mg, 0.12 mmol) was oxidized using a similar procedure described in Example 55D to give the title compound (41.2 mg, 79%). MS (ESI) m/z 447.86 (M−H); $^1$H NMR (400 MHz, DMSO-D$^6$) δ ppm 1.92 (m, 1 H) 2.33 (m, 1 H) 3.75–3.87 (m, 2 H) 4.07–4.17 (m, 2 H) 4.60 (m, 1 H) 4.70 (m, 1 H) 4.90 (d, J=4.91 Hz, 1 H) 5.08 (d, J=4.91 Hz, 1 H) 7.13 (d, J=8.90 Hz, 1 H) 7.26 (dd, J=8.75, 2.61 Hz, 1 H) 7.99 (s, 1 H) 8.28 (d, J=2.45 Hz, 1 H) 9.78 (s, 1 H) 10.93 (s, 1 H).

EXAMPLE 68

2-oxo-18-[3-(tetrahydro-2H-pyran-2-yloxy)propyl]-2,3,11,14-tetrahydro-1H,10H-8,4-epiazeno-9,15,1,3,6-benzodioxatriazacycloheptadecine-7-carbonitrile

EXAMPLE 68A 1-(benzyloxy)-4-bromo-2-nitrobenzene

A mixture of 4-bromo-2-nitro-phenol (5.05 g, 23.16 mmol), benzyl bromide (4.12 mL, 34.73 mmol) and K$^2$CO$^3$ (9.60 g, 69.48 mmol) in acetone (200 mL) were stirred, and refluxed for 3 hours. The solution was filtered, dried with silica gel powder (20 g), and separated by flash chromatography eluting with 5% ethyl acetate in hexanes (1 L) and then with 20% ethyl acetate in hexanes (1 L) to give the title compound (6.84 g, 96%). MS (DCI) m/z 326.90 (M+NH$_4$)$^+$; $^1$H NMR (500 MHz, CD$^2$Cl$^2$) δ ppm 5.21 (s, 2 H) 7.06 (d, J=9.05 Hz, 1 H) 7.33–7.46 (m, 5 H) 7.63 (dd, J=8.73, 2.50 Hz, 1 H) 7.97 (d, J=2.50 Hz, 1 H).

EXAMPLE 68B 2-({3-[4-(benzyloxy)-3-nitrophenyl]prop-2-ynyl}oxy)tetrahydro-2H-pyran Example 68A (500 mg, 1.62 mmol), 2-prop-2-ynyloxy-tetrahydro-pyran (1.14 mL, 8.11 mmol), Pd(PPh$^3$)$^2$Cl$^2$ (171 mg, 0.24 mmol), CuI (2 mg, 0.011 mmol), PPh$^3$ (320 mg, 1.22 mmol), triethylamine (1 mL), and DMF (3 mL) were mixed and purged with N$^2$. The mixture was heated at 120° C. for 25 minutes in a Smith Synthesizer. The solvents were removed via vacuum pump. The residue was dissolved in acetone. The solution was dried with silica gel powder (10 g). 10% Ethyl acetate in hexanes (2 L) was used to run flash chromatography to give the title compound (0.60 g, 100%). MS (DCI) m/z 385.10 (M+NH$^4$)$^+$; $^1$H NMR (300 MHz, CD$^3$OD) δ ppm 1.45–1.92 (m, 6 H) 3.48–3.60 (m, 2 H) 3.88 (m, 1 H) 4.45 (s, 1 H) 4.46 (s, 1 H) 5.29 (s, 2 H) 7.29–7.42 (m, 4 H) 7.43–7.48 (m, 2 H) 7.61 (dd, J=8.82, 2.03 Hz, 1 H) 7.87 (d, J=2.03 Hz, 1 H).

EXAMPLE 68C 2-amino-4-[3-(tetrahydro-2H-pyran-2-yloxy)propyl]phenol

A mixture of Example 68B (1.19 g, 3.25 mmol), 20% Pd(OH)$^2$/C (100 mg), and ethanol (50 mL) were stirred, and heated at 50° C. for 2 hours under H$^2$ atmosphere (60 psi). The solution was filtered, dried with silica gel powder (8 g), and purified by flash chromatography eluting with 30% ethyl acetate in hexanes (1 L) and then with 1% methanol in ethyl acetate (1 L) to give the title compound (0.37 g, 45%). MS (DCI) m/z 252.05 (M+H)$^+$; $^1$H NMR (300 MHz, CD$^3$OD) δ ppm 1.46–1.62 (m, 4 H) 1.70 (m, 1 H) 1.76–1.90 (m, 3 H) 2.45–2.58 (m, 2 H) 3.37 (m, 1 H) 3.49 (m, 1 H) 3.71 (m, 1 H) 3.86 (m, 1 H) 4.55 (t, J=3.73 Hz, 1 H) 6.41 (dd, J=7.97, 2.20 Hz, 1 H) 6.59 (m, 1 H) 6.61 (s, 1 H).

EXAMPLE 68D

N-[6-(but-3-enyloxy)-5-cyanopyrazin-2-yl]-N'-{2-hydroxy-5-[3-(tetrahydro-2H-pyran-2-yloxy)propyl]phenyl}urea Example 68C (0.37 g, 1.47 mmol) was coupled with Example 7F using a similar procedure described in Example 60C to give the title compound (645.4 mg, 94%). MS (ESI) m/z 466.12 (M–H)$^-$; $^1$H NMR (300 MHz, DMSO-D$^6$) δ ppm 1.36–1.55 (m, 4 H) 1.62 (m, 1 H) 1.69–1.85 (m, 3 H) 2.52–2.60 (m, 2 H) 3.40 (m, 1 H) 3.63 (m, 1 H) 3.74 (m, 1 H) 3.98–4.05 (m, 3 H) 4.45–4.57 (m, 3 H) 5.06–5.25 (m, 2 H) 5.89 (m, 1 H) 6.72 (m, 1 H) 6.79 (m, 1 H) 7.93 (d, J=2.03 Hz, 1 H) 8.73 (s, 1 H) 9.16 (s, 1 H) 9.86 (s, 1 H) 10.57 (s, 1 H).

EXAMPLE 68E

N-{2-(allyloxy)-5-[3-(tetrahydro-2H-pyran-2-yloxy)propyl]phenyl}-N'-[6-(but-3-enyloxy)-5-cyanopyrazin-2-yl]urea Example 68E (200 mg, 51%) was synthesized using a similar procedure described in Example 55B by replacing Example 55A with Example 68D. MS (ESI) m/z 506.13 (M–H)$^-$; $^1$H NMR (500 MHz, DMSO-D$^6$) δ ppm 1.39–1.50 (m, 4 H) 1.62 (m, 1 H) 1.69–1.85 (m, 3 H) 2.52–2.67 (m, 4 H) 3.34 (m, 1 H) 3.42 (m, 1 H) 3.63 (m, 1 H) 3.74 (m, 1 H) 3.97 (m, 1 H) 4.38 (m, 1 H) 4.46 (t, J=6.71 Hz, 1 H) 4.54 (m, 1 H) 4.66 (m, 1 H) 5.04–5.25 (m, 2 H) 5.21–5.46 (m, 2 H) 5.87 (m, 1 H) 6.10 (m, 1 H) 6.85 (dd, J=8.27, 2.03 Hz, 1 H) 6.96 (d, J=8.42 Hz, 1 H) 7.97 (d, J=2.18 Hz, 1 H) 8.87 (s, 1 H) 8.93 (s, 1 H) 10.63 (s, 1 H).

EXAMPLE 68F 2-oxo-18-[3-(tetrahydro-2H-pyran-2-yloxy)propyl]-2,3,11,14-tetrahydro-1H,10H-8,4-epiazeno-9,15,1,3,6-benzodioxatriazacycloheptadecine-7-carbonitrile Example 68E (200 mg, 0.39 mmol) was cyclized using a similar procedure described in Example 55C to give the title compound (70 mg, 37%). MS (ESI) m/z 478.00 (M–H)$^-$; $^1$H NMR (400 MHz, DMSO-D$^6$) δ ppm 1.35–1.54 (m, 4 H) 1.63 (m, 1 H) 1.68–1.85 (m, 3 H) 2.54–2.63 (m, 2 H) 2.71 (q, J=7.26 Hz, 2 H) 3.35 (m, 1 H) 3.42 (m, 1 H) 3.64 (m, 1 H) 3.74 (m, 1 H) 4.54 (m, 1 H) 4.61–4.73 (m, 4 H) 5.99 (m, 1 H) 6.10 (m, 1 H) 6.90 (dd, J=8.44, 1.99 Hz, 1 H) 7.08 (d, J=8.29 Hz, 1 H) 7.91 (d, J=2.15 Hz, 1 H) 7.98 (s, 1 H) 10.26 (s, 1 H) 10.85 (s, 1 H).

EXAMPLE 69

2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile

EXAMPLE 69A benzyl 2-nitro-4-vinylphenyl ether

A mixture of Example 68A (2.18 g, 7.08 mmol), Pd(PPh$^3$)$^4$ (1.23 g, 1.06 mmol) and tributyl-vinyl-stannane (2.48 mL, 8.49 mmol) in DMF (200 mL) was heated at 80° C. overnight. The solvent was removed by vacuum pump. The residue was dissolved in acetone (50 mL), and dried with silica gel powder (20 g). 10% ethyl acetate in hexanes (2 L) was used to run flash chromatography to give the title compound (1.69 g, 94%). MS (DCI) m/z 273.03 (M+NH$^4$)$^+$; $^1$H NMR (500 MHz, CD$^2$Cl$^2$) δ ppm 5.23 (s, 2 H) 5.72 (d, J=17.47 Hz, 1 H) 6.67 (dd, J=17.78, 10.92 Hz, 1 H) 7.12 (d, J=8.73 Hz, 1 H) 7.35 (m, 1 H) 7.38–7.43 (m, 2 H) 7.44–7.48 (m, 2 H) 7.56 (dd, J=8.73, 2.18 Hz, 1 H) 7.87 (d, J=2.18 Hz, 1 H).

EXAMPLE 69B

2-[4-(benzyloxy)-3-nitrophenyl]ethanol

Example 69A (1.69 g, 6.62 mmol) was dissolved in anhydrous THF (60 mL). To this solution was added 9-BBN (0.5 M, 16 mL, 7.94 mmol). The reaction mixture was stirred under $N_2$ at room temperature overnight. NaOH (0.32 g, 8.00 mmol) in $H_2O$ (2 mL) was added, followed by the dropwise addition of 30% $H_2O_2$ (0.90 mL, 7.94 mmol). The mixture was stirred at room temperature for 3 hours. All the solvents were removed. To the residue was added ethyl acetate (200 mL) and water (200 mL) for extraction. The organic phase was dried over $MgSO_4$, and concentrated with silica gel powder (20 g). 20% ethyl acetate in hexanes (1 L) and 60% ethyl acetate in hexanes (1 L) were used to run flash chromatography to give the title compound (0.89 g, 63%). MS (DCI) m/z 291.04 $(M+NH_4)^+$; $^1H$ NMR (300 MHz, $CDCl_3$) δ ppm 2.86 (t, J=6.44 Hz, 2 H) 3.87 (t, J=6.44 Hz, 2 H) 5.22 (s, 2 H) 7.06 (d, J=8.48 Hz, 1 H) 7.29–7.49 (m, 6 H) 7.74 (d, J=2.37 Hz, 1 H).

EXAMPLE 69C

2-{2-[4-(benzyloxy)-3-nitrophenyl]ethoxy}tetrahydro-2H-pyran

A mixture of Example 69B (0.89 g, 3.27 mmol), 3,4-dihydro-2H-pyran (1.49 mL, 16.34 mmol) and p-TsOH.$H_2O$ (5 mg) in dichloromethane (20 mL) were stirred at room temperature overnight. The reaction solution was dried with silica gel powder (15 g). 20% ethyl acetate in hexanes (1 L) was used to run flash chromatography to give the title compound (1.06 g, 91%). MS (DCI) m/z 375.13 $(M+NH_4)^+$; $^1H$ NMR (400 MHz, $CDCl_3$) δ ppm 1.42–1.62 (m, 4 H) 1.68 (m, 1 H) 1.79 (m, 1 H) 2.88 (t, J=6.60 Hz, 2 H) 3.45 (m, 1 H) 3.59 (m, 1 H) 3.70 (m, 1 H) 3.94 (m, 1 H) 4.58 (t, J=3.38 Hz, 1 H) 5.21 (s, 2 H) 7.03 (d, J=8.59 Hz, 1 H) 7.28–7.48 (m, 6 H) 7.77 (d, J=2.15 Hz, 1 H).

EXAMPLE 69D 2-amino-4-[2-(tetrahydro-2H-pyran-2-yloxy)ethyl]phenol

Example 69C (1 g, 2.80 mmol) was reduced using a similar procedure described in Example 68C to give the title compound (512.1 mg, 77%). MS (DCI) m/z 238.04 $(M+H)^+$; $^1H$ NMR (300 MHz, $CD_3OD$) δ ppm 1.40–1.59 (m, 4 H) 1.67 (m, 1 H) 1.81 (m, 1 H) 2.70 (t, J=7.29 Hz, 2 H) 3.44 (m, 1 H) 3.54 (m, 1 H) 3.71–3.88 (m, 2 H) 4.57 (t, J=3.56 Hz, 1 H) 6.45 (dd, J=8.14, 2.03 Hz, 1 H) 6.60 (d, J=8.14 Hz, 1 H) 6.64 (d, J=2.03 Hz, 1 H).

EXAMPLE 69E

N-[6-(but-3-enyloxy)-5-cyanopyrazin-2-yl]-N'-{2-hydroxy-5-[2-(tetrahydro-2H-pyran-2-yloxy)ethyl]phenyl}urea Example 69D (512.1 mg, 2.16 mmol) was coupled with Example 7F using a similar procedure described in Example 60C to give the title compound (864.8 mg, 88%). MS (ESI) m/z 452.08 $(M-H)^-$; $^1H$ NMR (400 MHz, DMSO-$D_6$) δ ppm 1.33–1.52 (m, 4 H) 1.58 (m, 1 H) 1.72 (m, 1 H) 2.54 (q, J=6.44 Hz, 2 H) 2.67–2.76 (m, 2 H) 3.39 (m, 1 H) 3.51 (m, 1 H) 3.67 (m, 1 H) 3.75 (m, 1 H) 4.50 (t, J=6.60 Hz, 2 H) 4.56 (m, 1 H) 5.05–5.22 (m, 2 H) 5.88 (m, 1 H) 6.71–6.81 (m, 2 H) 7.95 (s, 1 H) 8.71 (s, 1 H) 9.15 (s, 1 H) 9.90 (s, 1 H) 10.54 (s, 1 H).

EXAMPLE 69F

N-{2-(allyloxy)-5-[2-(tetrahydro-2H-pyran-2-yloxy)ethyl]phenyl}-N'-[6-(but-3-enyloxy)-5-cyanopyrazin-2-yl]urea Example 69F (449.1 mg, 47%) was prepared using a similar procedure described in Example 55B. MS (ESI) m/z 492.08 $(M-H)^-$; $^1H$ NMR (500 MHz, DMSO-$D_6$) δ ppm 1.34–1.50 (m, 4 H) 1.59 (m, 1 H) 1.70 (m, 1 H) 2.47 (m, 1 H) 2.55 (m, 1 H) 2.74–2.86 (m, 2 H) 3.39 (m, 1 H) 3.55 (m, 1 H) 3.65 (m, 1 H) 3.78 (m, 1 H) 3.98 (t, J=4.84 Hz, 1 H) 4.39 (t, J=6.71 Hz, 1 H) 4.46 (t, J=6.55 Hz, 1 H) 4.58 (m, 1 H) 4.66 (m, 1 H) 5.05–5.45 (m, 4 H) 5.87 (m, 1 H) 6.08 (m, 1 H) 6.89 (dd, J=8.42, 1.87 Hz, 1 H) 7.09 (d, J=8.73 Hz, 1 H) 8.01 (d, J=2.18 Hz, 1 H) 8.86 (s, 1 H) 8.94 (s, 1 H) 10.62 (s, 1 H).

EXAMPLE 69G 2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile Example 69F (449 mg, 0.91 mmol) was cyclized using a similar procedure described in Example 55C to give the title compound (126 mg, 30%). MS (ESI) m/z 464.03 $(M-H)^-$; $^1H$ NMR (500 MHz, DMSO-$D_6$) δ ppm 1.35–1.53 (m, 4 H) 1.60 (m, 1 H) 1.70 (m, 1 H) 2.74–2.79 (m, 2 H) 2.80–2.88 (m, 2 H) 3.35–3.42 (m, 2 H) 3.54 (m, 1 H) 3.65 (m, 1 H) 4.57 (m, 1 H) 4.63–4.71 (m, 4 H) 5.98 (m, 1 H) 6.10 (m, 1 H) 6.92–7.00 (m, 2 H) 7.96 (d, J=2.14 Hz, 1 H) 7.98 (s, 1 H) 10.26 (s, 1 H) 10.87 (s, 1 H).

EXAMPLE 70

18-(3-hydroxypropyl)-2-oxo-2,3,11,14-tetrahydro-1H,10H-8,4-epiazeno-9,15,1,3,6-benzodioxatriazacycloheptadecine-7-carbonitrile Example 68F (70 mg, 0.15 mmol) was deprotected using a similar procedure described in Example 61 to give the title compound (38 mg, 66%). MS (ESI) m/z 394.14 $(M-H)^-$; $^1H$ NMR (400 MHz, DMSO-$D_6$) δ ppm 1.63–1.74 (m, 2 H) 2.52–2.58 (m, 2 H) 2.71 (q, J=7.47 Hz, 2 H) 3.38–3.46 (m, 2 H) 4.43 (t, J=5.52 Hz, 1 H) 4.61–4.73 (m, 4 H) 5.98 (m, 1 H) 6.10 (m, 1 H) 6.88 (dd, J=8.44, 1.99 Hz, 1 H) 7.07 (d, J=8.29 Hz, 1 H) 7.89 (d, J=1.84 Hz, 1 H) 7.99 (s, 1 H) 10.26 (s, 1 H) 10.83 (s, 1 H).

EXAMPLE 71

18-(2-hydroxyethyl)-2-oxo-2,3,11,14-tetrahydro-1H,10H-8,4-epiazeno-9,15,1,3,6-benzodioxatriazacycloheptadecine-7-carbonitrile Example 69G (125 mg, 0.27 mmol) was deprotected using a similar procedure described in Example 61 to give the title compound (43.9 mg, 43%). MS (ESI) m/z 380.10 $(M-H)^-$; $^1H$ NMR (400 MHz, DMSO-$D_6$) δ ppm 2.61–2.76 (m, 4 H) 3.56 (t, J=7.06 Hz, 2 H) 4.59–4.73 (m, 4 H) 5.98 (m, 1 H) 6.10 (m, 1 H) 6.91 (dd, J=8.44, 1.99 Hz, 1 H) 7.08 (d, J=8.29 Hz, 1 H) 7.90 (d, J=1.84 Hz, 1 H) 7.98 (s, 1 H) 10.24 (s, 1 H) 10.83 (s, 1 H).

EXAMPLE 72

18-bromo-2-oxo-2,3,11,12,13,14-hexahydro-1H,
10H-8,4-epiazeno-9,15,1,3,6-benzodioxatriazacyclo-
heptadecine-7-carbonitrile Example 66 (215 mg, 0.52 mmol) was hydrogenated using a similar procedure described in Example 60 to give the title compound (80 mg, 37%). MS (ESI) m/z 417.91 (M–H)$^-$; $^1$H NMR (400 MHz, DMSO-D$^6$) δ ppm 1.58–1.66 (m, 2 H) 1.78–1.87 (m, 2 H) 1.91–1.99 (m, 2 H) 4.14–4.23 (m, 2 H) 4.58–4.67 (m, 2 H) 7.10 (d, J=8.90 Hz, 1 H) 7.25 (dd, J=8.59, 2.45 Hz, 1 H) 8.00 (s, 1 H) 8.32 (d, J=2.45 Hz, 1 H) 9.94 (s, 1 H) 10.93 (s, 1 H).

EXAMPLE 73

18-hydroxy-2-oxo-2,3,11,14-tetrahydro-1H,10H-8,4-
epiazeno-9,15,1,3,6-benzodioxatriazacycloheptade-
cine-7-carbonitrile

EXAMPLE 73A 2-(2,5-dimethoxyphenyl)-1H-isoindole-1,3 (2
H)-dione 2,5-dimethoxyaniline (9.96 g, 65.00 mmol) and phthalic anhydride (10.11 g, 68.25 mmol) were mixed, and heated at 185° C. for 15 minutes under N$^2$. After the reaction mixture was cooled, acetone (50 mL) was added. The precipitate was ultrasonicated, filtered, washed with ethyl acetate (10 mL×2), and dried to give the title compound (17.5 g, 95%). MS (ESI) m/z 283.91 (M+H)$^+$; $^1$H NMR (300 MHz, CDCl$^3$) δ ppm 3.75 (s, 3 H) 3.79 (s, 3 H) 6.83 (t, J=1.70 Hz, 1 H) 6.98 (d, J=1.70 Hz, 2 H) 7.74–7.81 (m, 2 H) 7.91–7.98 (m, 2 H).

EXAMPLE 73B 2-(2,5-dihydroxyphenyl)-1H-isoindole-1,3(2
H)-dione

Example 73A (17.5 g, 61.78 mmol) was dissolved in anhydrous dichloromethane (1 L). The solution was put in a dry ice bath for 0.5 hour. BBr$^3$ (19.3 mL, 204.9 mmol) was added dropwise. The dry ice bath was removed, and the reaction mixture was stirred for additional 2 hours. Then it was poured into ice-water (2 L). The precipitate was filtered, washed with water (2 L), and dried to give the title compound (14.16 g, 90%). MS (ESI) m/z 253.95 (M–H)$^-$; $^1$H NMR (500 MHz, CD$^3$OD) δ ppm 6.65 (d, J=2.81 Hz, 1 H) 6.78 (m, 1 H) 6.83 (m, 1 H) 7.84–7.88 (m, 2 H) 7.91–7.95 (m, 2 H).

EXAMPLE 73C 2-(5-{[tert-butyl(diphenyl)silyl]oxy}-2-hydroxyphe-
nyl)-1H-isoindole-1,3(2H)-dione A mixture of Example 73B (5.31 g, 20.81 mmol), tert-butyldiphenylsilyl chloride (5.68 mL, 21.85 mmol), imidazole (2.83 g, 41.62 mmol) in anhydrous DMF (100 mL) was heated at 50° C. for 2 days. The solvent was removed via vacuum pump. THF (200 mL) was added. The mixture was ultrosonicated. The suspension was filtered. The solution was dried with silica gel powder (20 g). 20% ethyl acetate in hexanes (1 L) and 30% ethyl acetate in hexanes (1 L) were used to perform flash chromatography to give the title compound (7 g, 68%). MS (APCI) m/z 492.19 (M–H)$^-$; $^1$H NMR (500 MHz, CDCl$^3$) δ ppm 1.10 (s, 9H) 6.64 (dd, J=8.73, 2.81 Hz, 1 H) 6.78 (d, J=8.73 Hz, 1 H) 6.86 (d, J=2.81 Hz, 1 H) 7.34–7.45 (m, 6 H) 7.70–7.75 (m, 4 H) 7.78 (dd, J=5.46, 2.96 Hz, 2 H) 7.92 (dd, J=5.30, 3.12 Hz, 2 H).

EXAMPLE 73D 2-(2-(allyloxy)-5-{[tert-butyl(diphenyl)silyl]
oxy}phenyl)-1H-isoindole-1,3(2H)-dione A mixture of Example 73C (7 g, 14.2 mmol), allyl bromide (1.84 mL, 21.27 mmol) and K$^2$CO$^3$ (3.92 g, 28.36 mmol) in anhydrous acetone (200 mL) were stirred, and refluxed overnight. The suspension was filtered, and dried with silica gel powder (20 g). 15% ethyl acetate in hexanes (2 L) was used to run flash chromatography to give the title compound (6.74 g, 89%). MS (DCI) m/z 551.13 (M+NH$^4$)$^+$; $^1$H NMR (300 MHz, CDCl$^3$) δ ppm 1.09 (s, 9H) 4.37–4.43 (m, 2 H) 5.02–5.22 (m, 2 H) 5.83 (m, 1 H) 6.65–6.69 (m, 2 H) 6.83 (d, J=2.37 Hz, 1 H) 7.34–7.47 (m, 6 H) 7.70–7.78 (m, 6 H) 7.89–7.94 (m, 2 H).

EXAMPLE 73E 2-(allyloxy)-5-{[tert-butyl(diphenyl)silyl]
oxy}aniline

Example 73D (2.61 g, 4.89 mmol) was dissolved in methanol (100 mL). Hydrazine (20 mL) was added. The reaction was stirred at room temperature overnight. The solvent and hydrazine were removed by vacuum pump. The residue was dissolved in acetone (30 mL). The solution was dried with silica gel powder (15 g). 5% Ethyl acetate in hexanes (2 L) was used to run flash chromatography to give the title compound (0.72 g, 36%). MS (DCI) m/z 404.11 (M+H)$^+$; $^1$H NMR (500 MHz, CDCl$^3$) δ ppm 1.07 (s, 9H) 4.42 (d, J=5.19 Hz, 2 H) 5.22 (dd, J=10.53, 1.37 Hz, 1 H) 5.34 (dd, J=17.39, 1.53 Hz, 1 H) 5.97–6.08 (m, 2 H) 6.24 (d, J=2.75 Hz, 1 H) 6.49 (d, J=8.85 Hz, 1 H) 7.33–7.44 (m, 6 H) 7.71 (dd, J=8.09, 1.37 Hz, 4 H).

EXAMPLE 73F

N-(2-(allyloxy)-5-{[tert-butyl(diphenyl)silyl]
oxy}phenyl)-N'-[6-(but-3-enyloxy)-5-cyanopyrazin-
2-yl]urea Example 73E (724 mg, 1.75 mmol) was coupled with Example 7F using a similar procedure described in Example 60C to give the title compound (957.1 mg, 88%). MS (ESI) m/z 618.36 (M–H)$^-$; $^1$H NMR (300 MHz, DMSO-D$^6$) δ ppm 1.04 (s, 9H) 2.52–2.59 (m, 2 H) 4.45 (t, J=6.61 Hz, 2 H) 4.53 (d, J=5.43 Hz, 2 H) 5.06–5.44 (m, 4 H) 5.78–6.11 (m, 2 H) 6.21 (dd, J=8.99, 2.88 Hz, 1 H) 6.76 (d, J=8.82 Hz, 1 H) 7.40–7.50 (m, 6 H) 7.68 (dd, J=7.46, 1.70 Hz, 4 H) 7.83 (d, J=3.05 Hz, 1 H) 8.83 (s, 1 H) 8.90 (s, 1 H) 10.64 (s, 1 H).

EXAMPLE 73G

18-{[tert-butyl(diphenyl)silyl]oxy}-2-oxo-2,3,11,14-
tetrahydro-1H,10H-8,4-epiazeno-9,15,1,3,6-benzo-
dioxatriazacycloheptadecine-7-carbonitrile Example 73F (957.1 mg, 1.54 mmol) was cyclized by using a similar procedure described in Example 55C to give the title compound (516.6 mg, 57%). MS (ESI) m/z 590.28 (M–H)$^-$; $^1$H NMR (400 MHz, DMSO-D$^6$) δ ppm 1.04 (s, 9H) 2.66 (q, J=7.16 Hz, 2 H) 4.53 (d, J=6.75 Hz, 2 H) 4.67

(t, J=7.21 Hz, 2 H) 5.91–6.08 (m, 2 H) 6.29 (dd, J=8.90, 3.07 Hz, 1 H) 6.88 (d, J=8.90 Hz, 1 H) 7.39–7.52 (m, 6 H) 7.64–7.72 (m, 4 H) 7.78 (d, J=3.07 Hz, 1 H) 7.95 (s, 1 H) 10.20 (s, 1 H) 10.81 (s, 1 H).

EXAMPLE 73H 18-hydroxy-2-oxo-2,3,11,14-tetrahydro-1H,10H-8,4-epiazeno-9,15,1,3,6-benzodioxatriazacycloheptadecine-7-carbonitrile Example 73G (0.52 g, 0.87 mmol) was dissolved in THF (10 mL). To this solution was added TBAF (1.37 g, 5.24 mmol). The reaction mixture was stirred at room temperature for 3 hours, and dried with silica gel powder (10 g). 20% Ethyl acetate in hexanes (1 L) and 1% methanol in ethyl acetate (1 L) were used to run flash chromatography. The title compound was obtained (0.32 g, 100%). MS (ESI) m/z 352.06 (M–H)$^-$; $^1$H NMR (500 MHz, DMSO-D$^6$) δ ppm 2.68 (q, J=7.42 Hz, 2 H) 4.56 (d, J=7.32 Hz, 2 H) 4.68 (t, J=7.48 Hz, 2 H) 5.97 (m, 1 H) 6.07 (m, 1 H) 6.43 (dd, J=8.70, 2.90 Hz, 1 H) 6.96 (d, J=8.85 Hz, 1 H) 7.64 (d, J=3.05 Hz, 1 H) 7.96 (s, 1 H) 9.03 (s, 1 H) 10.21 (s, 1 H) 10.86 (s, 1 H).

EXAMPLE 74

18-(2-hydroxyethyl)-2-oxo-2,3,11,12,13,14-hexahydro-1H,10H-8,4-epiazeno-9,15,1,3,6-benzodioxatriazacycloheptadecine-7-carbonitrile Example 71 (20.6 mg, 0.05 mmol) was hyrdogenated using a similar procedure described in Example 60 to give the title compound (11 mg, 53%). MS (ESI) m/z 382.19 (M–H)$^-$; $^1$H NMR (400 MHz, DMSO-D$^6$) δ ppm 1.54–1.64 (m, 2 H) 1.75–1.85 (m, 2 H) 1.88–2.01 (m, 2 H) 2.66 (t, J=7.06 Hz, 2 H) 3.52–3.61 (m, 2 H) 4.15 (t, J=5.22 Hz, 2 H) 4.53–4.66 (m, 3 H) 6.92 (m, 1 H) 7.01 (d, J=8.29 Hz, 1 H) 7.95 (d, J=1.84 Hz, 1 H) 7.99 (s, 1 H) 9.86 (s, 1 H) 10.79 (s, 1 H).

EXAMPLE 75

18-(3-hydroxypropyl)-2-oxo-2,3,11,12,13,14-hexahydro-1H,10H-8,4-epiazeno-9,15,1,3,6-benzodioxatriazacycloheptadecine-7-carbonitrile Example 70 (20.6 mg, 0.05 mmol) was hydrogenated using a similar procedure described in Example 60 to give the title compound (14.9 mg, 70%). MS (ESI) m/z 396.11 (M–H)$^-$; $^1$H NMR (400 MHz, DMSO-D$^6$) δ ppm 1.55–1.64 (m, 2 H) 1.64–1.73 (m, 2 H) 1.76–1.85 (m, 2 H) 1.90–2.00 (m, 2 H) 2.52–2.58 (m, 2 H) 3.41 (t, J=6.44 Hz, 2 H) 4.10–4.18 (m, 2 H) 4.44 (m, 1 H) 4.58–4.66 (m, 2 H) 6.90 (dd, J=8.59, 2.15 Hz, 1 H) 7.01 (d, J=8.29 Hz, 1 H) 7.94 (d, J=1.84 Hz, 1 H) 8.00 (s, 1 H) 9.87 (s, 1 H) 10.79 (s, 1 H).

EXAMPLE 76

12,13-dihydroxy-18-(2-hydroxyethyl)-2-oxo-2,3,11,12,13,14-hexahydro-1H,10H-8,4-epiazeno-9,15,1,3,6-benzodioxatriazacycloheptadecine-7-carbonitrile Example 71 (17 mg, 0.04 mmol) was oxidized using a similar procedure described in Example 55D to give the title compound (13.9 mg, 75%). MS (ESI) m/z 414.21 (M–H)$^-$; $^1$H NMR (400 MHz, DMSO-D$^6$) δ 1.91 (m, 1 H) 2.34 (m, 1 H) 2.66 (t, J=7.21 Hz, 2 H) 3.53–3.61 (m, 2 H) 3.76 (m, 1 H) 3.84 (m, 1 H) 4.05 (m, 1 H) 4.13 (m, 1 H) 4.54–4.62 (m, 2 H) 4.68 (m, 1 H) 4.85 (d, J=5.22 Hz, 1 H) 5.04 (d, J=4.91 Hz, 1 H) 6.94 (m, 1 H) 7.04 (d, J=7.98 Hz, 1 H) 7.90 (d, J=1.84 Hz, 1 H) 8.00 (s, 1 H) 9.71 (s, 1 H) 10.79 (s, 1 H).

EXAMPLE 77

12,13-dihydroxy-18-(3-hydroxypropyl)-2-oxo-2,3,11,12,13,14-hexahydro-1H,10H-8,4-epiazeno-9,15,1,3,6-benzodioxatriazacycloheptadecine-7-carbonitrile Example 70 (23 mg, 0.06 mmol) was oxidized using a similar procedure described in Example 55D to give the title compound (12.3 mg, 49%). MS (ESI) m/z 428.19 (M–H)$^-$; $^1$H NMR (400 MHz, DMSO-D$^6$) δ ppm 1.63–1.73 (m, 2 H) 1.91 (m, 1 H) 2.35 (m, 1 H) 2.52–2.58 (m, 2 H) 3.38–3.46 (m, 2 H) 3.77 (m, 1 H) 3.84 (m, 1 H) 4.06 (m, 1 H) 4.13 (m, 1 H) 4.42 (t, J=5.06 Hz, 1 H) 4.56–4.73 (m, 10.89 Hz, 2 H) 4.85 (d, J=5.22 Hz, 1 H) 5.04 (d, J=5.22 Hz, 1 H) 6.91 (dd, J=8.44, 1.99 Hz, 1 H) 7.04 (d, J=8.59 Hz, 1 H) 7.90 (d, J=1.84 Hz, 1 H) 8.00 (s, 1 H) 9.72 (s, 1 H) 10.76 (s, 1 H).

EXAMPLE 78

18-chloro-13-methoxy-2-oxo-2,3,13,14-tetrahydro-1H,10H-8,4-epiazeno-9,15,1,3,6-benzodioxatriazacycloheptadecine-7-carbonitrile

EXAMPLE 78A 2-methoxybut-3-en-1-ol

Butadiene monoxide (3.26 g, 46.5 mmol) was dissolved in methanol (30 mL). The solution was cooled in an ice bath for 0.5 hour. One drop of concentrated H$^2$SO$^4$ was added. The ice bath was removed, and the reaction was stirred at room temperature for 3 hours. The reaction solution was dried with silica gel powder (20 g). 20% Ethyl acetate in hexanes (1 L) was used to run flash chromatography to give the title compound (1.16 g, 25%). MS (ESI) m/z 103.15 (M+H)$^+$; $^1$H NMR (300 MHz, CDCl$^3$) δ ppm 3.35 (s, 3 H) 3.47–3.63 (m, 2 H) 3.72 (m, 1 H) 5.27–5.39 (m, 2 H) 5.68 (m, 1 H).

EXAMPLE 78B

N-[6-(allyloxy)-5-cyanopyrazin-2-yl]-N'-{5-chloro-2-[(2-methoxybut-3-enyl)oxy]phenyl}urea Example 78B (0.23 g, 36%) was prepared using a similar procedure described in Example 55B by replacing allyl alcohol with Example 78A. MS (ESI) m/z 428.13 (M–H)$^-$; $^1$H NMR (300 MHz, DMSO-D$^6$) δ ppm 3.28 (s, 3 H) 4.11–4.15 (m, 2 H) 4.95 (t, J=1.53 Hz, 1 H) 4.97 (t, J=1.53 Hz, 1 H) 5.25–5.51 (m, 5 H) 5.87 (m, 1 H) 6.12 (m, 1 H) 7.07 (m, 1 H) 7.14 (m, 1 H) 8.18 (d, J=2.37 Hz, 1 H) 8.90 (s, 1 H) 8.98 (s, 1 H) 10.79 (s, 1 H).

EXAMPLE 78C 18-chloro-13-methoxy-2-oxo-2,3,13,14-tetrahydro-1H,10H-8,4-epiazeno-9,15,1,3,6-benzodioxatriaza-cycloheptadecine-7-carbonitrile Example 78B (0.23 g, 0.54 mmol) was cyclized using a similar procedure described in Example 55C to give the title compound (41.1 mg, 19%) with cis conformation. MS (ESI) m/z 400.06 (M–H)$^-$; $^1$H NMR (400 MHz, DMSO-D$^6$) δ ppm 3.39 (s, 3 H) 3.96 (t, J=8.29 Hz, 1 H) 4.29–4.45 (m, 2 H) 5.27–5.50 (m, 2 H) 5.58 (s, 1 H) 5.84 (m, 1 H) 7.17 (dd, J=8.90, 2.76 Hz, 1 H) 7.28 (d, J=8.90 Hz, 1 H) 8.07 (s, 1 H) 8.29 (d, J=2.45 Hz, 1 H) 9.76 (s, 1 H) 10.99 (s, 1 H).

EXAMPLE 79

18-chloro-11,12-dihydroxy-13-methoxy-2-oxo-2,3,11,12,13,14-hexahydro-1H,10H-8,4-epiazeno-9,15,1,3,6-benzodioxatriazacycloheptadecine-7-carbonitrile Example 78C (35 mg, 0.087 mmol) was oxidized using a similar procedure described in Example 55D to give the title compound (12.9 mg, 34%). MS (ESI) m/z 434.09 (M–H)$^-$; $^1$H NMR (400 MHz, DMSO-D$^6$) δ ppm 3.33 (s, 3 H) 3.61 (d, J=7.36 Hz, 1 H) 3.81 (t, J=6.14 Hz, 1 H) 4.08 (dd, J=9.82, 2.76 Hz, 1 H) 4.19 (t, J=11.20 Hz, 1 H) 4.29 (m, 1 H) 4.36 (m, 1 H) 4.92 (dd, J=11.35, 2.45 Hz, 1 H) 5.17 (d, J=5.83 Hz, 1 H) 5.20 (d, J=5.52 Hz, 1 H) 7.05–7.24 (m, 2 H) 7.85–8.10 (m, 2 H) 9.64 (s, 1 H) 10.89 (s, 1 H).

EXAMPLE 80

(trans) 18-chloro-11,12-dihydroxy-13-methoxy-2-oxo-2,3,11,12,13,14-hexahydro-1H,10H-8,4-epiazeno-9,15,1,3,6-benzodioxatriazacycloheptadecine-7-carbonitrile

EXAMPLE 80A (trans) 18-chloro-13-methoxy-2-oxo-2,3,13,14-tetrahydro-1H,10H-8,4-epiazeno-9,15,1,3,6-benzodioxatriazacycloheptadecine-7-carbonitrile The title compound has trans conformation and was prepared using the same procedure in Example 78 (108 mg, 50%). MS (ESI) m/z 400.11 (M–H)$^-$; $^1$H NMR (400 MHz, DMSO-D$^6$) δ ppm 3.32 (s, 3 H) 3.66 (m, 1 H) 4.02–4.16 (m, 2 H) 4.20 (m, 1 H) 4.38 (dd, J=10.28, 3.53 Hz, 1 H) 5.06 (m, 1 H) 5.66 (dd, J=16.26, 6.14 Hz, 1 H) 5.97 (d, J=15.96 Hz, 1 H) 7.19–7.30 (m, 2 H) 7.84 (d, J=2.46 Hz, 1 H) 8.07 (s, 1 H) 9.23 (s, 1 H) 10.93 (s, 1 H).

EXAMPLE 80B 18-chloro-11,12-trans-dihydroxy-13-methoxy-2-oxo-2,3,11,12,13,14-hexahydro-1H,10H-8,4-epiazeno-9,15,1,3,6-benzodioxatriazacycloheptadecine-7-carbonitrile Example 80A (48 mg, 0.12 mmol) was oxidized using a similar procedure described in Example 55D to give the title compound (22 mg, 42%). MS (ESI) m/z 434.24 (M–H)$^-$; $^1$H NMR (400 MHz, DMSO-D$^6$) δ ppm 3.32 (s, 3 H) 3.57 (d, J=7.06 Hz, 1 H) 3.87 (d, J=6.14 Hz, 1 H) 4.05–4.17 (m, J=9.82, 9.82 Hz, 2 H) 4.36 (dd, J=10.43, 7.67 Hz, 1 H) 4.58 (m, 1 H) 4.71 (m, 1 H) 5.31 (m, 1 H) 7.14 (dd, J=8.75, 2.61 Hz, 1 H) 7.22 (m, 1 H) 8.00 (s, 1 H) 8.28 (d, J=2.76 Hz, 1 H) 10.14 (s, 1 H) 10.95 (s, 1 H).

EXAMPLE 81

18-chloro-13-ethoxy-11,12-cis-dihydroxy-2-oxo-2,3,11,12,13,14-hexahydro-1H,10H-8,4-epiazeno-9,15,1,3,6-benzodioxatriazacycloheptadecine-7-carbonitrile

EXAMPLE 81A 2-ethoxybut-3-en-1-ol

Example 81A (4.1 g, 75%) was synthesized using a similar procedure described in Example 78A by replacing methanol with ethanol. MS (ESI) m/z 117.12 (M+H)$^+$; $^1$H NMR (300 MHz, CDCl$^3$) δ ppm 1.13–1.28 (m, 3 H) 3.31–4.00 (m, 5 H) 5.18–5.39 (m, 2 H) 5.71 (m, 1 H).

EXAMPLE 81B

N-[6-(allyloxy)-5-cyanopyrazin-2-yl]-N'-{5-chloro-2-[(2-ethoxybut-3-enyl)oxy]phenyl}urea Example 81B (179 mg, 27%) was prepared using a similar procedure described in Example 55B by replacing allyl alcohol with Example 81A. MS (ESI) m/z 442.20 (M–H)$^-$; $^1$H NMR (300 MHz, DMSO-D$^6$) δ ppm 0.96–1.22 (m, 3 H) 3.11–3.43 (m, 3 H) 3.51 (m, 1 H) 3.96–4.25 (m, 2 H) 4.96 (d, J=5.43 Hz, 1 H) 5.06–5.52 (m, 4 H) 5.81–6.20 (m, 2 H) 7.03–7.20 (m, 2 H) 8.18 (d, J=2.71 Hz, 1 H) 8.89 (s, 1 H) 8.99 (s, 1 H) 10.78 (s, 1 H).

EXAMPLE 81C (cis) 18-chloro-13-ethoxy-2-oxo-2,3,13,14-tetrahydro-1H,10H-8,4-epiazeno-9,15,1,3,6-benzodioxatriazacycloheptadecine-7-carbonitrile Example 81B (179 mg, 0.40 mmol) was cyclized using a similar procedure described in Example 55C to give the title compound (cis isomer, 50 mg, 30%) and Example 82A (trans isomer). The analytical data for cis isomer is as follows: MS (ESI) m/z 414.10 (M–H)$^-$; $^1$H NMR (400 MHz, DMSO-D$^6$) δ ppm 1.15 (t, J=7.06 Hz, 3 H) 3.46–3.62 (m, 2 H) 3.90 (t, J=8.59 Hz, 1 H) 4.31–4.43 (m, 2 H) 5.34–5.41 (m, 2 H) 5.54 (m, 1 H) 5.75 (m, 1 H) 7.12 (m, 1 H) 7.24 (d, J=8.90 Hz, 1 H) 8.01 (s, 1 H) 8.25 (d, J=2.76 Hz, 1 H) 9.71 (s, 1 H) 10.96 (s, 1 H).

EXAMPLE 81D 18-chloro-13-ethoxy-11,12-cis-dihydroxy-2-oxo-2,3,11,12,13,14-hexahydro-1H,10H-8,4-epiazeno-9,15,1,3,6-benzodioxatriazacycloheptadecine-7-carbonitrile Example 81C (44.5 mg, 0.11 mmol) was oxidized using a similar procedure described in Example 55D to give the title compound (14.3 mg, 30%). MS (ESI) m/z 448.11 (M–H)$^-$; $^1$H NMR (400 MHz, DMSO-D$^6$) δ ppm 1.10 (t, J=6.90 Hz, 3 H) 3.47–3.58 (m, 2 H) 3.71 (d, J=7.06 Hz, 1 H) 3.78 (t, J=3.99 Hz, 1 H) 4.03 (dd, J=9.51, 2.76 Hz, 1 H) 4.18 (m, 1 H) 4.25–4.38 (m, 2 H) 4.91 (dd, J=11.51, 2.61 Hz, 1 H) 5.17 (dd, J=15.96, 5.52 Hz, 2 H) 7.11–7.20 (m, 2 H) 7.97 (d, J=2.45 Hz, 1 H) 7.99 (s, 1 H) 9.62 (s, 1 H) 10.89 (s, 1 H).

EXAMPLE 82

18-chloro-13-ethoxy-11,12-trans-dihydroxy-2-oxo-2, 3,11,12,13,14-hexahydro-1H,10H-8,4-epiazeno-9, 15,1,3,6-benzodioxatriazacycloheptadecine-7-carbonitrile

EXAMPLE 82A (trans) 18-chloro-13-ethoxy-2-oxo-2,3,13,14-tetrahydro-1H,10H-8,4-epiazeno-9,15,1,3,6-benzodioxatriazacycloheptadecine-7-carbonitrile The title compound (trans, 75 mg, 45%) was prepared using the same procedure described in Example 81C. MS (ESI) m/z 414.14 (M−H)$^−$; $^1$H NMR (400 MHz, DMSO-D$^6$) δ ppm 1.09 (t, J=7.06 Hz, 3 H) 3.39–3.56 (m, 2 H) 4.00 (m, 1 H) 4.11 (m, 1 H) 4.33 (dd, J=10.28, 3.84 Hz, 1 H) 4.94–5.03 (m, 2 H) 5.61 (dd, J=16.26, 6.75 Hz, 1 H) 5.90 (d, J=16.26 Hz, 1 H) 7.15 (m, 1 H) 7.21 (m, 1 H) 7.78 (d, J=2.15 Hz, 1 H) 8.00 (s, 1 H) 9.16 (s, 1 H) 10.89 (s, 1 H).

EXAMPLE 82B 18-chloro-13-ethoxy-11,12-trans-dihydroxy-2-oxo-2, 3,11,12,13,14-hexahydro-1H,10H-8,4-epiazeno-9, 15,1,3,6-benzodioxatriazacycloheptadecine-7-carbonitrile Example 82A (43.4 mg, 0.10 mmol) was oxidized using a similar procedure described in Example 55D to give the title compound (16.2 mg, 34%). MS (ESI) m/z 448.09 (M−H)$^−$; $^1$H NMR (400 MHz, DMSO-D$^6$) δ ppm 1.12 (t, J=6.90 Hz, 3 H) 3.46–3.59 (m, 2 H) 3.68 (d, J=7.06 Hz, 1 H) 3.85 (t, J=5.06 Hz, 1 H) 4.01–4.16 (m, 2 H) 4.37 (dd, J=10.13, 7.98 Hz, 1 H) 4.56–4.70 (m, 2 H) 5.27 (d, J=4.91 Hz, 1 H) 5.34 (d, J=5.22 Hz, 1 H) 7.14 (dd, J=8.90, 2.46 Hz, 1 H) 7.22 (m, 1 H) 8.00 (s, 1 H) 8.28 (d, J=2.46 Hz, 1 H) 10.14 (s, 1 H) 10.95 (s, 1 H).

EXAMPLE 83

(cis) 18-nitro-2-oxo-2,3,13,14-tetrahydro-1H,10H-8, 4-epiazeno-9,15,1,3,6-benzodioxatriazacycloheptadecine-7-carbonitrile

EXAMPLE 83A 3-(allyloxy)-5-aminopyrazine-2-carbonitrile

To a suspension of 95% NaH (3.27 g, 129.36 mmol) in dioxane (300 mL) under N$^2$ atmosphere was injected allyl alcohol (8.8 mL, 129.36 mmol). After the reaction was stirred for 20 minutes, Example 7D (10 g, 64.68 mmol) was added. The reaction mixture was stirred at 100° C. overnight, cooled and filtered. The precipitate was washed with ethyl acetate (100 mL×10). The filtrate was concentrated with silica gel (20 g) and purified by flash chromatography eluting with 50% ethyl acetate in hexanes (2 L) to give the title compound (8.2 g, 72%). MS (DCI) m/z 176.99 (M+H)$^+$; $^1$H NMR (300 MHz, CDCl$^3$) δ ppm 4.84–4.88 (m, 2 H) 4.99 (s, 2 H) 5.30 (m, 1 H) 5.43 (m, 1 H) 6.04 (m, 1 H) 7.58 (s, 1 H).

EXAMPLE 83B phenyl 6-(allyloxy)-5-cyanopyrazin-2-ylcarbamate

To a mixture of phenyl chloroformate (15.86 mL, 126.59 mmol) and pyridine (7.96 mL, 98.46 mmol) in dichloromethane (150 mL) at 0° C. under N$^2$ atmosphere was added Example 83A (12.39 g, 70.33 mmol) in anhydrous THF (50 mL) dropwise. The reaction mixture was gradually warmed to room temperature, then stirred at room temperature for 0.5 hour, and diluted with ethyl acetate (1.5 L). The resulting suspension was washed with brine (200 mL×5). The organic layer was dried over MgSO$^4$ and evaporated. The residue was recrystalized from 20% ethyl acetate in hexanes (100 mL) to give the title compound (12.94 g, 62%). MS (DCI) m/z 297.06 (M+H)$^+$; $^1$H NMR (300 MHz, CDCl$^3$) δ ppm 4.92 (d, J=5.43 Hz, 2 H) 5.36 (dd, J=10.51, 1.36 Hz, 1 H) 5.48 (dd, J=17.12, 1.53 Hz, 1 H) 6.06 (m, 1 H) 7.18–7.23 (m, 2 H) 7.31 (t, J=7.46 Hz, 1 H) 7.39–7.49 (m, 2 H) 7.60 (s, 1 H) 9.00 (s, 1 H).

EXAMPLE 83C

N-[6-(allyloxy)-5-cyanopyrazin-2-yl]-N'-(2-hydroxy-5-nitrophenyl)urea

2-Amino-4-nitro-phenol (1.38 g, 8.98 mmol) and Example 83B (2.66 g, 8.98 mmol) were coupled using a similar procedure described in Example 60C to give the title compound (3.1 g, 96%). MS (ESI) m/z 355.02 (M−H)$^−$; $^1$H NMR (300 MHz, DMSO-D$^6$) δ ppm 4.99 (d, J=5.43 Hz, 2 H) 5.35 (dd, J=10.51, 1.36 Hz, 1 H) 5.48 (m, 1 H) 6.12 (m, 1 H) 7.02 (d, J=9.16 Hz, 1 H) 7.89 (dd, J=8.99, 2.88 Hz, 1 H) 8.80 (s, 1 H) 9.05 (d, J=3.05 Hz, 1 H) 9.46 (s, 1 H) 10.72 (s, 1 H) 11.93 (s, 1 H)

EXAMPLE 83D

N-[6-(allyloxy)-5-cyanopyrazin-2-yl]-N'-[2-(but-3-enyloxy)-5-nitrophenyl]urea

The title compound (209 mg, 10%) was prepared using a similar procedure described in Example 55B by replacing allyl alcohol with 1-butenol and substituting Example 55A with Example 83C. MS (ESI) m/z 409.07 (M−H)$^−$; $^1$H NMR (300 MHz, DMSO-D$^6$) δ ppm 2.24–2.37 (m, 2 H) 4.33 (t, J=6.78 Hz, 2 H) 4.90 (d, J=5.42 Hz, 2 H) 5.00–5.52 (m, 4 H) 5.73–6.21 (m, 2 H) 7.40 (m, 1 H) 7.99 (m, 1 H) 8.84 (s, 1 H) 8.98 (m, 1 H) 9.07 (s, 1 H) 10.80 (s, 1 H)

EXAMPLE 83E (cis) 18-nitro-2-oxo-2,3,13,14-tetrahydro-1H,10H-8, 4-epiazeno-9,15,1,3,6-benzodioxatriazacycloheptadecine-7-carbonitrile Example 83D (209 mg, 0.51 mmol) was cyclized using a similar procedure described in Example 55C to give the title compound (cis isomer, 17.6 mg, 9%) and Example 102A (trans isomer, 13.5 mg, 8%). MS (ESI) m/z 381.16 (M−H)$^−$; $^1$H NMR (400 MHz, DMSO-D$^6$) δ ppm 2.53–2.59 (m, 2 H) 4.33 (t, J=5.52 Hz, 2 H) 5.37–5.42 (m, 2 H) 5.64–5.75 (m, 2 H) 7.37 (d, J=9.21 Hz, 1 H) 8.03 (dd, J=9.05, 2.92 Hz, 1 H) 8.05 (s, 1 H) 9.16 (d, J=2.76 Hz, 1 H) 9.88 (s, 1 H) 11.04 (s, 1 H).

EXAMPLE 84

18-ethoxy-2-oxo-2,3,11,14-tetrahydro-1H,10H-8,4-epiazeno-9,15,1,3,6-benzodioxatriazacycloheptadecine-7-carbonitrile

EXAMPLE 84A

2-[2-(allyloxy)-5-hydroxyphenyl]-1H-isoindole-1,3(2H)-dione

Example 73D (6.74 g, 12.60 mmol) was dissolved in THF (140 mL). TBAF (22.3 g, 85.2 mmol) was added. The reaction mixture was stirred at room temperature overnight. The solution was dried with silica gel powder (20 g). 20% Ethyl acetate in hexanes (1 L) and 3% methanol in ethyl acetate (3 L) were used to run flash chromatography to give the title compound (1.99 g, 54%). MS (ESI) m/z 296.02 (M+H)$^+$; $^1$H NMR (300 MHz, CD$^3$OD) δ ppm 4.52 (d, J=5.43 Hz, 2 H) 5.20 (dd, J=10.51, 1.36 Hz, 1 H) 5.34 (dd, J=17.29, 1.36 Hz, 1 H) 6.06 (m, 1 H) 6.53 (dd, J=8.82, 2.71 Hz, 1 H) 6.86 (d, J=8.82 Hz, 1 H) 7.51–7.77 (m, 4 H) 7.94 (d, J=6.78 Hz, 1 H).

EXAMPLE 84B

2-[2-(allyloxy)-5-ethoxyphenyl]-1H-isoindole-1,3(2H)-dione

A mixture of Example 84A (0.63 g, 2.13 mmol), iodoethane (0.68 mL, 8.52 mmol) and K$^2$CO$^3$ (1.47 g, 10.65 mmol) in acetone (50 mL) were stirred, and refluxed for 3 hours, and cooled. The solution was filtered, and dried with silica gel powder (10 g). 15% Ethyl acetate in hexanes (1 L) and 20% ethyl acetate in hexanes (1 L) were used to run flash chromatography. The title compound was obtained (320 mg, 46%). MS (DCI) m/z 324.07 (M+H)$^+$; $^1$H NMR (300 MHz, CDCl$^3$) δ ppm 1.39 (t, J=7.12 Hz, 3 H) 4.00 (q, J=7.12 Hz, 2 H) 4.46–4.55 (m, 2 H) 5.07–5.30 (m, 2 H) 5.88 (m, 1 H) 6.82 (dd, J=2.54, 0.85 Hz, 1 H) 6.93–6.96 (m, 2 H) 7.75–7.80 (m, 2 H) 7.94 (dd, J=5.42, 3.05 Hz, 2 H).

EXAMPLE 84C

2-(allyloxy)-5-ethoxyaniline

Example 84B (320 mg, 0.99 mmol) was dissolved in methanol (20 mL). H$^2$NNH$^2$ (0.10 mL, 3 mmol) was added. The reaction mixture was stirred at room temperature for 3 hours. The solvents were removed via a vacuum pump. The residue was dissolved in acetone (10 mL). The solution was dried with silica gel powder (8 g). 15% Ethyl acetate in hexanes (2 L) was used to run flash chromatography to give the title compound (167.2 mg, 88%). MS (APCI) m/z 194 (M+H)$^+$; $^1$H NMR (400 MHz, CDCl$^3$) δ ppm 1.36 (t, J=6.90 Hz, 3 H) 3.94 (q, J=6.96 Hz, 2 H) 4.50 (d, J=5.52 Hz, 2 H) 5.25 (dd, J=10.43, 1.53 Hz, 1 H) 5.39 (dd, J=17.18, 1.53 Hz, 1 H) 6.06 (m, 1 H) 6.26 (dd, J=8.59, 2.76 Hz, 1 H) 6.40 (d, J=2.76 Hz, 1 H) 6.71 (d, J=8.90 Hz, 1 H).

EXAMPLE 84D

N-[2-(allyloxy)-5-ethoxyphenyl]-N'-[6-(but-3-enyloxy)-5-cyanopyrazin-2-yl]urea Example 84C (167.2 mg, 0.87 mmol) and Example 7F (268.2 mg, 0.87 mmol) were coupled using a similar procedure described in Example 60C to give the title compound (332 mg, 93%). MS (ESI) m/z 408.22 (M−H)$^-$; $^1$H NMR (500 MHz, DMSO-D$^6$) δ ppm 1.31 (t, J=7.02 Hz, 3 H) 2.54 (q, J=6.71 Hz, 2 H) 3.95 (q, J=7.02 Hz, 2 H) 4.46 (t, J=6.71 Hz, 2 H) 4.61 (d, J=5.49 Hz, 2 H) 5.11 (dd, J=10.37, 1.53 Hz, 1 H) 5.18 (dd, J=17.24, 1.68 Hz, 1 H) 5.28 (dd, J=10.53, 1.37 Hz, 1 H) 5.41 (dd, J=17.24, 1.68 Hz, 1 H) 5.88 (m, 1 H) 6.07 (m, 1 H) 6.56 (dd, J=9.00, 2.90 Hz, 1 H) 6.96 (d, J=8.85 Hz, 1 H) 7.78 (d, J=2.75 Hz, 1 H) 8.86 (s, 1 H) 8.97 (s, 1 H) 10.69 (s, 1 H).

EXAMPLE 84E

18-ethoxy-2-oxo-2,3,11,14-tetrahydro-1H,10H-8,4-epiazeno-9,15,1,3,6-benzodioxatriazacycloheptadecine-7-carbonitrile Example 84D (332 mg, 0.81 mmol) was cyclized using a similar procedure described in Example 55C to give the title compound (192.5 mg, 62%). MS (ESI) m/z 380.18 (M−H)$^-$; $^1$H NMR (500 MHz, DMSO-D$^6$) δ ppm 1.31 (t, J=6.87 Hz, 3 H) 2.69 (q, J=7.63 Hz, 2 H) 3.95 (q, J=6.92 Hz, 2 H) 4.61 (d, J=7.32 Hz, 2 H) 4.69 (t, J=7.32 Hz, 2 H) 5.98 (m, 1 H) 6.08 (m, 1 H) 6.62 (dd, J=9.00, 2.90 Hz, 1 H) 7.07 (d, J=8.85 Hz, 1 H) 7.71 (d, J=3.05 Hz, 1 H) 7.98 (s, 1 H) 10.26 (s, 1 H) 10.88 (s, 1 H).

EXAMPLE 85

18-chloro-17-(ethylamino)-2-oxo-2,3,11,12,13,14-hexahydro-1H,10H-8,4-epiazeno-9,15,1,3,6-benzodioxatriazacycloheptadecine-7-carbonitrile The desired product (9.6 mg, 30%) was prepared using a similar procedure described in Example 28 by replacing 3-pyridine carboxylaldehyde with acetylaldehyde. MS (APCI) m/z 417.29 (M+H)$^+$; $^1$H NMR (400 MHz, DMSO-D$^6$) δ ppm 1.17 (t, J=7.06 Hz, 3 H) 1.54–1.60 (m, 2 H) 1.76–1.83 (m, 2 H) 1.90–1.98 (m, 2 H) 3.14–3.22 (m, 2 H) 4.18 (t, J=5.06 Hz, 2 H) 4.56 (t, J=8.29 Hz, 2 H) 5.02 (t, J=5.68 Hz, 1 H) 6.39 (s, 1 H) 7.93 (s, 1 H) 7.96 (s, 1 H) 9.66 (s, 1 H) 10.74 (s, 1 H).

EXAMPLE 86

17-(butylamino)-18-chloro-2-oxo-2,3,11,12,13,14-hexahydro-1H,10H-8,4-epiazeno-9,15,1,3,6-benzodioxatriazacycloheptadecine-7-carbonitrile The desired product (12.8 mg, 52%) was prepared using a similar procedure described in Example 28 by replacing 3-pyridine carboxylaldehyde with butyraldehyde. MS (APCI) m/z 445.64 (M+H)$^+$; $^1$H NMR (400 MHz, DMSO-D$^6$) δ ppm 0.92 (t, J=7.36 Hz, 3 H) 1.31–1.42 (m, 2 H) 1.51–1.63 (m, 4 H) 1.78–1.84 (m, 2 H) 1.92–2.00 (m, 2 H) 3.15 (q, J=6.44 Hz, 2 H) 4.19 (t, J=5.22 Hz, 2 H) 4.58 (t, J=7.67 Hz, 2 H) 5.01 (t, J=5.83 Hz, 1 H) 6.40 (s, 1 H) 7.94 (s, 1 H) 7.97 (s, 1 H) 9.68 (s, 1 H) 10.77 (s, 1 H).

EXAMPLE 87

17-chloro-2-oxo-2,3,10,11,12,13-hexahydro-1H,8,4-epiazeno-9,14,1,3,6-benzodioxatriazacyclohexadecine-7-carbonitrile A mixture of palladium-carbon (5%, 2 mg) and Example 55C (10 mg, 0.028 mmol) in THF (25 mL) was stirred under hydrogen atmosphere for 3 hours. Palladium-carbon was removed by filtration through Celite. The filtrate was concentrated, and the residue was washed with methanol and dried to provide the title compound (7.5 mg, 75%). MS (ESI) m/z: 357.91 (M–H)$^-$; $^1$H NMR (500 MHz, DMSO-D$^6$) δ ppm 1.85–1.91 (m, 2 H) 2.00–2.06 (m, 2 H) 4.17 (t, J=5.49 Hz, 2 H) 4.75 (t, J=7.32 Hz, 2 H) 7.09 (dd, J=8.85, 2.14 Hz, 1 H) 7.18 (d, J=8.54 Hz, 1 H) 7.94 (s, 1 H) 8.34 (s, 1 H) 10.83 (s, 1 H) 11.05 (s, 1 H).

EXAMPLE 88

18-chloro-14-methyl-2-oxo-2,3,11,14-tetrahydro-1H,10H-8,4-epiazeno-9,15,1,3,6-benzodioxatriazacycloheptadecine-7-carbonitrile

EXAMPLE 88A

N-[6-(but-3-enyloxy)-5-cyanopyrazin-2-yl]-N'-(5-chloro-2-hydroxyphenyl)urea

A solution of 2-amino-4-chlorophenol (1.39 g, 9.67 mmol) and Example 7F (2 g, 6.45 mmol) in NMP was heated at 80° C. for 24 hours, cooled and diluted with ethyl acetate (250 mL). The resulting mixture was washed with 10% HCl, and then water. The organic layer was dried over MgSO$^4$, concentrated and dried to give the desired product (1.87 g, 80%). MS (DCI) m/z 377.07 (M+NH$^4$)$^+$.

EXAMPLE 88B

N-[6-(but-3-enyloxy)-5-cyanopyrazin-2-yl]-N'-{5-chloro-2-[(1-methylprop-2-enyl)oxy]phenyl}urea To a mixture of Example 88A (0.5 g, 1.39 mmol), polymer-supported triphenyl phosphine (927 mg, 2.78 mmol) and 3-buten-2-ol (0.481 mL, 5.56 mmol) in THF (20 ml) was added di-tert-butyl azodicarboxylate (640.2 mg, 2.78 mmol). The reaction mixture was stirred overnight, and the insoluble material was removed by filtration. The filtrate was concentrated, and the residue was purified by flash chromatography eluting with 30% ethyl acetate in hexane. The desired product (477 mg, 83%) was obtained. MS (ESI) m/z 414.01 (M+H)$^+$; $^1$H NMR (400 MHz, DMSO-D$^6$) δ ppm 1.45 (d, J=6.44 Hz, 3 H) 2.55 (q, J=6.75 Hz, 2 H) 4.46 (t, J=6.75 Hz, 2 H) 5.02 (m, 1 H) 5.11 (m, 1 H) 5.16–5.21 (m, 2 H) 5.29 (d, J=17.18 Hz, 1 H) 5.83–5.98 (m, 2 H) 7.02 (dd, J=8.92, 2.45 Hz, 1 H) 7.09 (d, J=8.92, 1 H) 8.19 (d, J=2.45 Hz, 1 H) 8.88 (s, 1 H) 8.94 (s, 1 H) 10.76 (s, 1 H).

EXAMPLE 88C 18-chloro-14-methyl-2-oxo-2,3,11,14-tetrahydro-1H,10H-8,4-epiazeno-9,15,1,3,6-benzodioxatriazacycloheptadecine-7-carbonitrile A mixture of Example 88B (270 mg, 0.65 mmol) and Grubbs Catalyst (2$^{nd}$ generation, 55 mg, 0.065 mmol) in CH$^2$Cl$^2$ (330 mL) was stirred at room temperature for 36 hours, and then DMSO (0.461 mL, 6.5 mmol) was added. The reaction mixture was further stirred for 24 hours, concentrated. The residue was purified by flash chromatography eluting with 9% of ethyl acetate in dichloromethane to provide the desired product (158 mg, 63%). MS (DCI/NH$^3$) m/z 386.1 (M+H)$^+$; $^1$H NMR (500 MHz, DMSO-D$^6$) δ ppm 1.37 (d, J=6.24 Hz, 3 H) 2.42 (m, 1 H) 2.49 (m, 1 H) 4.34 (m, 1 H) 4.74 (m, 1 H) 4.95 (m, 1 H) 5.81 (dd, J=15.91, 5.30 Hz, 1 H) 5.98 (m, 1 H) 7.17 (dd, J=8.73, 2.81 Hz, 1 H) 7.28 (d, J=9.05 Hz, 1 H) 7.85 (d, J=2.50 Hz, 1 H) 8.03 (s, 1 H) 9.34 (s, 1 H) 10.80 (s, 1 H).

EXAMPLE 89

18-bromo-16-fluoro-12,13-dihydroxy-2-oxo-2,3,11,12,13,14-hexahydro-1H,10H-8,4-epiazeno-9,15,1,3,6-benzodioxatriazacycloheptadecine-7-carbonitrile

EXAMPLE 89A 2-(allyloxy)-5-bromo-1-fluoro-3-nitrobenzene

A mixture of 4-bromo-6-fluoro-2-nitrophenol (2 g, 8.49 mmol), allyl bromide (0.88 mL, 10.07 mmol) and K$^2$CO$^3$ (2.34 g, 16.98 mmol) in DMF (20 mL) was stirred at 45° C. overnight. Inorganic salts were filtered off, and the filtrate was concentrated to provide the crude product, which was directly used for next step without further purification. MS (DCI/NH$^3$) m/z 245.92 (M+H)$^+$; $^1$H NMR (400 MHz, DMSO-D$^6$) δ ppm 4.70 (d, J=6.14 Hz, 2 H) 5.27 (d, J=10.43 Hz, 1 H) 5.37 (dd, J=17.18, 1.53 Hz, 1 H) 5.92–6.02 (m, 1 H) 8.03–8.06 (m, 2 H).

EXAMPLE 89B 2-(allyloxy)-5-bromo-3-fluoroaniline

A mixture of Example 89A (1.3 g, 4.71 mmol), tin chloride dihydrate (5.3 g, 23.5 mmol) and triethylamine (13.1 mL, 94.2 mmol) in ethanol (50 mL) was heated at 70° C. for 6 hours, cooled. The insoluble material was filtered off and extensively washed with ethyl acetate. The combined filtrate was concentrated, and the residue was purified by flash chromatography eluting with 5% ethyl acetate in dichloromethane to provide the desired product (638 mg, 55%). MS (DCI/NH$^3$) m/z 247.82 (M+H)$^+$; $^1$H NMR (500 MHz, DMSO-D$_6$) δ ppm 4.41 (d, J=5.93 Hz, 2 H) 5.20 (dd, J=10.45, 1.72 Hz, 1 H) 5.30 (dd, J=17.31, 1.72 Hz, 1 H) 5.43 (s, 2 H) 6.03 (m, 1 H) 6.56 (dd, J=10.29, 2.50 Hz, 1 H) 6.66 (dd, J=2.34, 1.72 Hz, 1 H).

EXAMPLE 89C

N-[2-(allyloxy)-5-bromo-3-fluorophenyl]-N'-[6-(but-3-enyloxy)-5-cyanopyrazin-2-yl]urea A solution of Example 89B (103 mg, 0.42 mmol) and Example 7F (130 mg, 0.42 mmol) in DMF was heated at 80° C. for 24 hours, cooled and concentrated. The residue was triturated with a mixture of hexane and ethyl acetate to give the desired product (110 mg, 56%). MS (ESI) m/z 461.95 (M–H)$^-$, 464.0 (M+H)$^+$; $^1$H NMR (500 MHz, DMSO-D$^6$) δ ppm 2.55 (q, J=6.61 Hz, 2 H) 4.47 (t, J=6.71 Hz, 2 H) 4.62 (d, J=6.10 Hz, 2 H) 5.12 (d, J=10.37 Hz, 1 H) 5.19 (dd, J=17.24, 1.68 Hz, 1 H) 5.28 (d, J=10.07 Hz, 1 H) 5.35 (dd, J=17.24, 1.37 Hz, 1 H) 5.88 (m, 1 H) 6.06 (m, 1 H) 7.30 (dd, J=10.53, 2.29 Hz, 1 H) 8.24 (d, J=1.83 Hz, 1 H) 8.89 (s, 1 H) 9.22 (s, 1 H) 10.69 (s, 1 H).

EXAMPLE 89D 18-bromo-16-fluoro-2-oxo-2,3,11,14-tetrahydro-1H,10H-8,4-epiazeno-9,15,1,3,6-benzodioxatriazacycloheptadecine-7-carbonitrile A mixture of Example 89C (100 mg, 0.22 mmol) and Grubbs Catalyst (2$^{nd}$ generation, 18 mg, 0.022 mmol) in CH$^2$Cl$^2$ (150 mL) was stirred at room temperature for 6 hours and concentrated. The residue was purified by flash chromatography eluting with 9% of ethyl acetate in dichloromethane to provide the desired product (60 mg, 64%). MS (ESI) m/z 433.95 (M–H)⁻; ¹H NMR (500 MHz, DMSO-D⁶) δ ppm 2.68 (q, J=7.93 Hz, 2 H) 4.59 (d, J=7.32 Hz, 2 H) 4.65–4.69 (m, 2 H) 6.02 (m, 1 H) 6.09 (m, 1 H) 7.38 (dd, J=10.37, 2.14 Hz, 1 H) 8.02 (s, 1 H) 8.28 (m, 1 H) 10.25 (s, 1 H) 11.06 (s, 1 H).

EXAMPLE 89E 18-bromo-16-fluoro-12,13-dihydroxy-2-oxo-2,3,11, 12,13,14-hexahydro-1H,10H-8,4-epiazeno-9,15,1,3, 6-benzodioxatriazacycloheptadecine-7-carbonitrile Example 89D (20 mg, 0.046 mmol) and N-methylmorpholine-N-oxide (16 mg, 0.14 mmol) were dissolved in a mixture of THF (10 mL) and H₂O (1.1 mL). The resulting mixture was treated with 2.5% (W %) of OsO⁴ in 2-methyl-2-propanol (0.08 mL) at 0° C. The reaction mixture was stirred at room temperature for 5 hours and concentrated. The white precipitates were collected by filtration and washed with water thoroughly. The title compound (19.2 mg, 89%) was obtained as white solid. MS (ESI) m/z: 467.40 (M–H)⁻; ¹H NMR (400 MHz, DMSO-D⁶) δ ppm 1.94 (m, 1 H) 2.20 (m, 1 H) 3.76–3.88 (m, 2 H) 4.07 (m, 1 H) 4.24 (m, 1 H) 4.62 (m, 1 H) 4.75–4.83 (m, 2 H) 5.01 (d, J=5.22 Hz, 1 H) 7.37 (dd, J=11.05, 2.45 Hz, 1 H) 8.00 (s, 1 H) 8.20 (s, 1 H) 10.09 (s, 1 H) 11.00 (s, 1 H)

EXAMPLE 90

19-chloro-2-oxo-2,3,10,11,14,15-hexahydro-1H-8,4-epiazeno-9,16,1,3,6-benzodioxatriazacyclooctadecine-7-carbonitrile

EXAMPLE 90A 1-(but-3-enyloxy)-4-chloro-2-nitrobenzene

To a solution of 3-butene-ol (1.08 mL, 12.53 mmol) in THF (30 mL) at 0° C. was added NaH (60%, 592 mg, 14.81 mmol). The mixture was stirred for 30 minutes, and 4-chloro-1-fluoro-2-nitrobenzene (2 g, 11.39 mmol) in THF (5 mL) was added dropwise. The reaction mixture was further stirred at 0° C. for 2 hours, poured into ice-water and extracted with ethyl acetate. The organic layer was dried over MgSO⁴ and concentrated to give the desired product (2.5 g, 97%). MS (DCI/NH³) m/z: 244.95 (M+H)⁺; ¹H NMR (400 MHz, DMSO-D⁶) δ ppm 2.47 (q, J=6.55 Hz, 2 H) 4.22 (t, J=6.60 Hz, 2 H) 5.08 (d, J=10.13 Hz, 1 H) 5.15 (dd, J=17.18, 1.84 Hz, 1 H) 5.80–5.91 (m, 1 H) 7.42 (d, J=9.21 Hz, 1 H) 7.70 (dd, J=9.21, 2.76 Hz, 1 H) 8.00 (d, J=2.76 Hz, 1 H)

EXAMPLE 90B 2-(but-3-enyloxy)-5-chloroaniline

A mixture of Example 90A (1 g, 4.39 mmol), iron powder (2.46 g, 43.9 mmol) and NH⁴Cl (117 mg, 2.20 mmol) in ethanol (36 mL) and water (9 mL) was heated at 80° C. for 5 hours. The insoluble material was filtered off, and the filtrate was concentrated. The residue was purified by flash chromatography eluting with 50% dichloromethane in hexane to provide the desired product (750 mg, 86%) as yellow solid. MS (APCI) m/z 198.25 (M+H)⁺; ¹H NMR (400 MHz, DMSO-D⁶) δ ppm 2.47 (q, J=6.85 Hz, 2 H) 3.96 (t, J=6.60 Hz, 2 H) 4.94 (s, 2 H) 5.08 (d, J=10.43 Hz, 1 H) 5.16 (dd, J=17.18, 2.15 Hz, 1 H) 5.92 (m, 1 H) 6.47 (dd, J=8.59, 2.76 Hz, 1 H) 6.64 (d, J=2.76 Hz, 1 H) 6.76 (d, J=8.29 Hz, 1 H)

EXAMPLE 90C

N-[2-(but-3-enyloxy)-5-chlorophenyl]-N'-[6-(but-3-enyloxy)-5-cyanopyrazin-2-yl]urea A mixture of Example 90B (710 mg, 3.59 mmol) and Example 7F (1.11 g, 3.59 mmol) in DMF (10 mL) was heated at 80° C. for 24 hours. The solvent was removed, and the residue was triturated with ethyl acetate to provide the desired product (1.32 g, 89%). MS (ESI) m/z 414.15 (M+H)⁺, 412.10 (M–H)—; ¹H NMR (400 MHz, DMSO-D⁶) δ ppm 2.53–2.58 (m, 4 H) 4.15 (t, J=6.75 Hz, 2 H) 4.46 (t, J=6.60 Hz, 2 H) 5.11 (t, J=10.43 Hz, 2 H) 5.18 (dd, J=17.18, 1.23 Hz, 2 H) 5.83–5.99 (m, 2 H) 7.04–7.12 (m, 2 H) 8.19 (d, J=2.45 Hz, 1 H) 8.91 (s, 2 H) 10.72 (s, 1 H).

EXAMPLE 90D (cis) 19-chloro-2-oxo-2,3,10,11,14,15-hexahydro-1H-8,4-epiazeno-9,16,1,3,6-benzodioxatriazacyclooctadecine-7-carbonitrile and (trans) 19-chloro-2-oxo-2,3,10,11,14,15-hexahydro-1H-8,4-epiazeno-9,16,1,3,6-benzodioxatriazacyclooctadecine-7-carbonitrile A mixture of Example 90C (500 mg, 1.21 mmol) and Grubbs Catalyst (2$^{nd}$ generation, 151 mg, 0.18 mmol) in CH₂Cl₂ (600 mL) was stirred at room temperature overnight and concentrated. The residue was purified by flash chromatography eluting with 9% of ethyl acetate in dichloromethane to provide cis conformation product (231 mg, 50%) and trans conformation product (58 mg, 12%). Analytical data for Example 90: MS (ESI) m/z 384.14 (M–H)⁻; ¹H NMR (400 MHz, DMSO-D⁶) δ ppm 2.52–2.58 (m, 4 H) 4.16 (t, J=4.91 Hz, 2 H) 4.49 (d, J=8.29 Hz, 2 H) 5.55–5.67 (m, 2 H) 7.14 (dd, J=8.90, 2.45 Hz, 1 H) 7.27 (d, J=8.90 Hz, 1 H) 7.96 (d, J=2.45 Hz, 1 H) 8.00 (s, 1 H) 9.77 (s, 1 H) 10.95 (s, 1 H). Analytical data for Example 90D: MS (ESI) m/z 384.11 (M–H)⁻; ¹H NMR (400 MHz, DMSO-D⁶) δ ppm 2.34–2.45 (m, 4 H) 4.10 (t, J=5.06 Hz, 2 H) 4.56 (d, J=4.91 Hz, 2 H) 5.54–5.57 (m, 2 H) 7.07 (d, J=8.90 Hz, 1 H) 7.19 (dd, J=8.90, 2.45 Hz, 1 H) 7.73 (d, J=2.76 Hz, 1 H) 8.00 (s, 1 H) 9.02 (s, 1 H) 10.87 (s, 1 H)

EXAMPLE 91

(12R,13S)-19-chloro-12,13-cis-dihydroxy-2-oxo-2,3, 10,11,12,13,14,15-octahydro-1H-8,4-epiazeno-9,16, 1,3-benzodioxadiazacyclooctadecine-7-carbonitrile The desired product (19.6 mg, 90%) was prepared using a similar procedure described in Example 3 by replacing Example 1 with the cis product from Example 90D. MS (ESI) m/z 418.09 (M–H)⁻; ¹H NMR (500 MHz, DMSO-D⁶) δ ppm 1.83–1.91 (m, 3 H) 2.04 (m, 1 H) 3.58 (m, 1 H) 3.71 (m, 1 H) 4.01 (m, 1 H) 4.22 (m, 1 H) 4.46 (m, 1 H) 4.61–4.68 (m, 3 H) 7.15–7.19 (m, 2 H) 7.86 (d, J=1.53 Hz, 1 H) 8.00 (s, 1 H) 9.49 (s, 1 H) 10.94 (s, 1 H)

EXAMPLE 92

(12R,13S)-19-chloro-12,13-trans-dihydroxy-2-oxo-2,3,10,11,12,13,14,15-octahydro-1H-8,4-epiazeno-9,16,1,3-benzodioxadiazacyclooctadecine-7-carbonitrile The desired product (20 mg, 92%) was prepared using a similar procedure described in Example 3 by replacing Example 1 with the trans product from Example 90D. MS (ESI) m/z 418.16 (M−H)$^-$; $^1$H NMR (400 MHz, DMSO-D$^6$) δ ppm 1.73 (m, 1 H) 1.84–2.00 (m, 2 H) 2.23 (m, 1 H) 3.38 (m, 1 H) 3.53 (m, 1 H) 4.00 (t, J=7.36 Hz, 1 H) 4.35 (t, J=8.13 Hz, 1 H) 4.59 (t, J=8.13 Hz, 2 H) 4.72 (dd, J=6.44, 4.60 Hz, 2 H) 7.17 (s, 2 H) 7.88 (s, 1H) 8.01 (s, 1H) 9.55 (s, 1 H) 10.92 (s, 1 H)

EXAMPLE 93

19-chloro-2-oxo-2,3,10,11,12,13,14,15-octahydro-1H-8,4-epiazeno-9,16,1,3,6-benzodioxatriazacyclooctadecine-7-carbonitrile A mixture of 5% palladium-carbon (5 mg, 0.0024 mmol) and Example 90 (40 mg, 0.10 mmol) in THF (50 mL) was stirred under hydrogen atmosphere for 7 hours. Palladium-carbon was removed by filtration through Celite. The filtrate was concentrated, and the residue was washed with methanol. The title compound was obtained in quantitative yield. MS (ESI) m/z: 386.08 (M−H)$^-$; $^1$H NMR (400 MHz, DMSO-D$^6$) δ ppm 1.43–1.59 (m, 4 H) 1.74–1.92 (m, 4 H) 4.15 (s, 2 H) 4.52 (t, J=6.90 Hz, 2 H) 7.15 (s, 2 H) 7.96 (s, 1 H) 8.00 (s, 1 H) 9.61 (s, 1 H) 10.91 (s, 1 H).

EXAMPLE 94

18-methyl-2-oxo-2,3,11,14-tetrahydro-1H,10H-8,4-epiazeno-9,15,1,3,6-benzodioxatriazacycloheptadecine-7-carbonitrile

EXAMPLE 94A 1-(allyloxy)-4-methyl-2-nitrobenzene

To a mixture of 4-methyl-2-nitro-phenol (1.50 g, 9.80 mmol) and K$^2$CO$^3$ (2.03 g, 14.7 mmol) in acetone (23 mL) was added allyl bromide (1.24 ml, 14.7 mmol). The reaction mixture was stirred at room temperature overnight. It was then heated at 40° C. for 6 hrs. Inorganic salts were filtered and washed with acetone. The filtrate was concentrated and the residue was purified by flash chromatograph eluting with hexane/EtOAc (95:5) to give 1.67 g (88%) of the desired product. MS (DCI/NH$^3$) m/z: 211.0 (M+NH$^4$)$^+$; $^1$H NMR (300 MHz, DMSO-D6) δ ppm 2.30 (s, 3 H) 4.67–4.75 (m, 2 H) 5.27 (m, 1 H) 5.42 (m, 1 H) 5.97 (m, 1 H) 7.24 (d, J=8.48 Hz, 1 H) 7.45 (dd, J=8.65, 2.20 Hz, 1 H) 7.69 (d, J=2.37 Hz, 1 H).

EXAMPLE 94B 2-(allyloxy)-5-methylaniline

A mixture of Example 94A (1.50 g, 7.76 mmol), Fe (4.35 g, 77.6 mmol), NH$^4$Cl (0.208 g, 3.90 mmol), and H$^2$O (5 ml) in EtOH (20 ml) was heated at 90° C. for 6 hours. The reaction mixture was cooled and filtered through celite. The filtrate was concentrated and the residue was purified by flash chromatography eluting with hexane/ethyl acetate (95:5) to give 0.542 g (43%) of the desired product. MS (ESI) m/z: 163.8 (M+H)$^+$; $^1$H NMR (300 MHz, CD$^3$OD) δ ppm 2.17 (s, 3 H) 4.51 (ddd, J=5.26, 1.53, 1.53 Hz, 2 H) 5.23 (m, 1 H) 5.39 (m, 1 H) 6.08 (m, 1 H) 6.47 (dd, J=8.14, 1.70 Hz, 1 H) 6.60 (d, J=2.03 Hz, 1 H) 6.69 (d, J=8.14 Hz, 1 H).

EXAMPLE 94C

N-[2-(allyloxy)-5-methylphenyl]-N'-[6-(but-3-enyloxy)-5-cyanopyrazin-2-yl]urea

Example 94B (0.2 g, 1.13 mmol) and Example 7F (0.418 g, 1.35 mmol) in DMF (13 mL) were heated at 75° C. for 5 hours. The reaction mixture was cooled, diluted with ethyl acetate, and washed with 50% brine and water. The organic layer was dried over MgSO$^4$ and concentrated. The crude product was purified by flash chromatography eluting with hexane/ethyl acetate (7:3 to 5:5) to give 76.2 mg of the desired product. MS (ESI) m/z: 380.0 (M+H)$^+$; $^1$H NMR (300 MHz, CDCl$^3$) δ ppm 2.35 (s, 3 H) 2.56 (td, J=6.44, 6.44 Hz, 2 H) 4.48 (t, J=6.61 Hz, 2 H) 4.59 (d, J=6.90 Hz, 2 H) 5.06–5.19 (m, 2 H) 5.25–5.39 (m, 2 H) 5.83 (m, 1 H) 5.99 (m, 1 H) 6.83 (m, 1 H) 6.92 (m, 1 H) 7.89 (s, 1 H) 8.15 (s, 1 H) 8.42 (s, 1 H) 9.56 (s, 1 H).

EXAMPLE 94D 18-methyl-2-oxo-2,3,11,14-tetrahydro-1H,10H-8,4-epiazeno-9,15,1,3,6-benzodioxatriazacycloheptadecine-7-carbonitrile Example 94C (40 mg, 0.11 mmol) in CH$^2$Cl$^2$ (55 mL) was treated with Grubbs II catalyst (13.4 mg, 0.016 mmol). The reaction mixture was stirred at 40° C. overnight. Solvent was evaporated and the residue was purified by flash chromatography eluting with hexane/ethyl acetate/dichloromethane (7.5:2:0.5 to 6:3:1) to give 4.0 mg of the desired product. MS (ESI) m/z: 351.7 (M+H)$^+$; $^1$H NMR (400 MHz, CDCl$^3$) δ ppm 2.35 (s, 3 H) 2.76 (td, J=7.06, 7.06 Hz, 2 H) 4.60 (d, J=6.75 Hz, 2 H) 4.76 (t, J=7.36 Hz, 2 H) 5.98–6.13 (m, 2 H) 6.82–6.95 (m, 2 H) 7.93 (s, 1 H) 7.98 (s, 1 H) 9.40 (s, 1 H) 10.43 (s, 1 H).

EXAMPLE 95

18-methyl-2-oxo-2,3,11,12,13,14-hexahydro-1H,10H-8,4-epiazeno-9,15,1,3,6-benzodioxatriazacycloheptadecine-7-carbonitrile To a solution of Example 94D (21.2 mg, 0.0603 mmol) in THF (4 mL) was added 10% Pd/C (5.3 mg). The reaction mixture was stirred under hydrogen (a balloon was used) for 2.5 hours. The solvent was evaporated and the residue was treated with DMSO/MeOH (1:1). The solid was filtered and washed with DMF, the filtrate was purified using reversed-phase preparative HPLC to give 2.4 mg of the desired product. LC/MS (APCI) m/z: 354.7 (M+H)$^+$; $^1$H NMR (500 MHz, DMSO-D6) δ ppm 1.51–1.64 (m, 2 H) 1.75–1.85 (m, 2 H) 1.89–2.01 (m, 2 H) 2.25 (s, 3 H) 4.14 (t, J=5.03 Hz, 2 H) 4.61 (t, J=8.00 Hz, 2 H) 6.88 (d, J=8.24 Hz, 1 H) 6.99 (d, J=8.24 Hz, 1 H) 7.91 (s, 1 H) 7.99 (s, 1 H) 9.85 (s, 1 H) 10.83 (s, 1 H).

EXAMPLE 96

16-bromo-18-methyl-2-oxo-2,3,11,14-tetrahydro-1H,10H-8,4-epiazeno-9,15,1,3,6-benzodioxatriazacycloheptadecine-7-carbonitrile

EXAMPLE 96A 2-(allyloxy)-1-bromo-5-methyl-3-nitrobenzene

To a mixture of 2-bromo-4-methyl-6-nitrophenol (7.00 g, 30.2 mmol), $K_2CO_3$ (6.26 g, 45.3 mmol) in acetone (105 mL) was added allyl bromide (3.80 ml, 45.3 mmol). The reaction mixture was stirred at room temperature overnight. It was then heated at 40° C. for 5 hrs. Inorganic salts were filtered and washed with acetone. The filtrate was concentrated to give 7.74 g (94%) of the desired product. MS (DCI/$NH_3$) m/z: 289.0 $(M+NH_4)^+$; $^1H$ NMR (300 MHz, $CD_3OD$) δ ppm 2.37 (s, 3 H) 4.61 (d, J=6.10 Hz, 2 H) 5.26 (dd, J=10.51, 1.80 Hz, 1 H) 5.39 (dd, J=17.29, 1.80 Hz, 1 H) 6.09 (m, 1 H) 7.63 (s, 1 H) 7.74 (s, 1 H).

EXAMPLE 96B 2-(allyloxy)-3-bromo-5-methylaniline

A mixture of Example 96A (7.74 g, 28.5 mmol), Fe (15.9 g, 285 mmol), $NH_4Cl$ (0.762 g, 14.3 mmol), and $H_2O$ (18.4 mL) in EtOH (73 mL) was heated at 90° C. for 5 hours. The reaction mixture was cooled and filtered through celite. The reaction mixture was concentrated, treated with ethyl acetate, and washed with water and brine. The organic layer was dried over $MgSO_4$ and concentrated. The crude product was purified by flash chromatography eluting with hexane/ethyl acetate (95:5) to give 4.62 g (67%) of the desired product. MS (ESI) m/z: 241.8 $(M+H)^+$; $^1H$ NMR (300 MHz, $CDCl_3$) δ ppm 2.20 (s, 3 H) 4.46 (ddd, J=5.76, 1.36, 1.36 Hz, 2 H) 5.25 (m, 1 H) 5.45 (m, 1 H) 6.13 (m, 1 H) 6.51 (d, J=2.03 Hz, 1 H) 6.75 (d, J=2.03 Hz, 1 H).

EXAMPLE 96C

N-[2-(allyloxy)-3-bromo-5-methylphenyl]-N'-[6-(but-3-enyloxy)-5-cyanopyrazin-2-yl]urea Example 96B (3.75 g, 15.5 mmol) and Example 7F (3.58 g, 11.5 mmol) in DMF (100 mL) were heated at 85° C. overnight. The reaction mixture was cooled, diluted with ethyl acetate, and washed with 50% brine and water. The organic layer was dried over $MgSO_4$ and concentrated. The crude product was purified by flash chromatography eluting with hexane/ethyl acetate/dichloromethane (9:1:2 to 8:1:2) to give 2.55 g (48%) of the desired product. MS (ESI) m/z: 457.9 $(M+H)^+$; $^1H$ NMR (300 MHz, $CDCl_3$) δ ppm 2.34 (s, 3 H) 2.58 (td, J=6.78, 6.78 Hz, 2 H) 4.45 (d, J=6.44 Hz, 2 H) 4.54 (t, J=6.95 Hz, 2 H) 5.04–5.33 (m, 4 H) 5.76–6.10 (m, 2 H) 7.17 (s, 1 H) 7.85 (s, 1 H) 8.07 (s, 1 H) 8.21 (s, 1 H) 10.01 (s, 1 H).

EXAMPLE 96D 16-bromo-18-methyl-2-oxo-2,3,11,14-tetrahydro-1H,10H-8,4-epiazeno-9,15,1,3,6-benzodioxatriazacycloheptadecine-7-carbonitrile Example 96C (1.55 g, 3.38 mmol) in $CH_2Cl_2$ (1600 mL) was treated with Grubbs II catalyst (212 mg, 0.34 mmol). The reaction mixture was stirred at 40° C. overnight. Solvent was evaporated and the residue was purified by flash chromatography eluting with dichloromethane/ethyl acetate (95:5 to 85:15) to give 1.05 g (72%) of the desired product. MS (ESI) m/z: 428.0 $(M-H)^+$; $^1H$ NMR (300 MHz, $CDCl_3$) δ ppm 2.35 (s, 3 H) 2.74 (td, J=8.36, 8.36 Hz, 2 H) 4.48 (d, J=7.46 Hz, 2 H) 4.68–4.85 (m, 2 H) 5.97 (m, 1 H) 6.22 (m, 1 H) 7.18 (s, 1 H) 7.91 (s, 1 H) 8.09 (s, 1 H) 8.80 (s, 1 H) 10.34 (s, 1 H).

EXAMPLE 97

16-bromo-18-methyl-2-oxo-2,3,11,12,13,14-hexahydro-1H,10H-8,4-epiazeno-9,15,1,3,6-benzodioxatriazacycloheptadecine-7-carbonitrile To a solution of Example 96D (36.1 mg, 0.0839 mmol) in THF (5 mL) was added 10% Pd/C (7.2 mg). The reaction mixture was stirred under hydrogen (a balloon was used) for 2.5 hours. The reaction mixture was diluted with MeOH and the catalyst was filtered. The filtrate was concentrated and the residue was triturated with ether to give 23.1 mg (64%) of the desired product as gray solid. MS (ESI) m/z: 430.1 $(M-H)^+$; $^1H$ NMR (300 MHz, DMSO-D6) δ ppm 1.56–1.67 (m, 2 H) 1.85–1.98 (m, 4 H) 2.28 (s, 3 H) 4.04 (t, J=5.26 Hz, 2 H) 4.85 (t, J=6.95 Hz, 2 H) 7.20 (d, J=1.50 Hz, 1 H) 8.00 (s, 1 H) 8.03 (d, J=1.36 Hz, 1 H) 10.45 (s, 1 H) 10.96 (s, 1 H).

EXAMPLE 98

16-(3-hydroxyprop-1-ynyl)-18-methyl-2-oxo-2,3,11,12,13,14-hexahydro-1H,10H-8,4-epiazeno-9,15,1,3,6-benzodioxatriazacycloheptadecine-7-carbonitrile A mixture of Example 97 (20.0 mg, 0.0463 mmol), CuI (2.0 mg), Pd(dppf)$Cl_2$·$CH_2Cl_2$ (3.8 mg), triethylamine (39 μL, 0.278 mmol), and propargyl alcohol (16 μL, 0.278 mmol) in DMF (1 mL) was heating in a microwave apparatus (Explorer from CEM Corp.) at 150° C. for 65 minutes. The crude product was purified using reversed-phase preparative HPLC to give 2.0 mg of the desired product. MS (DCI/$NH_3$) m/z: 408.2 $(M+H)^+$; $^1H$ NMR (400 MHz, $CD_3OD$) δ ppm 1.67–1.76 (m, 2 H) 1.97–2.09 (m, 4 H) 2.27 (s, 3 H) 4.26 (t, J=4.80 Hz, 2 H) 4.44 (s, 2 H) 4.92 (t, J=6.90 Hz, 2 H) 6.96 (s, 1 H) 7.89 (s, 1 H) 8.05 (s, 1 H) 10.55 (s, 1 H).

EXAMPLE 99

18-chloro-2-oxo-2,3,11,14-tetrahydro-1H,10H-8,4-epiazenopyrido[2,3-b][1,12,4,6,9]dioxatriazacycloheptadecine-7-carbonitrile

EXAMPLE 99A 2-(allyloxy)-5-chloro-3-nitropyridine

To a mixture of 5-chloro-3-nitro-pyridin-2-ol (0.600 g, 3.4 mmol), DBAD (1.19 g, 5.16 mmol), triphenylphosphine-polymer supported (3 mmol/g, 1.70 g, 5.16 mmol) in THF (18 mL) was added allyl alcohol (0.42 mL, 6.12 mmol). The reaction mixture was stirred at room temperature overnight, filtered through celite, and concentrated. The residue was purified by flash chromatography eluting with hexane/ethyl acetate (95:5 to 1:1) to give 0.120 g (15%) of the desired product. MS (DCI/NH$^3$) m/z: 214.9 (M+H)$^+$; $^1$H NMR (300 MHz, CDCl$^3$) δ ppm 5.01 (ddd, J=5.34, 1.40, 1.40 Hz, 2 H) 5.32 (dd, J=10.51, 1.36 Hz, 1 H) 5.49 (dd, J=17.12, 1.53 Hz, 1 H) 6.06 (m, 1 H) 8.28 (d, J=2.37 Hz, 1 H) 8.34 (d, J=2.37 Hz, 1 H).

EXAMPLE 99B 2-(allyloxy)-5-chloropyridin-3-amine

A mixture of Example 99A (0.120 g, 0.559 mmol), Fe (0.313 g, 5.59 mmol), NH$^4$Cl (0.0150 g, 0.28 mmol), and H$^2$O (0.40 ml) in EtOH (1.4 mL) was heated at 90° C. for 5 hours. The reaction mixture was cooled and filtered through celite. The filtrate was concentrated, treated with ethyl acetate, and washed with water and brine. The organic layer was dried over MgSO$^4$ and concentrated. The crude product was purified by flash chromatography eluting with hexane/ethyl acetate (9:1) to give 23.3 mg (23%) of the desired product. LC/MS (APCI) m/z:185.2 (M+H)$^+$; $^1$H NMR (300 MHz, CDCl$^3$) δ ppm 2.97 (s, 2H, brd) 4.87 (d, J=5.43 Hz, 2 H) 5.26 (dd, J=10.51, 1.02 Hz, 1 H) 5.38 (dd, J=17.12, 1.53 Hz, 1 H) 6.09 (m, 1 H) 6.90 (d, J=2.37 Hz, 1 H) 7.49 (d, J=2.03 Hz, 1 H).

EXAMPLE 99C

N-[2-(allyloxy)-5-chloropyridin-3-yl]-N'-[6-(but-3-enyloxy)-5-cyanopyrazin-2-yl]urea Example 99B (23.3 mg, 0.128 mmol) and Example 7F (47.5 mg, 0.153 mmol) in DMF (2 mL) were heated at 85° C. for 5 hours. The reaction mixture was cooled, diluted with ethyl acetate, and washed with 50% brine and water. The organic layer was dried over MgSO$^4$ and concentrated. The crude product was purified by flash chromatography eluting with hexane/ethyl acetate/dichloromethane (8:2:1) to give 10.0 mg (20%) of the desired product. MS (ESI) m/z: 401.2 (M+H)$^+$; $^1$H NMR (400 MHz, CDCl$^3$) δ ppm 2.59 (td, J=6.44, 6.44 Hz, 2 H) 4.51 (t, J=6.44 Hz, 2 H) 4.95 (d, J=5.52 Hz, 2 H) 5.04–5.22 (m, 2 H) 5.24–5.42 (m, 2 H) 5.84 (m, 1 H) 6.05 (m, 1 H) 7.86 (s, 1 H) 8.12 (s, 1 H) 8.26 (s, 1 H) 8.50 (s, 1 H) 9.59 (s, 1 H).

EXAMPLE 99D 18-chloro-2-oxo-2,3,11,14-tetrahydro-1H,10H-8,4-epiazenopyrido[2,3-b][1,12,4,6,9]dioxatriazacycloheptadecine-7-carbonitrile Example 99C (9.0 mg, 0.022 mmol) in CH$^2$Cl$^2$ (8 mL) was treated with the second generation Grubbs Catalyst (2.1 mg, 0.0034 mmol). The reaction mixture was stirred at 40° C. overnight. Solvent was evaporated and the residue was purified by flash chromatography eluting with dichloromethane/methanol (9:1) to give 2.9 mg (36%) of the desired product. MS (ESI) m/z: 371.1 (M–H)$^+$; $^1$H NMR (400 MHz, CDCl$^3$) δ ppm 2.68–2.95 (m, 2 H) 4.73 (t, J=7.82 Hz, 2 H) 5.01 (d, J=7.06 Hz, 2 H) 5.98 (m, 1 H) 6.11 (m, 1 H) 7.84 (s, 1 H) 7.88 (s, 1 H) 8.30 (s, 1 H) 8.47 (s, 1 H) 10.37 (s, 1 H).

EXAMPLE 100

18-chloro-17-hydroxy-2-oxo-2,3,11,12,13,14-hexahydro-1H,10H-8,4-metheno-9,15,1,3-benzodioxadiazacycloheptadecine-7-carbonitrile

EXAMPLE 100A methyl 2-(but-3-enyloxy)-4-nitrobenzoate

2-Hydroxy-4-nitrobenzoic acid was converted to the methyl ester by heating a solution of the acid in methanol with a catalytic amount of conc. sulfuric acid. That ester (4.0 g, 20.3 mmol) was dissolved in THF (100 mL), then polymer-supported PPh$^3$ (20 g, 3 mmol/g PPh$^3$, 60.0 mmol), 3-buten-1-ol (2.2 mL, 1.8 g, 25.7 mmol), and di-tert-butylazodicarboxylate (5.4 g, 23.5 mmol) were added. After stirring at room temperature overnight more 3-buten-1-ol (0.8 mL, 0.7 g, 9.7 mmol) and di-tert-butylazodicarboxylate (2.0 g, 8.7 mmol) were added and the reaction was stirred another day at room temperature. The reaction was then filtered through celite, the cake washed with EtOAc, and the filtrate concentrated. The crude was purified by column chromatography using 9/1 hexanes/EtOAc. The product was recovered (4.2 g, 84%) as very pale yellow solids. MS (DCI/NH$^3$) m/z: 252 (M+H)$^+$; $^1$H NMR (300 MHz, DMSO-d$^6$) δ ppm 2.46–2.55 (m, 2H), 3.83 (s, 3H), 4.24 (t, J=6.4 Hz, 2H), 5.09 (m, 1H), 5.18 (m, 1H), 5.90 (m, 1H), 7.83–7.87 (m, 2H), 7.88 (s, 1H).

EXAMPLE 100B 2-(but-3-enyloxy)-4-nitrobenzamide

The compound described in Example 100A was saponified by stirring it in methanol and 4N NaOH at room temperature overnight. That acid (4.0 g, 16.7 mmol) was dissolved in DMF (35 mL), then HOBT (2.5 g, 18.5 mmol) and EDCI-HCl (3.5 g, 18.3 mmol) were added and that stirred at room temperature for 75 min. Then conc. NH$^4$OH (6.0 mL) was added and the reaction stirred at room temperature for 4 days. Water (450 mL) was added, the resultant solids filtered off and dried to give the product (3.6 g, 90%) as white solids. MS (DCI/NH$^3$) m/z: 237 (M+H)$^+$; $^1$H NMR (300 MHz, DMSO-d$^6$) δ ppm 2.53–2.62 (m, 2H), 4.31 (t, J=6.1 Hz, 2H), 5.11 (m, 1H), 5.20 (m, 1H), 5.92 (m, 1H), 7.66 (br s, 1H), 7.85 (br s, 1H), 7.84–7.89 (m, 2H), 7.93 (m, 1H).

EXAMPLE 100C 2-(but-3-enyloxy)-4-nitrobenzonitrile

The compound described in Example 100B (3.6 g, 15.1 mmol) was slurried in THF (30 mL), cooled in an ice-water bath, then triethylamine (6.3 mL, 4.6 g, 45.3 mmol) was added and the reaction stirred for 10 min. Then trifluoroacetic acid anhydride (3.2 mL, 4.8 g, 22.6 mmol) was added dropwise over 10 min. The reaction was stirred cold under N$^2$ for 50 min., then the bath was removed and stirring continued for another 70 min. The reaction was then poured onto ice, then Et$^2$O and water were added. The organic layer was washed with 2M Na$^2$CO$^3$ and brine. After drying the organic layer over Na$^2$SO$^4$, filtration and concentration the product (3.5 g, 100%) was recovered as yellow-tan solids. MS (DCI/NH$^3$) m/z: 236 (M+H+ NH$^3$)$^+$; $^1$H NMR (300 MHz, DMSO-d$^6$) δ ppm 2.53–2.59 (m, 2H), 4.37 (t, J=6.4

Hz, 2H), 5.12 (m, 1H), 5.21 (m, 1H), 5.90 (m, 1H), 7.90 (dd, J=8.5 and 2.0 Hz, 1H), 7.99 (d, J=2.0 Hz, 1H), 8.07 (d, J=8.5 Hz, 1H).

EXAMPLE 100D 4-amino-2-(but-3-enyloxy)benzonitrile

The compound described in Example 100C (1.5 g, 6.9 mmol) was dissolved in THF (35 mL), then a solution of $NH^4Cl$ (0.41 g, 7.7 mmol) in water (17 mL) was added, followed by the addition of iron powder (1.9 g, 34.0 mmol). The reaction was heated at 85° C. for 2.5 h. More $NH^4Cl$ (0.57 g, 10.6 mmol) and iron powder (1.5 g, 26.9 mmol) were added and the heating continued for another 2.5 h. The reaction was then cooled to room temperature, filtered through celite, and concentrated. The residue was partitioned between EtOAc and 2M $Na^2CO^3$, then the organic layer was washed with brine and dried over $Na^2SO^4$. After filtration and concentration the product (1.3 g, 100%) was recovered as an orange syrup. MS (DCI/$NH^3$) m/z: 206 (M+H+ $NH^3$)+; $^1H$ NMR (300 MHz, DMSO-$d^6$) δ ppm 2.44–2.53 (m, 2H), 4.02 (t, J=6.8 Hz, 2H), 5.10 (m, 1H), 5.18 (m, 1H), 5.93 (m, 1H), 6.18 (dd, J=8.5 and 2.0 Hz, 1H), 6.24 (d, J=2.0 Hz, 1H), 7.22 (d, J=8.5 Hz, 1H).

EXAMPLE 100E phenyl 3-(but-3-enyloxy)-4-cyanophenylcarbamate

The compound described in Example 100D (1.3 g, 6.9 mmol) was dissolved in $CH^3CN$ (20 mL), cooled to 0° C., then diisopropylethylamine (1.3 mL, 0.96 g, 7.5 mmol) was added followed by the dropwise addition of phenyl chloroformate (1.0 mL, 1.2 g, 7.7 mmol). The reaction was stirred cold for 1 h., by which time thin-layer chromatography (7/3 hexanes/EtOAc) showed that all the starting material had been converted to an upper spot. The reaction was then poured onto ice, then $Et^2O$ and 2M $Na^2CO^3$ were added. The organic layer was washed with brine and dried over $Na^2SO^4$. After filtration and concentration the product (2.2 g, 100%) was recovered as orange solids and carried on to the next step with no purification. MS (DCI/$NH^3$) m/z: 326 (M+H+ $NH^3$)+.

EXAMPLE 100F

N-(2-(allyloxy)-5-chloro-4-{[2-(trimethylsilyl) ethoxy]methoxy}phenyl)-N'-[3-(but-3-enyloxy)-4-cyanophenyl]urea The compound described in Example 100E (322 mg, 1.04 mmol) and the compound described in Example 10D(295 mg, 0.90 mmol) were dissolved in DMF (1.0 mL) and heated at 50° C. overnight. Next day, the temperature was raised to 100° C. and the reaction stirred at that temperature for 90 min. The reaction was then cooled to room temperature and partitioned between water and EtOAc. The organic layer was washed with brine and dried over $Na^2SO^4$. The crude material was purified by column chromatography using 65/35 hexanes/EtOAc, giving the product (260 mg, 53%). MS (ESI) m/z: 544 and 546 (M+H)+; $^1H$ NMR (300 MHz, DMSO-$d^6$) δ ppm –0.01 (s, 9H), 0.91 (t, J=8.1 Hz, 2H), 2.51–2.59 (m, 2H), 3.78 (t, J=8.1 Hz, 2H), 4.16 (t, J=6.5 Hz, 2H), 4.69–4.73 (m, 2H), 5.13 (m, 1H), 5.21 (m, 1H), 5.29 (s, 2H), 5.34 (m, 1H), 5.47 (m, 1H), 5.92 (m, 1H), 6.10 (m, 1H), 6.99 (dd, J=8.5 and 2.0 Hz, 1H), 7.01 (s, 1H), 7.51 (d, J=2.0 Hz, 1H), 7.60 (d, J=8.5 Hz, 1H), 8.14 (s, 1H), 8.28 (s, 1H), 9.81 (s, 1H).

EXAMPLE 100G 18-chloro-17-hydroxy-2-oxo-2,3,11,12,13,14-hexahydro-1H,10H-8,4-metheno-9,15,1,3-benzo-dioxadiazacycloheptadecine-7-carbonitrile The title compound was prepared from the compound described in Example 100F by the following sequence. 1) Cyclization as described in Example 1, but substituting Hoyveda-Grubbs catalyst for Grubbs second generation catalyst and running the reaction in 1,2-dichloroethane at 85° C. for 2 h. instead of dichloromethane at 50° C. overnight. 2) Reduction as described in Example 2 but substituting palladium-on-carbon for platinum-on-carbon and running the reaction in THF instead of THF-MeOH. 3) A deprotection of the phenol by stirring in MeOH-dioxane with a catalytic amount of conc. HCl at room temperature for 90 min., followed by purification using preperative HPLC. MS (DCI/$NH^3$) m/z: 405 and 407 (M+H+ $NH^3$)+; $^1H$ NMR (400 MHz, DMSO-$d^6$) δ ppm 1.52–1.59 (m, 2H), 1.75–1.81 (m, 2H), 1.81–1.89 (m, 2H), 4.01–4.07 (m, 2H), 4.30–4.35 (m, 2H), 6.63 (s, 1H), 6.65 (d, J=8.6 Hz, 1H), 7.28 (s, 1H), 7.60 (d, J=8.6 Hz, 1H), 7.78 (s, 1H), 8.07 (s, 1H), 9.25 (s, 1H), 9.90 (s, 1H).

EXAMPLE 101

11,12-cis-dihydroxy-18-nitro-2-oxo-2,3,11,12,13,14-hexahydro-1H,10H-8,4-epiazeno-9,15,1,3,6-benzo-dioxatriazacycloheptadecine-7-carbonitrile Example 83E (15 mg, 0.04 mmol) was oxidized using a similar procedure described in Example 55D to give the title compound (3.9 mg, 24%). MS (ESI) m/z 415.12 (M–H)−; $^1H$ NMR (500 MHz, DMSO-$D^6$) δ ppm 1.93 (m, 1 H) 2.17 (m, 1 H) 3.84 (m, 1 H) 4.21 (m, 1 H) 4.37 (t, J=9.61 Hz, 1 H) 4.52–4.64 (m, 2 H) 4.77 (dd, J=11.44, 2.90 Hz, 1 H) 4.97 (d, J=4.88 Hz, 1 H) 5.17 (d, J=5.19 Hz, 1 H) 7.42 (d, J=9.15 Hz, 1 H) 8.02–8.12 (m, 2 H) 9.10 (d, J=2.75 Hz, 1 H) 10.18 (s, 1 H) 11.09 (s, 1 H).

EXAMPLE 102

11,12-trans-dihydroxy-18-nitro-2-oxo-2,3,11,12,13,14-hexahydro-1H,10H-8,4-epiazeno-9,15,1,3,6-benzodioxatriazacycloheptadecine-7-carbonitrile

EXAMPLE 102A (trans) 18-nitro-2-oxo-2,3,13,14-tetrahydro-1H,10H-8,4-epiazeno-9,15,1,3,6-benzodioxatriazacyclohepta-decine-7-carbonitrile The desired product (13.5 mg, 8%) was prepared using the same procedure in Example 83. MS (ESI) m/z 381.19 (M–H)−; $^1H$ NMR (500 MHz, DMSO-$D^6$) δ ppm 2.39–2.47 (m, 2 H) 4.41 (t, J=5.63 Hz, 2 H) 4.89–4.94 (m, 2 H) 5.66 (m, 1 H) 5.74 (m, 1 H) 7.37 (d, J=9.14 Hz, 1 H) 8.02 (s, 1 H) 8.07 (dd, J=9.14, 2.74 Hz, 1 H) 8.70 (d, J=2.74 Hz, 1 H) 9.31 (s, 1 H) 10.97 (s, 1 H).

EXAMPLE 102B 11,12-trans-dihydroxy-18-nitro-2-oxo-2,3,11,12,13,14-hexahydro-1H,10H-8,4-epiazeno-9,15,1,3,6-benzodioxatriazacycloheptadecine-7-carbonitrile Example 102A (12.3 mg, 0.032 mmol) was oxidized using a similar procedure described in Example 55D to give the title compound (2.3 mg, 17%). MS (ESI) m/z 415.04 (M−H)⁻; $^1$H NMR (500 MHz, DMSO-D$^6$) δ ppm 2.01 (q, J=4.78 Hz, 2 H) 3.58 (m, 1 H) 4.04 (m, 1 H) 4.42 (t, J=5.19 Hz, 2 H) 4.52 (m, 1 H) 4.76 (dd, J=11.44, 2.29 Hz, 1 H) 5.08 (d, J=4.58 Hz, 1 H) 5.16 (d, J=5.19 Hz, 1 H) 7.42 (d, J=9.46 Hz, 1 H) 7.97–8.08 (m, 2 H) 9.12 (d, J=3.05 Hz, 1 H) 10.12 (s, 1 H) 11.05 (s, 1 H).

EXAMPLE 103

18-ethoxy-12,13-dihydroxy-2-oxo-2,3,11,12,13,14-hexahydro-1H,10H-8,4-epiazeno-9,15,1,3,6-benzodioxatriazacycloheptadecine-7-carbonitrile Example 84C (58.2 mg, 0.15 mmol) was oxidized using a similar procedure described in Example 55D to give the title compound (10.1 mg, 16%). MS (ESI) m/z 414.21 (M−H)⁻; $^1$H NMR (500 MHz, DMSO-D$^6$) δ ppm 1.37 (t, J=7.02 Hz, 3 H) 1.98 (m, 1 H) 2.41 (m, 1 H) 3.81–3.91 (m, 2 H) 4.02 (q, J=6.81 Hz, 2 H) 4.07–4.17 (m, 2 H) 4.67 (m, 1 H) 4.76 (m, 1 H) 4.95 (d, J=4.88 Hz, 1 H) 5.12 (d, J=5.19 Hz, 1 H) 6.72 (dd, J=9.00, 2.90 Hz, 1 H) 7.10 (d, J=9.15 Hz, 1 H) 7.81 (d, J=3.05 Hz, 1 H) 8.05 (s, 1 H) 9.81 (s, 1 H) 10.91 (s, 1 H)

EXAMPLE 104

18-methoxy-2-oxo-2,3,11,14-tetrahydro-1H,10H-8,4-epiazeno-9,15,1,3,6-benzodioxatriazacycloheptadecine-7-carbonitrile

EXAMPLE 104A

2-[2-(allyloxy)-5-methoxyphenyl]-1H-isoindole-1,3(2 H)-dione

A mixture of Example 84A (0.69 g, 2.34 mmol), iodomethane (0.58 mL, 9.34 mmol) and K$^2$CO$^3$ (1.61 g, 11.68 mmol) in acetone (20 mL) was stirred, and refluxed for 3 hours, cooled. The solution was filtered, dried with silica gel powder (10 g). 30% Ethyl acetate in hexanes (2 L) was used to run flash chromatography. The title compound was obtained (377 mg, 52%). MS (APCI) m/z 310 (M+H)⁺.

EXAMPLE 104B 2-(allyloxy)-5-methoxyaniline

Example 104A (377 mg, 1.21 mmol) was dissolved in methanol (50 mL). H$^2$NNH$^2$ (0.114 mL, 3.65 mmol) was added. The reaction was run at room temperature for 3 hours. The solvents were removed via a vacuum pump. The residue was dissolved in acetone (20 mL). The solution was dried with silica gel powder (10 g). 15% Ethyl acetate in hexanes (2 L) was used to run flash chromatography to give the title compound (210.6 mg, 97%). MS (DCI) m/z 180.03 (M+H)⁺; $^1$H NMR (300 MHz, CDCl$^3$) δ ppm 3.74 (s, 3 H) 4.53 (t, J=1.36 Hz, 1 H) 4.55 (t, J=1.53 Hz, 1 H) 5.24 (m, 1 H) 5.41 (m, 1 H) 6.08 (m, 1 H) 6.43 (dd, J=8.82, 2.71 Hz, 1 H) 6.68 (d, J=3.05 Hz, 1 H) 6.78 (d, J=8.82 Hz, 1 H)

EXAMPLE 104C

N-[2-(allyloxy)-5-methoxyphenyl]-N'-[6-(but-3-enyloxy)-5-cyanopyrazin-2-yl]urea

Example 104B (210.5 mg, 1.17 mmol) and Example 7F (364.1 mg, 1.17 mmol) were coupled using a similar procedure described in Example 60C to give the title compound (430.8 mg, 92%). MS (ESI) m/z 394.12 (M−H)⁻; $^1$H NMR (500 MHz, DMSO-D$^6$) δ ppm 2.54 (q, J=6.71 Hz, 2 H) 3.70 (s, 3 H) 4.46 (t, J=6.56 Hz, 2 H) 4.62 (d, J=5.49 Hz, 2 H) 5.12 (d, J=10.37 Hz, 1 H) 5.18 (dd, J=17.24, 1.68 Hz, 1 H) 5.28 (dd, J=10.68, 1.22 Hz, 1 H) 5.41 (dd, J=17.39, 1.53 Hz, 1 H) 5.88 (m, 1 H) 6.08 (m, 1 H) 6.58 (dd, J=9.15, 3.05 Hz, 1 H) 6.98 (d, J=9.15 Hz, 1 H) 7.79 (d, J=3.05 Hz, 1 H) 8.88 (s, 1 H) 8.99 (s, 1 H) 10.69 (s, 1 H)

EXAMPLE 104D 18-methoxy-2-oxo-2,3,11,14-tetrahydro-1H,10H-8,4-epiazeno-9,15,1,3,6-benzodioxatriazacycloheptadecine-7-carbonitrile Example 104C (430.8 mg, 1.09 mmol) was cyclized using a similar procedure described in Example 55C to give the title compound (148.7 mg, 37%). MS (ESI) m/z 366.16 (M−H)⁻; $^1$H NMR (500 MHz, DMSO-D$^6$) δ ppm 2.69 (q, J=7.53 Hz, 2 H) 3.71 (s, 3 H) 4.61 (d, J=7.32 Hz, 2 H) 4.68 (t, J=7.48 Hz, 2 H) 5.98 (m, 1 H) 6.08 (m, 1 H) 6.63 (dd, J=8.85, 3.05 Hz, 1 H) 7.09 (d, J=9.15 Hz, 1 H) 7.72 (d, J=3.05 Hz, 1 H) 7.98 (s, 1 H) 10.27 (s, 1 H) 10.87 (s, 1 H)

EXAMPLE 105

2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile

EXAMPLE 105A

2-{2-(allyloxy)-5-[2-(tetrahydro-2H-pyran-2-yloxy)ethoxy]phenyl}-1H-isoindole-1,3(2 H)-dione A mixture of Example 84A (0.69 g, 2.34 mmol), 2-(2-bromoethoxy)tetrahydro-2H-pyran (1.41 mL, 9.34 mmol) and K$^2$CO$^3$ (1.61 g, 11.68 mmol) in acetone (20 mL) was refluxed overnight and cooled. The solution was filtered, dried with silica gel powder (10 g). 20% Ethyl acetate in hexanes (1 L) and 30% ethyl acetate in hexanes (1 L) were used to run flash chromatography. The title compound was obtained (265.3 mg, 27%). MS (APCI) m/z 424 (M+H)⁺.

EXAMPLE 105B 2-(allyloxy)-5-[2-(tetrahydro-2H-pyran-2-yloxy)ethoxy]aniline

Example 105A (265.3 mg, 0.63 mmol) was dissolved in methanol (50 mL). H$^2$NNH$^2$ (0.12 mL, 3.60 mmol) was added. The reaction was stirred at room temperature for 3 hours. Then the solvents were removed via a vacuum pump. The residue was dissolved in acetone (20 mL). The solution was dried with silica gel powder (10 g). 20% Ethyl acetate in hexanes (2 L) was used to run flash chromatography to give the title compound (189.5 mg, 100%). MS (DCI) m/z 294.13 (M+H)⁺; $^1$H NMR (300 MHz, CDCl$^3$) δ ppm 1.55–1.94 (m, 6 H) 3.73–3.82 (m, 2 H) 3.98 (t, J=4.75 Hz, 1 H) 4.04–4.11 (m, 3 H) 4.53 (d, J=5.43 Hz, 2 H) 4.70 (t, J=3.56 Hz, 1 H) 5.25 (m, 1 H) 5.40 (m, 1 H) 6.07 (m, 1 H) 6.40 (dd, J=8.82, 2.71 Hz, 1 H) 6.61 (d, J=2.71 Hz, 1 H) 6.75 (d, J=8.82 Hz, 1 H).

EXAMPLE 105C

N-{2-(allyloxy)-5-[2-(tetrahydro-2H-pyran-2-yloxy) ethoxy]phenyl}-N'-[6-(but-3-enyloxy)-5-cyanopyrazin-2-yl]urea Example 105B (187.6 mg, 0.64 mmol) and Example 7F (198.2 mg, 0.64 mmol) were coupled using a similar procedure described in Example 60C to give the title compound (263.9 mg, 81%). MS (ESI) m/z 508.36 (M–H)$^-$; $^1$H NMR (500 MHz, DMSO-D$^6$) δ ppm 1.41–1.55 (m, 4 H) 1.63 (m, 1 H) 1.75 (m, 1 H) 2.54 (q, J=6.51 Hz, 2 H) 3.45 (m, 1 H) 3.69 (m, 1 H) 3.79 (m, 1 H) 3.90 (m, 1 H) 3.97 (t, J=6.71 Hz, 1 H) 4.05 (t, J=4.58 Hz, 2 H) 4.46 (t, J=6.71 Hz, 2 H) 4.62 (d, J=5.49 Hz, 1 H) 4.65 (t, J=3.51 Hz, 1 H) 5.12 (d, J=10.37 Hz, 1 H) 5.18 (dd, J=17.09, 1.83 Hz, 1 H) 5.28 (dd, J=10.53, 1.37 Hz, 1 H) 5.41 (dd, J=17.24, 1.68 Hz, 1 H) 5.88 (m, 1 H) 6.08 (m, 1 H) 6.60 (dd, J=8.85, 3.05 Hz, 1 H) 6.97 (d, J=8.85 Hz, 1 H) 7.81 (d, J=3.05 Hz, 1 H) 8.87 (s, 1 H) 8.99 (s, 1 H) 10.70 (s, 1 H).

EXAMPLE 105D 2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile Example 105C (263.9 mg, 0.52 mmol) was cyclized using a similar procedure described in Example 55C to give the title compound (116.3 mg, 47%). MS (ESI) m/z 480.26 (M–H)$^-$; $^1$H NMR (500 MHz, DMSO-D$^6$) δ ppm 1.40–1.54 (m, 4 H) 1.64 (m, 1 H) 1.72 (m, 1 H) 2.70 (q, J=7.53 Hz, 2 H) 3.45 (m, 1 H) 3.70 (m, 1 H) 3.78 (m, 1 H) 3.90 (m, 1 H) 4.06 (t, J=4.73 Hz, 2 H) 4.62 (d, J=7.02 Hz, 2 H) 4.65 (t, J=3.51 Hz, 1 H) 4.69 (t, J=7.48 Hz, 2 H) 5.98 (m, 1 H) 6.08 (m, 1 H) 6.66 (dd, J=8.85, 3.05 Hz, 1 H) 7.09 (d, J=9.15 Hz, 1 H) 7.74 (d, J=2.75 Hz, 1 H) 7.98 (s, 1 H) 10.27 (s, 1 H) 10.88 (s, 1 H)

EXAMPLE 106

12,13-dihydroxy-18-methoxy-2-oxo-2,3,11,12,13,14-hexahydro-1H,10H-8,4-epiazeno-9,15,1,3,6-benzodioxatriazacycloheptadecine-7-carbonitrile Example 104D (55.2 mg, 0.15 mmol) was oxidized using a similar procedure described in Example 55D to give the title compound (20.8 mg, 34%). MS (ESI) m/z 400.11 (M–H)$^-$; $^1$H NMR (500 MHz, DMSO-D$^6$) δ ppm 1.91 (m, 1 H) 2.33 (m, 1 H) 3.71 (s, 3 H) 3.75–3.85 (m, 2 H) 3.99–4.12 (m, 2 H) 4.61 (m, 1 H) 4.69 (m, 1 H) 4.88 (d, J=4.88 Hz, 1 H) 5.05 (d, J=5.19 Hz, 1 H) 6.67 (dd, J=9.15, 3.05 Hz, 1 H) 7.06 (d, J=9.15 Hz, 1 H) 7.76 (d, J=3.05 Hz, 1 H) 7.99 (s, 1 H) 9.75 (s, 1 H) 10.85 (s, 1 H)

EXAMPLE 107

18-(2-hydroxyethoxy)-2-oxo-2,3,11,14-tetrahydro-1H,10H-8,4-epiazeno-9,15,1,3,6-benzodioxatriazacycloheptadecine-7-carbonitrile Example 105D (100 mg, 0.21 mmol) was treated with a mixture of acetic acid, THF and water using a similar procedure described in Example 61 to give the title compound (60.5 mg, 73%). MS (ESI) m/z 396.01 (M–H)$^-$; $^1$H NMR (500 MHz, DMSO-D$^6$) δ ppm 2.70 (q, J=7.43 Hz, 2 H) 3.69 (q, J=5.49 Hz, 2 H) 3.91 (t, J=5.03 Hz, 2 H) 4.61 (d, J=7.32 Hz, 2 H) 4.69 (t, J=7.48 Hz, 2 H) 4.83 (t, J=5.65 Hz, 1 H) 5.98 (m, 1 H) 6.08 (m, 1 H) 6.64 (dd, J=8.85, 3.05 Hz, 1 H) 7.08 (d, J=9.15 Hz, 1 H) 7.75 (d, J=3.05 Hz, 1 H) 7.97 (s, 1 H) 10.27 (s, 1 H) 10.89 (s, 1 H)

EXAMPLE 108

18-[2-(dimethylamino)ethoxy]-2-oxo-2,3,11,14-tetrahydro-1H,10H-8,4-epiazeno-9,15,1,3,6-benzodioxatriazacycloheptadecine-7-carbonitrile To a solution of Example 73H (149.7 mg, 0.42 mmol) in anhydrous tetrahydrofuran (5 mL) was added polymer supported triphenylphosphine (282 mg, 0.85 mmol), di-tert-butyl azodicarboxylate (195 mg, 0.85 mmol), and N,N-dimethylaminoethanol (38.9 mg, 0.44 mmol). The reaction mixture was shaken at room temperature for overnight. The solution was filtered, concentrated, dissolved in DMSO/methanol (1/1, 3 mL), and separated by HPLC to give the title compound (4.3 mg, 2%). MS (ESI) m/z 423.25 (M–H)$^-$; $^1$H NMR (400 MHz, DMSO-D$^6$) δ ppm 2.59–2.67 (m, 2 H) 2.85 (s, 6 H) 3.35–3.41 (m, 2 H) 4.35 (t, J=6.75 Hz, 2 H) 4.50 (d, J=6.75 Hz, 2 H) 4.55–4.67 (m, 2 H) 5.86–6.08 (m, 2 H) 6.42 (dd, J=8.75, 2.92 Hz, 1 H) 6.90 (d, J=8.90 Hz, 1 H) 7.59 (d, J=3.07 Hz, 1 H) 8.34 (s, 1 H) 8.98 (s, 1 H) 9.31 (s, 1 H) 10.31 (s, 1 H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

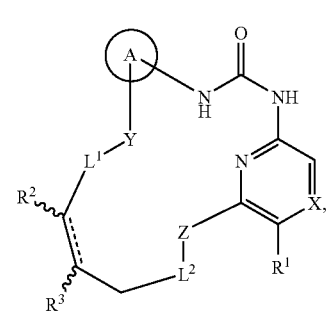

or a therapeutically acceptable salt thereof, wherein

- - - - - is a single or double bond;

A is aryl, wherein the aryl is optionally substituted with one, two, or three substituents independently selected from the group consisting of alkoxy, alkoxyalkoxy, alkoxyalkoxyalkoxy, alkyl, cyano, halo, haloalkylsulfonyloxy, haloalkoxy, heteroarylalkoxy, heterocycle, heterocyclealkoxy, heterocycleoxyalkoxy, heterocycleoxyalkyl, heterocycleoxyalkynyl, heteroarylcarbonylalkoxy, haloalkyl, hydroxyalkenyl, hydroxyalkoxy, hydroxyalkyl, hydroxyalkynyl, hydroxy, nitro, $NR^aR^b$, $(NR^aR^b)$alkoxy, $(NR^aR^b)$alkyl, and $(NR^aR^b)$alkynyl;

$R^1$ is selected from the group consisting of hydrogen, alkoxycarbonyl, alkyl, carboxy, cyano, halo, and nitro;

$R^2$ and $R^3$ are independently selected from the group consisting of hydrogen, alkoxy, alkoxycarbonyl, alkyl, alkylsulfonyl, arylsulfonyl, halo, hydroxy, and $NR^aR^b$;

or $R^2$ and $R^3$, together with the atoms to which they are attached, form an epoxide;

X is N;

Y is selected from the group consisting of $CH_2$, O, and $NR^z$, wherein $R^z$ is selected from the group consisting of hydrogen and alkyl;

Z is O;

$L^1$ and $L^2$ are independently selected from the group consisting of a bond and alkylene;

$R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl, and $(NR^cR^d)$alkylcarbonyl; and $R^c$ and $R^d$ are independently selected from the group consisting of hydrogen, alkyl, and cycloalkyl.

2. A compound of formula (II)

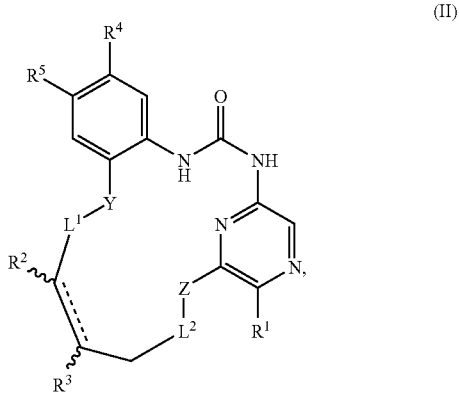

(II)

or a therapeutically acceptable salt thereof, wherein

----- is a single or double bond;

$R^1$ is selected from the group consisting of hydrogen, alkoxycarbonyl, alkyl, carboxy, cyano, halo, and nitro;

$R^2$ and $R^3$ are independently selected from the group consisting of hydrogen, alkoxy, alkoxycarbonyl, alkyl, alkylsulfonyl, arylsulfonyl, halo, hydroxy, and $NR^aR^b$;

or $R^2$ and $R^3$, together with the atoms to which they are attached, form an epoxide;

$R^4$ is selected from the group consisting of alkoxy, alkyl, cyano, halo, heterocycleoxyalkoxy, heterocycleoxyalkyl, hydroxy, hydroxyalkoxy, hydroxyalkyl, nitro, $NR^aR^b$, and $(NR^aR^b)$alkoxy;

$R^5$ is selected from the group consisting of hydrogen, alkenyl, alkoxy, alkoxyalkoxy, alkoxyalkoxyalkoxy, alkoxyalkyl, alkoxycarbonyl, alkoxycarbonylalkyl, alkylsulfanyl, arylsulfanyl, alkylsulfonyl, arylsulfonyl, carboxy, carboxyalkyl, haloalkylsulfonyloxy, heteroarylalkoxy, heteroarylcarbonylalkoxy, heterocycle, heterocyclealkoxy, heterocycleoxyalkyl, heterocycleoxyalkynyl, hydroxy, hydroxyalkoxy, hydroxyalkyl, hydroxyalkynyl, $NR^aR^b$, $(NR^aR^b)$alkoxy, $(NR^aR^b)$alkyl, $(NR^aR^b)$alkynyl, $(NR^aR^b)$carbonyl, $(NR^aR^b)$carbonylalkoxy, and $(NR^aR^b)$carbonylalkyl;

Y is selected from the group consisting of $CH_2$, O, and $NR^z$, wherein $R^z$ is selected from the group consisting of hydrogen and alkyl;

Z is O;

$L^1$ and $L^2$ are independently selected from the group consisting of a bond and alkylene;

$R^a$ and $R^b$ are independently selected from the group consisting of hydrogen, alkoxycarbonyl, alkyl, alkylcarbonyl, alkylsulfonyl, aryl, arylalkyl, arylsulfonyl, haloalkylcarbonyl, haloalkylsulfonyl, heteroaryl, heteroarylalkyl, heteroarylcarbonyl, heteroarylsulfonyl, and $(NR^cR^d)$alkylcarbonyl; and $R^c$ and $R^d$ are independently selected from the group consisting of hydrogen, alkyl, and cycloalkyl.

3. The compound of claim 2 wherein $R^1$ is selected from the group consisting of hydrogen and cyano;

$R^2$ and $R^3$ are independently selected from the group consisting of hydrogen, alkoxy, and hydroxy;

$R^4$ is halo;

$R^5$ is $NR^aR^b$;

$R^a$ is hydrogen;

$R^b$ is heteroarylalkyl herein the heteroaryl portion of heteroalalkyl is pyridinyl;

is a single bond;

Y is O;

$L^1$ is $CH_2$; and $L^2$ is $CH_2$.

4. The compound of claim 1 wherein $L^1$ is $CH_2$ and $L^2$ is $CH_2$.

5. The compound of claim 1 selected from the group consisting of 18-chloro-11,14-dihydro-1H,10H-8,4-epiazeno-9,15,1,3,6-benzodioxatriazacycloheptadecin-2-one;

18-chloro-11,12,13,14-tetrahydro-1H,10H-8,4-epiazeno-9,15,1,3,6-benzodioxatriazacycloheptadecin-2-one;

18-chloro-12,13-dihydroxy-11,12,13,14-tetrahydro-1H,10H-8,4-epiazeno-9,15,1,3,6-benzodioxatriazacycloheptadecin-2-one;

17-chloro-10,13-dihydro-1H-8,4-epiazeno-9,14,1,3,6-benzodioxatriazacyclohexadecin-2-one;

17-chloro-10,11,12,13-tetrahydro-1H-8,4-epiazeno-9,14,1,3,6-benzodioxatriazacyclohexadecin-2-one;

17-chloro-11,12-dihydroxy-10,11,12,13-tetrahydro-1H-8,4-epiazeno-9,14,1,3,6-benzodioxatriazacyclohexadecin-2-one;

18-chloro-2-oxo-2,3,11,14-tetrahydro-1H,10H-8,4-epiazeno-9,15,1,3,6-benzodioxatriazacycloheptadecine-7-carbonitrile;

18-chloro-2-oxo-2,3,11,12,13,14-hexahydro-1H,10H-8,4-epiazeno-9,15,1,3,6-benzodioxatriazacycloheptadecine-7-carbonitrile;

18-chloro-12,13-dihydroxy-2-oxo-2,3,11,12,13,14-hexahydro-1H,10H-8,4-epiazeno-9,15,1,3,6-benzodioxatriazacycloheptadecine-7-carbonitrile;

18-chloro-17-hydroxy-2-oxo-2,3,11,12,13,14-hexahydro-1H,10H-8,4-epiazeno-9,15,1,3,6-benzodioxatriazacycloheptadecine-7-carbonitrile;

18-chloro-17-(3-hydroxypropoxy)-2-oxo-2,3,11,12,13,14-hexahydro-1H,10H-8,4-epiazeno-9,15,1,3,6-benzodioxatriazacycloheptadecine-7-carbonitrile;

18-chloro-17-(2,3-dihydroxypropoxy)-2-oxo-2,3,11,12,13,14-hexahydro-1H,10H-8,4-epiazeno-9,15,1,3,6-benzodioxatriazacycloheptadecine-7-carbonitrile;

18-chloro-17-(2-hydroxyethoxy)-2-oxo-2,3,11,12,13,14-hexahydro-1H,10H-8,4-epiazeno-9,15,1,3,6-benzodioxatriazacycloheptadecine-7-carbonitrile;

18-chloro-17-(2-methoxyethoxy)-2-oxo-2,3,11,12,13,14-hexahydro-1H,10H-8,4-epiazeno-9,15,1,3,6-benzodioxatriazacycloheptadecine-7-carbonitrile;

18-chloro-17-[2-(2-methoxyethoxy)ethoxy]-2-oxo-2,3,11,12,13,14-hexahydro-1H,10H-8,4-epiazeno-9,15,1,3,6-benzodioxatriazacycloheptadecine-7-carbonitrile;

18-chloro-17-[2-(dimethylamino)ethoxy]-2-oxo-2,3,11,12,13,14-hexahydro-1H,10H-8,4-epiazeno-9,15,1,3,6-benzodioxatriazacycloheptadecine-7-carbonitrile;

18-chloro-2-oxo-17-(2-piperidin-1-ylethoxy)-2,3,11,12,13,14-hexahydro-1H,10H-8,4-epiazeno-9,15,1,3,6-benzodioxatriazacycloheptadecine-7-carbonitrile;

18-chloro-2-oxo-17-(2-pyrrolidin-1-ylethoxy)-2,3,11,12,13,14-hexahydro-1H,10H-8,4-epiazeno-9,15,1,3,6-benzodioxatriazacycloheptadecine-7-carbonitrile;

18-chloro-17-(2-morpholin-4-ylethoxy)-2-oxo-2,3,11,12,13,14-hexahydro-1H,10H-8,4-epiazeno-9,15,1,3,6-benzodioxatriazacycloheptadecine-7-carbonitrile;

18-chloro-17-(3-morpholin-4-ylpropoxy)-2-oxo-2,3,11,12,13,14-hexahydro-1H,10H-8,4-epiazeno-9,15,1,3,6-benzodioxatriazacycloheptadecine-7-carbonitrile;

18-chloro-2-oxo-17-(pyridin-4-ylmethoxy)-2,3,11,12,13,14-hexahydro-1H,10H-8,4-epiazeno-9,15,1,3,6-benzodioxatriazacycloheptadecine-7-carbonitrile;

18-chloro-2-oxo-17-(pyridin-3-ylmethoxy)-2,3,11,12,13,14-hexahydro-1H,10H-8,4-epiazeno-9,15,1,3,6-benzodioxatriazacycloheptadecine-7-carbonitrile;

18-chloro-2-oxo-17-(pyridin-2-ylmethoxy)-2,3,11,12,13,14-hexahydro-1H,10H-8,4-epiazeno-9,15,1,3,6-benzodioxatriazacycloheptadecine-7-carbonitrile;

18-chloro-2-oxo-17-(2-oxo-2-pyridin-2-ylethoxy)-2,3,11,12,13,14-hexahydro-1H,10H-8,4-epiazeno-9,15,1,3,6-benzodioxatriazacycloheptadecine-7-carbonitrile;

18-chloro-17-[2-(1H-imidazol-1-yl)ethoxy]-2-oxo-2,3,11,12,13,14-hexahydro-1H,10H-8,4-epiazeno-9,15,1,3,6-benzodioxatriazacycloheptadecine-7-carbonitrile;

18-chloro-17-isopropoxy-2-oxo-2,3,11,12,13,14-hexahydro-1H,10H-8,4-epiazeno-9,15,1,3,6-benzodioxatriazacycloheptadecine-7-carbonitrile;

17-amino-18-chloro-2-oxo-2,3,11,12,13,14-hexahydro-1H,10H-8,4-epiazeno-9,15,1,3,6-benzodioxatriazacycloheptadecine-7-carbonitrile;

17-amino-18-chloro-2-oxo-2,3,11,14-tetrahydro-1H,10H-8,4-epiazeno-9,15,1,3,6-benzodioxatriazacycloheptadecine-7-carbonitrile;

18-chloro-2-oxo-17-[(pyridin-3-ylmethyl)amino]-2,3,11,12,13,14-hexahydro-1H,10H-8,4-epiazeno-9,15,1,3,6-benzodioxatriazacycloheptadecine-7-carbonitrile;

18-chloro-2-oxo-17-[(pyridin-4-ylmethyl)amino]-2,3,11,12,13,14-hexahydro-1H,10H-8,4-epiazeno-9,15,1,3,6-benzodioxatriazacycloheptadecine-7-carbonitrile;

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-2-carboxamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-4-carboxamide;

2-chloro-N-(18-chloro-7-cyano-2-oxo-2,3,11,12,13,14-hexahydro-1H,10H-8,4-epiazeno-9,15,1,3,6-benzodioxatriazacycloheptadecin-17-yl)isonicotinamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)pyridine-3-carboxamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)acetamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-2-(dimethylamino)acetamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-3-(cyclopentylamino)propanamide;

3-chloro-N-(18-chloro-7-cyano-2-oxo-2,3,11,12,13,14-hexahydro-1H,10H-8,4-epiazeno-9,15,1,3,6-benzodioxatriazacycloheptadecin-17-yl)propanamide N-(18-chloro-7-cyano-2-oxo-2,3,11,12,13,14-hexahydro-1H,10H-8,4-epiazeno-9,15,1,3,6-benzodioxatriazacycloheptadecin-17-yl)-3-[cyclohexyl(methyl)amino]propanamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)methanesulfonamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-6-morpholin-4-ylpyridine-3-sulfonamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-2,2,2-trifluoroethanesulfonamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-4-fluorobenzenesulfonamide;

N-(18-chloro-7-cyano-2-oxo-2,3,11,12,13,14-hexahydro-1H,10H-8,4-epiazeno-9,15,1,3,6-benzodioxatriazacycloheptadecin-17-yl)-4-(trifluoromethoxy)benzenesulfonamide;

18-chloro-17-(3-hydroxyprop-1-ynyl)-2-oxo-2,3,11,12,13,14-hexahydro-1H,10H-8,4-epiazeno-9,15,1,3,6-benzodioxatriazacycloheptadecine-7-carbonitrile;

18-chloro-7-cyano-2-oxo-2,3,11,12,13,14-hexahydro-1H,10H-8,4-epiazeno-9,15,1,3,6-benzodioxatriazacycloheptadecin-17-yl trifluoromethanesulfonate;

18-chloro-2-oxo-17-[3-(tetrahydro-2H-pyran-2-yloxy)prop-1-ynyl]-2,3,11,12,13,14-hexahydro-1H,10H-8,4-epiazeno-9,15,1,3,6-benzodioxatriazacycloheptadecine-7-carbonitrile;

18-chloro-2-oxo-17-[3-(tetrahydro-2H-pyran-2-yloxy)propyl]-2,3,11,12,13,14-hexahydro-1H,10H-8,4-epiazeno-9,15,1,3,6-benzodioxatriazacycloheptadecine-7-carbonitrile;

18-chloro-17-(3-hydroxypropyl)-2-oxo-2,3,11,12,13,14-hexahydro-1H,10H-8,4-epiazeno-9,15,1,3,6-benzodioxatriazacycloheptadecine-7-carbonitrile;

18-chloro-17-(2,3-dihydroxypropyl)-2-oxo-2,3,11,12,13,14-hexahydro-1H,10H-8,4-epiazeno-9,15,1,3,6-benzodioxatriazacycloheptadecine-7-carbonitrile;

17-allyl-18-chloro-2-oxo-2,3,11,12,13,14-hexahydro-1H,10H-8,4-epiazeno-9,15,1,3,6-benzodioxatriazacycloheptadecine-7-carbonitrile;

18-chloro-17-(3-hydroxy-3-methylbut-1-ynyl)-2-oxo-2,3,11,12,13,14-hexahydro-1H,10H-8,4-epiazeno-9,15,1,3,6-benzodioxatriazacycloheptadecine-7-carbonitrile;

18-chloro-17-(3-hydroxybut-1-ynyl)-2-oxo-2,3,11,12,13,14-hexahydro-1H,10H-8,4-epiazeno-9,15,1,3,6-benzodioxatriazacycloheptadecine-7-carbonitrile;

18-chloro-17-[3-(diethylamino)prop-1-ynyl]-2-oxo-2,3,11,12,13,14-hexahydro-1H,10H-8,4-epiazeno-9,15,1,3,6-benzodioxatriazacycloheptadecine-7-carbonitrile;

18-chloro-17-[3-(dimethylamino)prop-1-ynyl]-2-oxo-2,3,11,12,13,14-hexahydro-1H,10H-8,4-epiazeno-9,15,1,3,6-benzodioxatriazacycloheptadecine-7-carbonitrile;

18-chloro-17-(dimethylamino)-2-oxo-2,3,11,12,13,14-hexahydro-1H,10H-8,4-epiazeno-9,15,1,3,6-benzodioxatriazacycloheptadecine-7-carbonitrile;

18-chloro-17-(diethylamino)-2-oxo-2,3,11,12,13,14-hexahydro-1H,10H-8,4-epiazeno-9,15,1,3,6-benzodioxatriazacycloheptadecine-7-carbonitrile;

18-chloro-2-oxo-17-piperidin-1-yl-2,3,11,12,13,14-hexahydro-1H,10H-8,4-epiazeno-9,15,1,3,6-benzodioxatriazacycloheptadecine-7-carbonitrile;

18-chloro-17-(isobutylamino)-2-oxo-2,3,11,12,13,14-hexahydro-1H,10H-8,4-epiazeno-9,15,1,3,6-benzodioxatriazacycloheptadecine-7-carbonitrile;

17-chloro-11,12-dihydroxy-2-oxo-2,3,10,11,12,13-hexahydro-1H-8,4-epiazeno-9,14,1,3,6-benzodioxatriazacyclohexadecine-7-carbonitrile;

17-chloro-2-oxo-2,3,10,13-tetrahydro-1H-8,4-epiazeno-9,14,1,3,6-benzodioxatriazacyclohexadecine-7-carbonitrile;

18-chloro-17-(methylamino)-2-oxo-2,3,11,12,13,14-hexahydro-1H,10H-8,4-epiazeno-9,15,1,3,6-benzodioxatriazacycloheptadecine-7-carbonitrile;

14-chloro-11-oxo-2,3,11,12,18,18a-hexahydro-1aH,10H-5,9-epiazenooxireno[1][9,15,1,3,6]benzodioxatriazacycloheptadecine-6-carbonitrile;

18-chloro-11,12-cis-dihydroxy-14-methyl-2-oxo-2,3,11,12,13,14-hexahydro-1H,10H-8,4-epiazeno-9,15,1,3,6-benzodioxatriazacycloheptadecine-7-carbonitrile;

(cis) 18-chloro-14-methyl-2-oxo-2,3,13,14-tetrahydro-1H,10H-8,4-epiazeno-9,15,1,3,6-benzodioxatriazacycloheptadecine-7-carbonitrile;

18-chloro-11,12-trans-dihydroxy-14-methyl-2-oxo-2,3,11,12,13,14-hexahydro-1H,10H-8,4-epiazeno-9,15,1,3,6-benzodioxatriazacycloheptadecine-7-carbonitrile;

(trans) 18-chloro-14-methyl-2-oxo-2,3,13,14-tetrahydro-1H,10H-8,4-epiazeno-9,15,1,3,6-benzodioxatriazacycloheptadecine-7-carbonitrile;

18-chloro-15-methyl-2-oxo-2,3,10,11,12,13,14,15-octahydro-1H-8,4-epiazeno-9,1,3,6,15-benzoxatetraazacycloheptadecine-7-carbonitrile;

(cis) 18-chloro-13-hydroxy-2-oxo-2,3,13,14-tetrahydro-1H,10H-8,4-epiazeno-9,15,1,3,6-benzodioxatriazacycloheptadecine-7-carbonitrile;

18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile;

18-chloro-13-hydroxy-2-oxo-2,3,11,12,13,14-hexahydro-1H,10H-8,4-epiazeno-9,15,1,3,6-benzodioxatriazacycloheptadecine-7-carbonitrile;

(trans, trans) 18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile;

(cis, trans) 18-chloro-11,12,13-trihydroxy-2-oxo-2,3,11,12,13,14-hexahydro-1H,10H-8,4-epiazeno-9,15,1,3,6-benzodioxatriazacycloheptadecine-7-carbonitrile;

18-bromo-2-oxo-2,3,11,14-tetrahydro-1H,10H-8,4-epiazeno-9,15,1,3,6-benzodioxatriazacycloheptadecine-7-carbonitrile;

18-bromo-12,13dihydroxy-2-oxo-2,3,11,12,13,14-hexahydro-1H,10H-8,4-epiazeno-9,15,1,3,6-benzodioxatriazacycloheptadecine-7-carbonitrile;

2-oxo-18-[3-(tetrahydro-2H-pyran-2-yloxy)propyl]-2,3,11,14-tetrahydro-1H,10H-8,4-epiazeno-9,15,1,3,6-benzodioxatriazacycloheptadecine-7-carbonitrile;

2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile;

18-(3-hydroxypropyl)-2-oxo-2,3,11,14-tetrahydro-1H,10H-8,4-epiazeno-9,15,1,3,6-benzodioxatriazacycloheptadecine-7-carbonitrile;

18-(2-hydroxyethyl)-2-oxo-2,3,11,14-tetrahydro-1H,10H-8,4-epiazeno-9,15,1,3,6-benzodioxatriazacycloheptadecine-7-carbonitrile;

18-bromo-2-oxo-2,3,11,12,13,14-hexahydro-1H,10H-8,4-epiazeno-9,15,1,3,6-benzodioxatriazacycloheptadecine-7-carbonitrile;

18-hydroxy-2-oxo-2,3,11,14-tetrahydro-1H,10H-8,4-epiazeno-9,15,1,3,6-benzodioxatriazacycloheptadecine-7-carbonitrile;

18-(2-hydroxyethyl)-2-oxo-2,3,11,12,13,14-hexahydro-1H,10H-8,4-epiazeno-9,15,1,3,6-benzodioxatriazacycloheptadecine-7-carbonitrile;

18-(3-hydroxypropyl)-2-oxo-2,3,11,12,13,14-hexahydro-1H,10H-8,4-epiazeno-9,15,1,3,6-benzodioxatriazacycloheptadecine-7-carbonitrile;

12,13-dihydroxy-18-(2-hydroxyethyl)-2-oxo-2,3,11,12,13,14-hexahydro-1H,10H-8,4-epiazeno-9,15,1,3,6-benzodioxatriazacycloheptadecine-7-carbonitrile;

12,13-dihydroxy-18-(3-hydroxypropyl)-2-oxo-2,3,11,12,13,14-hexahydro-1H,10H-8,4-epiazeno-9,15,1,3,6-benzodioxatriazacycloheptadecine-7-carbonitrile;

18-chloro-13-methoxy-2-oxo-2,3,13,14-tetrahydro-1H,10H-8,4-epiazeno-9,15,1,3,6-benzodioxatriazacycloheptadecine-7-carbonitrile;

18-chloro-11,12-dihydroxy-13-methoxy-2-oxo-2,3,11,12,13,14-hexahydro-1H,10H-8,4-epiazeno-9,15,1,3,6-benzodioxatriazacycloheptadecine-7-carbonitrile;

18-chloro-11,12-dihydroxy-13-methoxy-2-oxo-2,3,11,12,13,14-hexahydro-1H,10H-8,4-epiazeno-9,15,1,3,6-benzodioxatriazacycloheptadecine-7-carbonitrile;

18-chloro-13-ethoxy-11,12-cis-dihydroxy-2-oxo-2,3,11,12,13,14-hexahydro-1H,10H-8,4-epiazeno-9,15,1,3,6-benzodioxatriazacycloheptadecine-7-carbonitrile;

(cis) 18-chloro-13-ethoxy-2-oxo-2,3,13,14-tetrahydro-1H,10H-8,4-epiazeno-9,15,1,3,6-benzodioxatriazacycloheptadecine-7-carbonitrile;

18-chloro-13-ethoxy-11,12-trans-dihydroxy-2-oxo-2,3,11,12,13,14-hexahydro-1H,10H-8,4-epiazeno-9,15,1,3,6-benzodioxatriazacycloheptadecine-7-carbonitrile;

(cis) 18-nitro-2-oxo-2,3,13,14-tetrahydro-1H,10H-8,4-epiazeno-9,15,1,3,6-benzodioxatriazacycloheptadecine-7-carbonitrile;

18-ethoxy-2-oxo-2,3,11,14-tetrahydro-1H,10H-8,4-epiazeno-9,15,1,3,6-benzodioxatriazacycloheptadecine-7-carbonitrile;

18-chloro-17-(ethylamino)-2-oxo-2,3,11,12,13,14-hexahydro-1H,10H-8,4-epiazeno-9,15,1,3,6-benzodioxatriazacycloheptadecine-7-carbonitrile;

17-(butylamino)-18-chloro-2-oxo-2,3,11,12,13,14-hexahydro-1H,10H-8,4-epiazeno-9,15,1,3,6-benzodioxatriazacycloheptadecine-7-carbonitrile;

17-chloro-2-oxo-2,3,10,11,12,13-hexahydro-1H-8,4-epiazeno-9,14,1,3,6-benzodioxatriazacyclohexadecine-7-carbonitrile;

18-chloro-14-methyl-2-oxo-2,3,11,14-tetrahydro-1H,10H-8,4-epiazeno-9,15,1,3,6-benzodioxatriazacycloheptadecine-7-carbonitrile;

18-bromo-16-fluoro-12,13-dihydroxy-2-oxo-2,3,11,12,13,14-hexahydro-1H,10H-8,4-epiazeno-9,15,1,3,6-benzodioxatriazacycloheptadecine-7-carbonitrile;

18-bromo-16-fluoro-2-oxo-2,3,11,14-tetrahydro-1H,10H-8,4-epiazeno-9,15,1,3,6-benzodioxatriazacycloheptadecine-7-carbonitrile;

(cis) 19-chloro-2-oxo-2,3,10,11,14,15-hexahydro-1H-8,4-epiazeno-9,16,1,3,6-benzodioxatriazacyclooctadecine-7-carbonitrile;

(trans) 19-chloro-2-oxo-2,3,10,11,14,15-hexahydro-1H-8,4-epiazeno-9,16,1,3,6-benzodioxatriazacyclooctadecine-7-carbonitrile;

(12R,13S)-19-chloro-12,13-cis-dihydroxy-2-oxo-2,3,10,11,12,13,14,15-octahydro-1H-8,4-epiazeno-9,16,1,3-benzodioxadiazacyclooctadecine-7-carbonitrile;

(12R,13S)-19-chloro-12,13-trans-dihydroxy-2-oxo-2,3,10,11,12,13,14,15-octahydro-1H-8,4-epiazeno-9,16,1,3-benzodioxadiazacyclooctadecine-7-carbonitrile;

19-chloro-2-oxo-2,3,10,11,12,13,14,15-octahydro-1H-8,4-epiazeno-9,16,1,3,6-benzodioxatriazacyclooctadecine-7-carbonitrile;

18-methyl-2-oxo-2,3,11,14-tetrahydro-1H,10H-8,4-epiazeno-9,15,1,3,6-benzodioxatriazacycloheptadecine-7-carbonitrile;

18-methyl-2-oxo-2,3,11,12,13,14-hexahydro-1H,10H-8,4-epiazeno-9,15,1,3,6-benzodioxatriazacycloheptadecine-7-carbonitrile;

16-bromo-18-methyl-2-oxo-2,3,11,14-tetrahydro-1H,10H-8,4-epiazeno-9,15,1,3,6-benzodioxatriazacycloheptadecine-7-carbonitrile;

16-bromo-18-methyl-2-oxo-2,3,11,12,13,14-hexahydro-1H,10H-8,4-epiazeno-9,15,1,3,6-benzodioxatriazacycloheptadecine-7-carbonitrile;

16-(3-hydroxyprop-1-ynyl)-18-methyl-2-oxo-2,3,11,12,13,14-hexahydro-1H,10H-8,4-epiazeno-9,15,1,3,6-benzodioxatriazacycloheptadecine-7-carbonitrile;

18-chloro-17-hydroxy-2-oxo-2,3,11,12,13,14-hexahydro-1H,10H-8,4-metheno-9,15,1,3-benzodioxadiazacycloheptadecine-7-carbonitrile;

11,12-cis-dihydroxy-18-nitro-2-oxo-2,3,11,12,13,14-hexahydro-1H,10H-8,4-epiazeno-9,15,1,3,6-benzodioxatriazacycloheptadecine-7-carbonitrile;

11,12-trans-dihydroxy-18-nitro-2-oxo-2,3,11,12,13,14-hexahydro-1H,10H-8,4-epiazeno-9,15,1,3,6-benzodioxatriazacycloheptadecine-7-carbonitrile;

18-ethoxy-12,13-dihydroxy-2-oxo-2,3,11,12,13,14-hexahydro-1H,10H-8,4-epiazeno-9,15,1,3,6-benzodioxatriazacycloheptadecine-7-carbonitrile;

18-methoxy-2-oxo-2,3,11,14-tetrahydro-1H,10H-8,4-epiazeno-9,15,1,3,6-benzodioxatriazacycloheptadecine-7-carbonitrile;

2-oxo-18-[2-(tetrahydro-2H-pyran-2-yloxy)ethoxy]-2,3,11,14-tetrahydro-1H,10H-8,4-epiazeno-9,15,1,3,6-benzodioxatriazacycloheptadecine-7-carbonitrile;

12,13-dihydroxy-18-methoxy-2-oxo-2,3,11,12,13,14-hexahydro-1H,10H-8,4-epiazeno-9,15,1,3,6-benzodioxatriazacycloheptadecine-7-carbonitrile;

18-(2-hydroxyethoxy)-2-oxo-2,3,11,14-tetrahydro-1H,10H-8,4-epiazeno-9,15,1,3,6-benzodioxatriazacycloheptadecine-7-carbonitrile; and 18-[2-(dimethylamino)ethoxy]-2-oxo-2,3,11,14-tetrahydro-1H,10H-8,4-epiazeno-9,15,1,3,6-benzodioxatriazacycloheptadecine-7-carbonitrile.

6. A pharmaceutical composition comprising a compound of claim 1 or a therapeutically acceptable salt thereof, in combination with a therapeutically acceptable carrier.

* * * * *